US012781185B2

(12) United States Patent
Anand et al.

(10) Patent No.: US 12,781,185 B2
(45) **Date of Patent: *Nov. 3, 2026**

(54) NEURAL ORGANOID COMPOSITION AND METHODS OF USE

(71) Applicant: NEURXSTEM, INC., Columbus, OH (US)

(72) Inventors: Rene Anand, Westerville, OH (US); Susan Mckay, Columbus, OH (US)

(73) Assignee: NEURXSTEM, INC., Columbus, OH (US)

( * ) Notice: Subject to any disclaimer, the term of this patent is extended or adjusted under 35 U.S.C. 154(b) by 1067 days.

This patent is subject to a terminal disclaimer.

(21) Appl. No.: 17/709,136

(22) Filed: Mar. 30, 2022

(65) Prior Publication Data

US 2022/0290100 A1 Sep. 15, 2022

Related U.S. Application Data

(63) Continuation of application No. 16/068,840, filed as application No. PCT/US2017/013231 on Jan. 12, 2017, now Pat. No. 11,345,890.

(60) Provisional application No. 62/298,872, filed on Feb. 23, 2016, provisional application No. 62/278,857, filed on Jan. 14, 2016.

(51) Int. Cl.

| | |
|---|---|
| ***C12N 5/079*** | (2010.01) |
| ***A61K 35/30*** | (2015.01) |
| ***A61L 27/22*** | (2006.01) |
| ***A61L 27/36*** | (2006.01) |
| ***A61L 27/38*** | (2006.01) |
| ***C12N 5/00*** | (2006.01) |
| ***C12N 5/0793*** | (2010.01) |

(52) U.S. Cl.

CPC ............ *C12N 5/0622* (2013.01); *A61K 35/30* (2013.01); *A61L 27/222* (2013.01); *A61L 27/3641* (2013.01); *A61L 27/383* (2013.01); *A61L 27/3878* (2013.01); *C12N 5/0062* (2013.01); *C12N 5/0618* (2013.01); *C12N 5/0619* (2013.01); *C12N 5/0621* (2013.01); *C12N 2501/115* (2013.01); *C12N 2501/727* (2013.01); *C12N 2503/02* (2013.01); *C12N 2506/45* (2013.01); *C12N 2513/00* (2013.01); *C12N 2533/90* (2013.01)

(58) Field of Classification Search

CPC .. C12N 5/0622; C12N 5/0062; C12N 5/0618; C12N 5/0619; C12N 5/0621; C12N 2501/115; C12N 2501/727; C12N 2503/02; C12N 2506/45; C12N 2513/00; C12N 2533/90; A61L 27/222; A61L 27/3641; A61L 27/383; A61L 27/3878; A61K 35/30; A61P 19/00; A61P 43/00

See application file for complete search history.

(56) References Cited

U.S. PATENT DOCUMENTS

| | | | |
|---|---|---|---|
| 2006/0171935 | A1 | 8/2006 | Abeliovich et al. |
| 2014/0030805 | A1 | 1/2014 | Kasuto et al. |
| 2015/0330970 | A1 | 11/2015 | Knoblich et al. |
| 2016/0186146 | A1 | 6/2016 | Thomson et al. |
| 2019/0017018 | A1 | 1/2019 | Anand et al. |

FOREIGN PATENT DOCUMENTS

| | | | |
|---|---|---|---|
| WO | 2013130769 | A1 | 9/2013 |
| WO | 2014090993 | A1 | 6/2014 |
| WO | 2014168585 | A1 | 10/2014 |
| WO | 2015069736 | A1 | 5/2015 |
| WO | 2015121687 | A1 | 8/2015 |

OTHER PUBLICATIONS

Office Action dated Apr. 29, 2022 in corresponding Chinese Patent Application No. 201780017660.2 (5 pages).

English translation of the Office Action dated Apr. 29, 2022 in corresponding Chinese Patent Application No. 201780017660.2 (8 pages).

Anand et al. "Human Neural Organoids 'NexGen' Platforms for CNS Disease, Therapeutic Target, & Drug Discovery Research," The World CNS Summit 2016, Feb. 23, 2016, pp. 1-70.

Anand et al., "Advancing Predictive and Precision Medicine Using Human Neural Organoid Models of Brain Diseases Challenges Understanding Aging Through Biomarkers Across Populations: the Example of Calcium," Jul. 1, 2017 (Jul. 1, 2017), XP055604283, Retrieved from the Internet: URL: https://academic.oup.com/innovateage/article-pdf/1/suppl_1/1314/26111133/igx004.4813.pdf [retrieved on Jul. 10, 2019]; abstract.

Bamba et al., "Generation of cerebral cortex-like structure from human pluripotent stem cells," Nippon Rinsho (Japanese Journal of Clinical Medicine) (separate volume), Saisei Iryo (Regenerative Medicine), vol. 73, Suppl. 5, Shuji Kawaratani, Nipponrinshosha Co., Ltd., vol. 73, pp. 130-609 (Year: 2015).

Huang et al., "Expression of Transcription Factor Satb2 in Adult Mouse Brain," The Anatomical Record, Mar. 2013, vol. 296, No. 3, pp. 452-461.

Jurga et al., "Generation of Functional Neural Artificial Tissue from Human Umbilical Cord Blood Stem Cells," Tissue Engineering Part C: Methods, Sep. 2009, vol. 15, No. 3, pp. 365-372.

Kaewkhaw et al., "Transcriptome Dynamics of Developing Photoreceptors in Three-Dimensional Retina Cultures Recapitulates Temporal Sequence of Human Cone and Rod Differentiation Revealing Cell Surface Markers and Gene Networks," Stem Cells, 2015, vol. 33, pp. 3504-3518.

(Continued)

*Primary Examiner* — Titilayo Moloye

(74) *Attorney, Agent, or Firm* — Greenberg Traurig, LLP; Melissa Hunter-Ensor; Evelyn M. Kwon

(57) ABSTRACT

The present invention features a neural organoid that recapitulates in vitro most characteristics of the brain (e.g., human), and methods of using this neural organoid to study disease and to identify therapeutic agents for the treatment of neurological diseases and disorders.

20 Claims, 30 Drawing Sheets

Specification includes a Sequence Listing.

(56) References Cited

OTHER PUBLICATIONS

Kondo et al., "Modeling Alzheimer's Disease with iPSCs Reveals Stress Phenotypes Associated with Intracellular Aβ and Differential Drug Responsiveness," Cell Stem Cell, Apr. 4, 2013, vol. 12, No. 4, pp. 487-496.

Lancaster et al., "Generation of Cerebral Organoids from Human Pluripotent Stem Cells," Nature Protocols, Sep. 4, 2014, vol. 9, No. 10, pp. 2329-2340.

Lin et al., "Heat Shock Alters the Expression of Schizophrenia and Autism Candidate Genes in an Induced Pluripotent Stem Cell Model of the Human Telencephalon," PLoS One, Apr. 15, 2014, vol. 9, No. 4, e94968, pp. 1-11.

Mahairaki et al., "Induced Pluripotent Stem Cells from Familial Alzheimer's Disease Patients Differentiate into Mature Neurons with Amyloidogenic Properties," Stem Cells and Development, Dec. 15, 2014, vol. 23, No. 24, pp. 2996-3010.

Ninkovic et al., "The Transcription Factor Pax6 Regulates Survival of Dopaminergic Olfactory Bulb Neurons via Crystallin αA," Neuron, Nov. 18, 2010, vol. 68, No. 4, pp. 682-694.

Pasca et al., "Functional cortical neurons and astrocytes from human pluripotent stem cells in 3D culture," Nature Methods, 2015, vol. 12, No. 7, pp. 671-678.

Van De Leemput et al., "Cortecon: A Temporal Transcriptome Analysis of In Vitro Human Cerebral Cortex Development from Human Embryonic Stem Cells," Neuron, Jul. 2, 2014, vol. 83, No. 1, pp. 51-68.

Zhong et al., "Generation of three-dimensional retinal tissue with functional photoreceptors from human iPSCs," Nature Communications, Jun. 10, 2014, vol. 5, Article No. 4047, pp. 1-14.

International Search Report and Written Opinion mailed Apr. 25, 2017 in corresponding PCT Patent Application No. PCT/US2017/013231 (12 pages).

Extended European Search Report dated Jul. 22, 2019 in corresponding European Patent Application No. 17738958.2 (8 pages).

Office Action dated Feb. 10, 2021 in corresponding Japanese Patent Application No. 2018-555834 (4 pages).

English translation of the Office Action dated Feb. 10, 2021 in corresponding Japanese Patent Application No. 2018-555834 (4 pages).

First Office Action dated May 10, 2021 in corresponding Chinese Patent Application No. 201780017660.2 (5 pages).

English translation of the First Office Action dated May 10, 2021 in corresponding Chinese Patent Application No. 201780017660.2 (5 pages).

Office Action dated Jun. 16, 2021 in corresponding European Patent Application No. 17738958.2 (5 pages).

Second Office Action dated Dec. 31, 2021 in corresponding Chinese Patent Application No. 201780017660.2 (5 pages).

English translation of the Second Office Action dated Dec. 31, 2021 in corresponding Chinese Patent Application No. 201780017660.2 (7 pages).

| | 1 week | 4 weeks | 12 Weeks | |
|---|---|---|---|---|
| SLC12A2 | 31.792 | 54.439 | 35.969 | NKCC1 |
| SLC12A5 | 0 | 0.446 | 1.628 | KCC2 |

FIG. 5B

| Class | Genes | | | | | | | | | |
|---|---|---|---|---|---|---|---|---|---|---|
| Excitatory | GRIA1 | GRIA2 | GRIA3 | GRIA4 | GRIN2A | GRIN2B | GRIN2C | SLC1A1 | SLC1A2 | |
| Inhibitory | GABRA1 | GABRA2 | GABRA3 | GABRR1 | GABRR2 | SLC6A13 | GABRA6 | | | |
| Cholinergic | CHRM1 | CHRM2 | CHRM3 | CHRNA1 | CHRNA3 | CHRNA4 | CHRNB2 | CHRNB3 | CHRNB4 | VAT1 |
| Dopaminergic | TH | DAT | DRD1 | DRD2 | DRD3 | DRD4 | COMT | DDC | SLC18A1 | SLCA18A2 |
| Serotonergic | HTR1A | HTR1B | HRT1C | HTR1D | HTR2A | HTR2C | MAOA | DDC | SLC6A2 | SLC6A4 |
| Astrocytic | GFAP | | | | | | | | | |
| Oligodendritic | OLIG1 | OLIG2 | MOBP | MBB | PLP1 | OMD | MOGS | | | |
| Microgial | AIF1 | CD4 | ICAM | | | | | | | |
| Vasculature | NOS3 | ANGPT1 | EDN3 | VEGFA | | | | | | |

FIG. 5C

COMPARISON: Organoid versus Human Brain Reference; CONCORDANCE >98%

| GENE | 12 week | HBR |
|---|---|---|
| A1BG | 0.977 | 9 |
| A1CF | 0.651 | 0 |
| A2M | 28.97 | 827 |
| A2M-AS1 | 3.418 | 64 |
| A2ML1 | 0.163 | 0 |
| A2MP1 | 0 | 0 |
| A4GALT | 1.79 | 60 |
| A4GNT | 0 | 0 |
| AA06 | 0 | 32 |
| AAAS | 26.854 | 174 |
| AACS | 20.019 | 331 |
| AACSP1 | 0.651 | 2 |
| AADAC | 3.581 | 0 |
| AADACL2 | 0 | 0 |
| AADACL3 | 0 | 0 |
| AADACL4 | 0 | 0 |
| AADAT | 20.344 | 114 |
| AAED1 | 6.347 | 52 |
| AAGAB | 48.664 | 601 |
| AAK1 | 10.091 | 2501 |
| AAMDC | 23.762 | 118 |
| AAMP | 50.779 | 939 |
| AANAT | 0 | 0 |
| AAR2 | 41.828 | 359 |
| AARD | 0.814 | 15 |
| AARS | 256.664 | 4850 |
| AARS2 | 13.02 | 145 |
| AASDH | 7.324 | 72 |
| AASDHPPT | 147.781 | 1081 |
| AASS | 9.44 | 63 |
| AATF | 65.265 | 657 |
| AATK | 11.393 | 1503 |
| ABAT | 105.953 | 5228 |
| ABCA1 | 51.756 | 175 |
| ABCA10 | 3.255 | 153 |

| | | |
|---|---|---|
| ABI1 | 77.308 | 1601 |
| ABI2 | 47.362 | 941 |
| ABI3 | 1.139 | 158 |
| ABI3BP | 62.498 | 129 |
| ABL1 | 196.77 | 742 |
| ABL2 | 43.13 | 1031 |
| ABLIM1 | 7.161 | 1547 |
| ABLIM2 | 0.651 | 559 |
| ABLIM3 | 0.814 | 211 |
| ABO | 0.163 | 6 |
| ABP1 | 0.814 | 0 |
| ABR | 4.72 | 432 |
| ABRA | 0 | 5 |
| ABRACL | 41.665 | 201 |
| ABT1 | 28.482 | 234 |
| ABTB1 | 17.74 | 2568 |
| ABTB2 | 9.603 | 199 |
| ACAA1 | 24.088 | 425 |
| ACAA2 | 57.452 | 254 |
| ACACA | 42.316 | 491 |
| ACACB | 18.88 | 244 |
| ACAD10 | 14.16 | 136 |
| ACAD11 | 43.618 | 280 |
| ACAD8 | 25.39 | 580 |
| ACAD9 | 23.762 | 369 |
| ACADL | 1.953 | 22 |
| ACADM | 32.714 | 270 |
| ACADS | 13.183 | 173 |
| ACADSB | 7.649 | 257 |

| | | |
|---|---|---|
| ACTA1 | 28.482 | 17 |
| ACTA2 | 119.95 | 702 |
| ACTB | 2844.786 | 47548 |
| ACTBL2 | 0.326 | 0 |
| ACTC1 | 84.795 | 10 |
| ACTG1 | 5171.035 | 35006 |
| ACTG1P4 | 1.302 | 104 |
| ACTG2 | 3.418 | 46 |
| ACTL10 | 5.371 | 34 |
| ACTL6A | 14.322 | 39 |
| ACTL6B | 6.185 | 352 |
| ACTL7A | 0 | 0 |
| ACTL7B | 0 | 0 |
| ACTL8 | 0.163 | 0 |
| ACTL9 | 0 | 0 |
| ACTN1 | 97.164 | 618 |
| ACTN2 | 14.811 | 358 |
| ACTN3 | 0.814 | 31 |
| ACTN4 | 224.113 | 2508 |
| ACTR10 | 156.407 | 1718 |
| ACTR1A | 95.862 | 1353 |
| ACTR1B | 42.479 | 1514 |
| ACTR2 | 334.949 | 4120 |
| ACTR3 | 198.235 | 1318 |
| ACTR3B | 6.673 | 199 |
| ACTR3BP2 | 0.326 | 0 |
| ACTR3C | 0 | 22 |
| ACTR5 | 7.161 | 92 |
| ACTR6 | 32.551 | 432 |

FIG. 5D

COMPARISON: Two Independent Organoid Samples; Reproducibility >99%

| | | |
|---|---|---|
| A1BG | 0.977 | 2.934 |
| A1CF | 0.651 | 1.334 |
| A2M | 28.97 | 42.28 |
| A2M-AS1 | 3.418 | 4.735 |
| A2ML1 | 0.163 | 0 |
| A2MP1 | 0 | 0 |
| A4GALT | 1.79 | 5.535 |
| A4GNT | 0 | 0 |
| AA06 | 0 | 0.267 |
| AAAS | 26.854 | 35.144 |
| AACS | 20.019 | 18.406 |
| AACSP1 | 0.651 | 0.133 |
| AADAC | 3.581 | 3.001 |
| AADACL2 | 0 | 0 |
| AADACL3 | 0 | 0 |
| AADACL4 | 0 | 0 |
| AADAT | 20.344 | 10.803 |
| AAED1 | 6.347 | 11.403 |
| AAGAB | 48.664 | 36.078 |
| AAK1 | 10.091 | 8.002 |
| AAMDC | 23.762 | 24.207 |
| AAMP | 50.779 | 61.419 |
| AANAT | 0 | 0.2 |
| AAR2 | 41.828 | 55.017 |
| AARD | 0.814 | 3.401 |
| AARS | 256.664 | 309.094 |
| AARS2 | 13.02 | 19.206 |
| AASDH | 7.324 | 2.734 |
| AASDHPPT | 147.781 | 51.883 |
| AASS | 9.44 | 11.737 |
| AATF | 65.265 | 43.413 |

| | | |
|---|---|---|
| ABCD3 | 48.826 | 38.545 |
| ABCD4 | 43.781 | 43.947 |
| ABCE1 | 133.621 | 103.432 |
| ABCF1 | 62.009 | 61.285 |
| ABCF2 | 70.147 | 43.147 |
| ABCF3 | 13.183 | 24.207 |
| ABCG1 | 0.977 | 2.334 |
| ABCG2 | 1.628 | 1.6 |
| ABCG4 | 3.092 | 2.134 |
| ABCG5 | 0 | 0.467 |
| ABCG8 | 0 | 0.333 |
| ABHD1 | 0.163 | 1.334 |
| ABHD10 | 15.462 | 21.073 |
| ABHD11 | 8.463 | 17.405 |
| ABHD12 | 63.637 | 34.21 |
| ABHD12B | 0 | 0 |
| ABHD13 | 4.557 | 17.072 |
| ABHD14A | 6.347 | 15.872 |
| ABHD14B | 23.437 | 57.551 |
| ABHD15 | 7.975 | 12.004 |
| ABHD16A | 29.459 | 29.009 |
| ABHD16B | 4.069 | 3.268 |
| ABHD2 | 131.017 | 266.815 |
| ABHD3 | 22.623 | 21.14 |
| ABHD4 | 28.482 | 65.487 |
| ABHD5 | 18.88 | 19.806 |
| ABHD6 | 15.136 | 28.209 |
| ABHD8 | 13.834 | 18.872 |
| ABI1 | 77.308 | 87.96 |
| ABI2 | 47.362 | 59.685 |
| ABI3 | 1.139 | 2.667 |

| | | |
|---|---|---|
| ACP5 | 2.767 | 3.401 |
| ACP6 | 30.435 | 26.208 |
| ACPL2 | 79.912 | 63.819 |
| ACPP | 7.649 | 9.536 |
| ACPT | 0 | 0.067 |
| ACR | 3.255 | 3.801 |
| ACRBP | 2.767 | 2.801 |
| ACRC | 1.79 | 1.534 |
| ACRV1 | 0 | 0.067 |
| ACSBG1 | 0.488 | 0.267 |
| ACSBG2 | 0 | 0.067 |
| ACSF2 | 38.736 | 28.342 |
| ACSF3 | 12.044 | 14.138 |
| ACSL1 | 40.038 | 27.942 |
| ACSL3 | 153.315 | 44.614 |
| ACSL4 | 74.216 | 53.35 |
| ACSL5 | 1.302 | 1.4 |
| ACSL6 | 0.651 | 2.067 |
| ACSM1 | 0 | 0.067 |
| ACSM2A | 0 | 0.867 |
| ACSM2B | 0 | 0.267 |
| ACSM3 | 4.557 | 4.935 |
| ACSM4 | 0 | 0 |
| ACSM5 | 0 | 0 |
| ACSS1 | 50.291 | 32.943 |
| ACSS2 | 0.488 | 0 |
| ACSS3 | 11.067 | 11.537 |
| ACTA1 | 28.482 | 3.468 |
| ACTA2 | 119.95 | 176.187 |
| ACTB | 2844.786 | 3943.537 |
| ACTBL2 | 0.326 | 0.6 |

COMPARISON: Organoid & BRAIN versus OTHER ORGANS Disconcordance > 95%

| | | | |
|---|---|---|---|
| BPIFA1 | 0 | 0 | **UPPER AIRWAYS** Antimicrobial; |
| BPIFA1 | 0 | 0 | |
| BPIFA3 | 0 | 0 | |
| BPIFA4P | 0 | 0 | |
| BPIFB1 | 0.488 | | |
| BPIFB2 | 0 | 0 | |
| BPIFB3 | 0 | 0 | |
| BPIFB4 | 0 | 0 | |
| BPIFB6 | 0 | 0 | |
| BPIFC | 0 | 0 | |
| ADH1A | 0 | [redacted] | **LIVER** Alcohol dehydrogenase 1A; |
| ADIPOQ | 0 | 0 | **ADIPOSE** adiponectin adipose |
| AMELX | 0.488 | 0 | **TOOTH** Amelogenins are involved in biomineralization during tooth enamel development |
| AMELY | 0 | 0 | |
| BPIFA1 | 0 | 0 | **UPPER AIRWAYS** Antimicroial protein expressed in the upper airways and nasopharyngeal regions |
| BPIFA2 | 0 | 0 | |
| BPIFA3 | 0 | 0 | |
| BPIFA4P | 0 | 0 | |
| BPIFB1 | 0.488 | 0 | |
| BPIFB2 | 0 | 0 | |
| BPIFB3 | 0 | 0 | |
| BPIFB4 | 0 | 0 | |
| BPIFB6 | 0 | 0 | |
| BPIFC | 0 | 0 | |
| C17orf68 | 0.163 | 0 | **TESTIS** chromosome 17 open reading frame 74; testis |
| C1orf68 | 0 | 0 | **SKIN** chromosome 1 open reading frame 68; skin |
| C8A | 0 | 0 | **Macrophage** C8 is a component of the complement system and contains three polypeptides, alpha, beta and gamma |
| C8B | 0 | 0 | |
| C8G | 0 | 0 | |
| CST1 | 0 | 0 | |
| CST11 | 0 | 0 | |
| CST13P | 0 | 0 | |
| CST2 | 0 | 0 | |
| CST4 | 0 | 0 | **TESTIS** The protein is an S-type cyctatin, based on its high level of expression in saliva, tears and seminal plasma |
| CST5 | 0 | 0 | **SALIVARY**; Salivary gland |

FIG. 6B

| | | |
|---|---|---|
| DEFA10P | 0 | 0 |
| DEFA1B | 0 | 0 |
| DEFA3 | 0 | 1 |
| DEFA4 | 0 | 0 |
| DEFA5 | 0 | 1 |
| DEFA6 | 0 | 0 |
| DEFB1 | 0.814 | |
| DEFB103A | 0 | 0 |
| DEFB104B | 0 | 0 |
| DEFB106B | 0 | 0 |
| DEFB107A | 0 | 0 |
| DEFB109P1 | 0 | 0 |
| DEFB109P1B | 0 | 0 |
| DEFB110 | 0 | 0 |
| DEFB112 | 0 | 0 |
| DEFB113 | 0 | 0 |
| DEFB114 | 0 | 0 |
| DEFB115 | 0 | 0 |
| DEFB116 | 0 | 0 |
| DEFB118 | 0 | 0 |
| DEFB119 | 0.814 | 0 |
| DEFB121 | 0 | 0 |
| DEFB123 | 0 | 0 |
| DEFB124 | 0 | 0 |
| DEFB125 | 0 | 0 |
| DEFB126 | 0 | 0 |
| DEFB127 | 0 | 0 |
| DEFB128 | 0 | 0 |
| DEFB129 | 0 | 0 |
| DEFB130 | 0 | 0 |
| DEFB131 | 0 | 0 |
| DEFB132 | 0 | 0 |
| DEFB133 | 0 | 0 |
| DEFB134 | 0 | 0 |
| DEFB135 | 0 | 0 |
| DEFB136 | 0 | 0 |
| DEFB4A | 0 | 0 |
| DEFB4B | 0 | 0 |

BONE MARROW defensin, alpha 4, corticostatin; bone marrow

FIG. 6C

| | | OLF. EPITHELIUM |
|---|---|---|
| OR10A7 | 0.488 | 0 |
| OR10AD1 | 0.163 | [redacted] |
| OR10AG1 | 0 | 0 |
| OR10C1 | 0.163 | [redacted] |
| OR10G2 | 0.488 | 1 |
| OR10G3 | 0.163 | 0 |
| OR10G4 | 0.488 | 0 |
| OR10G7 | 0 | 1 |
| OR10G8 | 0.488 | 0 |
| OR10G9 | 0 | 1 |
| OR10H1 | 0 | 0 |
| OR10H2 | 0 | 0 |
| OR10H3 | 0 | 0 |
| OR10H4 | 0 | 0 |
| OR10H5 | 0.488 | 0 |
| OR10J1 | 0.163 | 0 |
| OR10J3 | 0.163 | 0 |
| OR10J5 | 0 | 0 |
| OR10K1 | 0.814 | 0 |
| OR10K2 | 0.163 | 0 |
| OR10P1 | 0 | 0 |
| OR10Q1 | 0.326 | 0 |
| OR10R2 | 0 | 0 |
| OR10S1 | 0.163 | 0 |
| OR10T2 | 0 | 0 |
| OR10V1 | 0.651 | [redacted] |
| OR10W1 | 0.163 | 0 |
| OR10X1 | 0.326 | 1 |
| OR10Z1 | 0.163 | 0 |
| OR11A1 | 0 | 0 |
| OR11G2 | 0.326 | 0 |
| OR11H1 | 0 | 0 |
| OR11H12 | 1.953 | 0 |
| OR11H2 | 0.326 | 0 |
| OR11H4 | 0.326 | 2 |
| OR11H6 | 0.326 | 0 |
| OR11L1 | 0 | 1 |
| OR11D2 | 0.163 | 0 |
| OR11D3 | 0 | 0 |
| OR13A1 | 0 | 0 |
| OR13C2 | 0.814 | 1 |

FIG. 6D

| | S | ORGANOIDS | | HUMAN BRAIN | |
|---|---|---|---|---|---|
| | 1 week | 4 weeks | 12 Weeks | HBR | |
| ATOH1 | 11.922 | 0.223 | 0 | 0 | |
| PAX6 | 11.922 | 161.086 | 32.714 | 9.26 | |
| BARHL1 | 0 | 1.339 | 0.814 | 5.56 | |
| SOX2 | 39.739 | 185.181 | 58.917 | 55.3 | |
| LHX2 | 7.948 | 252.784 | 17.903 | 16 | |
| TBR1 | 11.922 | 0.223 | 0.326 | 29 | |
| KIRREL2 | 3.974 | 20.749 | 13.671 | 1.3 | |
| PTF1A | 0 | 0 | 1.302 | 0.125 | |
| GRID2 | 0 | 0 | 14.811 | 35.7 | purkinje |
| PCP2 | 0 | 0.446 | 0.326 | 48 | L7 purkinje |

http://dx.doi.org/10.1016/j.celrep.2014.12.051

ORGANOIDS

| | 1 week | 4 weeks | 12 Weeks | |
|---|---|---|---|---|
| SOX2 | 39.739 | 185.181 | 58.917 | |
| ASCL1 | 0 | 5.578 | 7.975 | |
| NEUROD1 | 0 | 47.969 | 31.249 | |
| DCX | 0 | 20.749 | 23.925 | |
| EOMES | 3.974 | 1.339 | 1.139 | Ngn2 |
| EMX2 | 0 | 72.288 | 10.091 | |
| FOXG1 | 0 | 39.267 | 12.695 | |
| NEUROG2 | 0 | 1.116 | 2.279 | NeuroD1 |
| PROX1 | 202.671 | 40.829 | 28.645 | |
| RBFOX3 | 0 | 2.454 | 8.789 | NeuN |

| | ORGANOIDS 1 week | ORGANOIDS 4 weeks | ORGANOIDS 12 weeks | HUMAN BRAIN HBR | |
|---|---|---|---|---|---|
| NKX2-1 | 0 | 0 | 0 | 0 | |
| LHX6 | 0 | 0 | 0.326 | 6.18 | |
| LHX8 | 0 | 0.223 | 1.628 | 0 | |
| DLX1 | 0 | 3.793 | 4.069 | 8.2 | |
| DLX2 | 0 | 6.916 | 6.998 | 2 | |
| ARX | 0 | 11.602 | 0.326 | 3.68 | |
| DLX5 | 0 | 0.446 | 3.418 | 1.25 | |
| DLX6 | 0 | 0.977 | 1.3 | 1.3 | |
| GSX1 | 0 | 0 | 0.163 | 0 | |
| GSX2 | 0 | 0.223 | 0.977 | 0.25 | |
| ASCL1 | 0 | 5.578 | 7.975 | 6.6 | Mash1 |
| HMX3 | 0 | 0.223 | 0.163 | 0 | Nkx5.1 |
| HTR3A | 0 | 0.223 | 0 | 0.18 | |
| SST | 131.14 | 37.929 | 158.36 | 73 | |
| PVALB | 3.974 | 0.223 | 0.488 | 352 | |
| RELN | 119.218 | 53.323 | 29.133 | 57 | |

| | ORGANOIDS 1 week | 4 weeks | 12 weeks | HUMAN BRAIN HBR |
|---|---|---|---|---|
| FGF4 | 0 | 0 | 0 | 0 |
| FGF8 | 0 | 41.72 | 3.418 | 0.3 |
| SHH | 0 | 0.892 | 0.488 | 0.75 |
| NKX2-2 | 0 | 0 | 0.488 | 16 |
| NKX6-1 | 3.974 | 0 | 1.3 | 0.6 |
| LMX1B | 0 | 0 | 0.326 | 0.06 |
| INSM1 | 11.922 | 66.48 | 55.17 | 12.37 |
| GATA2 | 0 | 4.46 | 3.092 | 1.8 |
| ASCL1 | 0 | 5.578 | 7.975 | 6.6 |
| GATA3 | 87.427 | 0 | 10.254 | 0.125 |

DOI:10.1111/j.1460-9568.2011.07910.x

Cells of the Central Nervous System

| | ORGANOID 1 week | ORGANOID 4 weeks | ORGANOID 12 weeks | HUMAN BRAIN HBR |
|---|---|---|---|---|
| **ASTROCYTES** | | | | |
| GFAP | 0 | 0 | 17.089 | 2922 |
| OLIGODENDROCYTES | | | | |
| **OLIG2** | 0 | 6.247 | 1.79 | 20 |
| **MBP** | 0 | 0 | 6.998 | 9 |
| **MICROGLIA** | | | | |
| **AIF1** | 3.974 | 0 | 10.905 | 9 |
| **CD4** | 0 | 0 | 6.998 | 5.3 |
| **VASCULATURE** | | | | |
| **NOS3** | 0 | 0.446 | 0.326 | 4.3 |
| **EDN3** | 0 | 0 | 0.163 | 0.3 |

FIG. 15

| Gene | 1 Week | Weeks | 12 Week |
|---|---|---|---|
| AOC2 | 0 | 0.892 | 6.998 |
| GUCY2D | 0 | 0 | 3.743 |
| GUCY2F | 0 | 2.454 | 0 |
| RAX | 0 | 180.496 | 25.39 |
| RS1 | 0 | 0 | 3.092 |
| CRX | 3.974 | 0.446 | 6.836 |
| RP1 | 0 | 1.116 | 2.441 |
| RPGR | 11.922 | 12.717 | 20.019 |
| PDC | 0 | 0 | 28.97 |
| PDE6B | 0 | 1.785 | 3.418 |
| RD3 | 0 | 3.57 | 7.649 |
| VSX1 | 0 | 21.195 | 3.743 |

FIG. 16

| Gene | 1 week | 4 week | 12 week |
|---|---|---|---|
| TNC | 15.896 | 0.892 | 99.117 |
| PTPRZ1 | 47.687 | 85.674 | 52.732 |
| FAM107A | 0 | 27.443 | 7.649 |
| HOPX | 0 | 0 | 0.651 |
| ITGB5 | 51.661 | 14.056 | 63.8 |
| FOXP2 | 71.531 | 63.81 | 27.18 |
| THBS1 | 3.974 | 15.841 | 39.224 |
| CNTN4 | 0 | 15.618 | 25.227 |
| VSTM2L | 3.974 | 0.446 | 7.812 |
| CPNE8 | 59.609 | 1.785 | 14.648 |
| TBR1 | 11.922 | 0.223 | 0.326 |

| AUTISM ASSOCIATED GENES | | | | | CHANGE | COMMENTS |
|---|---|---|---|---|---|---|
| Gene | TSC2 | TSC2 | WT | WT | | |
| ADNP | 76.944 | 56.94 | 37.033 | 30.873 | 2 | high confidence |
| POGZ | 144.045 | 156.206 | 211.255 | 251.871 | 1.3 | high confidence |
| ANKRD11 | 44.576 | 60.249 | 93.05 | 103.95 | 2 | strong candidate |
| BCL11A | 15.048 | 11.167 | 31.235 | 29.418 | 2 | strong candidate |
| NRXN1 | 1.136 | 0.827 | 4.302 | 3.015 | 3.5 | strong candidate |
| RELN | 76.944 | 54.183 | 117.551 | 138.877 | 2 | strong candidate |
| HDAC4 | 17.13 | 16.682 | 31.515 | 39.085 | 2 | syndromic |
| DMD | 24.134 | 18.888 | 1.122 | 1.559 | 10 | syndromic |
| PCDH19 | 7.666 | 6.618 | 42.083 | 44.179 | 6 | syndromic |

FIG. 19A

AUTISM ASSOCIATED GENES

| Gene | TSC2 | TSC2 | WT | WT | CHANGE | COMMENTS | |
|---|---|---|---|---|---|---|---|
| ATP1B2 | 10.884 | 8.272 | 43.766 | 41.372 | 4 | Microcephaly | 21q11.2-q22.3-SFARI |
| ADAMTS1 | 52.148 | 78.034 | 279.897 | 226.299 | 4 | Metalloproteinase | 17pter-p13.1-SFARI |
| ADAMTS15 | 33.692 | 47.289 | 138.592 | 294.179 | 4 | Metallopeptidase | 11q24.2-q25-SFARI |
| ABAT | 12.682 | 29.366 | 108.573 | 79.626 | 4 | Catabolism of GABA | 3q13.11-q13.31-SFARI |
| ALCAM | 50.444 | 43.567 | 109.602 | 92.516 | 2 | Activated leukocyte cell adhesion | 16p13.3-p13.12-SFARI |
| AMBP | 2.082 | 6.48 | 16.112 | 15.606 | 4 | Alpha-1-Microglobulin/Bikunin Precursor | 11q12.1-q12.2-SFARI |
| APLNR | 555.263 | 424.223 | 28.429 | 28.17 | 15 | Apelin Receptor | Zn++Deficiency? |
| APOC3 | 9.748 | 24.265 | 496.296 | 259.875 | 20 | Dyslipidemia | 11q22.1-q25-SFARI |
| ARSI | 3.502 | 4.274 | 30.767 | 60.811 | 10 | Arylsulfatase | 5q33.1-q35.3-SFARI |
| ATR7B | 71.455 | 67.142 | 331.799 | 4.5.447 | 5 | Cu++ Transport | 13q11-q34-SFARI |
| CDR1 | 851.208 | 931.168 | 5323.372 | 6246.464 | 6 | Cerebellar Degeneration | Xq27.1-q28-SFARI |
| DHCR7 | 62.274 | 83.273 | 244.454 | 201.871 | 3 | Smith-Lemli-Optiz syndrome | Xq27.1-q28-SFARI |

FIG. 19B

OTHER KNOWN CLINICAL SYMPTOMS

| Gene | TSC2 | TSC2 | WT | WT | CHANGE | COMMENTS |
|---|---|---|---|---|---|---|
| AGT | 2.461 | 16.131 | 106.423 | 77.131 | 8 | Hypertension |
| AGTR1 | 0.473 | 0.276 | 18.142 | 5.509 | 12 | Hypertension |
| ALB | 1.893 | 3.171 | 11.746 | 11.518 | 4 | Zn++Deficiency |
| AMBP | 2.082 | 6.48 | 16.112 | 15.606 | 4 | Kidney failure |
| HBE1 | 0.662 | 1.241 | 393.988 | 438.441 | 400 | Ascariasis/Pb poisioning |
| HGD | 0.379 | 0 | 26.559 | 18.504 | 20 | PARKINSONS/Alkaptonuria |

FIG. 19C

| | AD | AD | WT | WT | CHANGE | | COMMENT |
|---|---|---|---|---|---|---|---|
| A2M | 29.679 | 38.222 | 6.512 | 13.156 | 3.5 | Lipid | alpha2-macroglobulin in late-onset Alzheimer's disease |
| ABCA2 | 41.686 | 62.111 | 36.771 | 28.38 | 2 | Lipid | ABCA2 is a strong genetic risk factor for early-onset Alzheimer's disease |
| ABCA5 | 38.741 | 71.874 | 21.641 | 20.11 | 2.5 | Lipid | ABCA2 is a strong genetic risk factor for early-onset Alzheimer's disease |
| ABTB2 | 20.39 | 26.589 | 5.171 | 5.075 | 4 | NV | Neurovascular dysfunction |
| ASIC2 | 1.359 | 2.7 | 0 | 0.564 | 2 | PH | Acid sensing channel in AD |
| ACSL6 | 2.266 | 3.531 | 0 | 0.564 | 3 | Tau | A novel Alzheimer disease locus located near the gene encoding tau protein |
| ADA | 18.577 | 10.386 | 34.473 | 41.536 | 2 | Adenosine | Adenosine deficiency in AD |
| ADAMTSL4 | 9.515 | 9.348 | 30.643 | 28.756 | 3 | LAOD | Whole-exome sequencing of multiplex families identifies several rare coding variants in known and novel Late-Onset Alzheimer genes |
| AMPL3105 | 14.333 | 27.578 | 28.944 | | | RNA-Edit | RNA Editing Genes Associated with Extreme Old Age in Humans and with Lifespan in C. elegans |
| AIM2 | 7.929 | 15.995 | 1.341 | 0.376 | 12 | Immune | Activation of the inflammasome is a key function mediated by the innate immune system |
| AK5 | 5.211 | 7.063 | 1.341 | 2.631 | 3 | X-Chr | X chromosome aneuploidy in the Alzheimer's disease brain |
| ALCAM | 77.708 | 87.869 | 38.303 | 41.16 | 2 | Immune | Vascular inflammation in central nervous system diseases: adhesion receptors controlling leukocyte-endothelial interactions |
| ALKBH3 | 22.655 | 26.797 | 8.81 | 7.894 | 3 | Epigentic | Epigenetics of Aging and Alzheimer's Disease: |
| ANK2 | 77.255 | 70.628 | 18.96 | 15.787 | 5 | Longevity | The Human Longevity Variants |
| ANK3 | 56.638 | 45.908 | 3.064 | 3.759 | 15 | LAOD | Significant association with late-onset Alzheimer's disease for 4 SNPs |
| ANKS1B | 12.687 | 10.386 | 4.213 | 2.631 | 5 | APP | Interacts with amyloid beta protein precursor |
| APC2 | 28.687 | 37.599 | 13.981 | 6.014 | 4 | Psychosis | Psychosis gene in Alzheimer's |
| ASPM | 44.858 | 43.208 | 143.254 | 104.874 | 3 | Microcep | Microcephaly genes and risk of late onset Alzheimers |
| ATP9A | 33.757 | 28.043 | 12.832 | 14.284 | 2 | g-Secretase | Proton myo-inositol cotransporter is a novel γ-secretase associated protein that regulates Aβ production without affecting Notch cleavage |
| AURKA | 1.812 | 0.415 | 6.512 | 5.6382 | 3 | DOWN | DOWN SYNDROME Gene Network Disruptions and Neurogenesis |
| CD36 | 22.429 | 14.126 | 0.383 | 0.94 | 18 | Immune | Immune Function |
| CD3G | 4.078 | 4.57 | 0.575 | 0 | 4 | Immune | Immune Function |
| CD4 | 4.984 | 3.324 | 0.958 | 1.692 | 4 | Immune | Immune Function |

FIG. 21A

| | AD | AD | WT | WT | CHANGE | | COMMENT |
|---|---|---|---|---|---|---|---|
| CD52 | 0.453 | 0.831 | 4.596 | 7.894 | 6 | Immune | Immune Function |
| EFHD2 | 48.709 | 74.574 | 206.646 | 209.747 | 4 | Tau | EFhd2 is a novel amyloid protein associated with pathological tau in Alzheimer's disease. |
| LRRTM3 | 5.211 | 3.324 | 0.766 | 0.94 | | Tau | LRRTM3 Interacts with APP and BACE1 and Has Variants Associating with Late-Onset Alzheimer's disease. (LOAD) |
| AQP1 | 86.77 | 44.869 | 231.544 | 231.128 | 3 | Water | AQP1 is expressed in the plasma membrane of choroid plexus epithelial cells |
| BET1 | 164.251 | 164.313 | 265.059 | 229.482 | 1.5 | Ad | Genetic Determinants of Cognitive Function and Age-related Brain Changes |
| BMP6 | 2.719 | 3.116 | 1.149 | 0.564 | 3 | Neurogenesis | Elevated Levels of BMP6 Impair Neurogenesis in Alzheimer's Disease |
| BRCA1 | 7.703 | 7.478 | 11.299 | 12.404 | 1.5 | AD | Breast cancer gene BRCA1 may be involved in Alzheimer's Disease |
| C1QB | 87.45 | 44.869 | 0 | 0 | 60 | Immune | Complement (c) proteins, C1qB and C4 phagocytosis in the Alzheimer disease patogenesis |
| C1QC | 38.967 | 15.787 | 0 | 0 | 26 | Immune | Complement (C) proteins, C1qB and C4 |
| C1QL3 | 2.492 | 1.246 | 0.383 | 0 | 2 | Immune | Complement (C) proteins, C1qB and C4 |
| CA2 | 89.262 | 262.776 | 27.004 | 24.621 | 12 | PH | Plasma carbonic anhydrase II protein is elevated in Alzheimer's Disease |
| CD36 | 22.429 | 14.126 | 0.383 | 0.94 | 17 | Immune | CD36, a class B scavenger receptor, is expressed on microglia in Alzheimer's disease brain and can mediate production of reactive oxygen species in response to beta-amyloid fibrils. |
| CD3G | 4.078 | 4.57 | 0.575 | 0 | 4 | Immune | |
| CD4 | 4.984 | 3.324 | 0.958 | 1.692 | 4 | Immune | Women with the Alzheimer's risk marker ApoE4 lose Aβ-specific CD4+ T cells 10-20 years before men |
| CD52 | 0.453 | 0.831 | 4.596 | 7.894 | 6 | Immune | The microglial sensome revealed by direct RNA sequencing |
| COL13A1 | 20.616 | 17.657 | 135.211 | 106.941 | 5 | LAOD | A scan of chromosome 10 identifies a novel locus showing strong association with late-onset Alzheimer disease |
| DSCAM | 12.234 | 23.266 | 2.107 | 0.752 | 15 | Down | Possible compensatory events in adult Down syndrome brain prior to the development of Alzheimer disease neuropathology: targets for nonpharmacological intervention |
| KDM5D | 68.646 | 56.71 | 0.383 | 0 | 60 | Chromatin | UBE1Y and KDM5D are involved in DNA condensation |
| TLR4 | 7.929 | 4.155 | 0.766 | 0.94 | 12 | Immune | Microglial activation is key feature in Alzheimer's Disease |
| NAV2 | 41.459 | 31.99 | 4.979 | 4.511 | 9 | Memory | NAV2 was found to be significantly and consistently associated with all seven episodic memory scores |
| PCDHB18 | 14.499 | 14.333 | 1.724 | 4.511 | 5 | AD | Linked to Alzheimer's Disease |

FIG. 21B

NEURAL ORGANOID COMPOSITION AND METHODS OF USE

CROSS-REFERENCE TO RELATED APPLICATION

This application is a continuation of U.S. patent application Ser. No. 16/068,840, filed Jul. 9, 2018, which is the U.S. National Stage Application, pursuant to 35 U.S.C. § 371, of PCT International Patent Application No. PCT/US2017/013231, filed Jan. 12, 2017, designating the United States and published in English, which claims the benefit of and priority to U.S. Provisional Patent Application No. 62/298,872, filed Feb. 23, 2016 and U.S. Provisional Patent Application No. 62/278,857, filed Jan. 14, 2016, the entire contents of which are incorporated herein by reference in their entirety.

BACKGROUND OF THE INVENTION

Nearly one-third of adults will be affected by neurodevelopmental, neuropsychiatric or neurological disease (e.g., autism, anxiety, mood disorders, neurodegenerative disease) at least once in their life. The cost of brain disease to the US and European economies is estimated to be hundreds of billions of dollars per year. Neuroscience has typically relied on the experimental manipulation of living brains or tissue samples, but scientific progress has been limited by a number of factors. For ethical and technical reasons, most invasive techniques are impossible to use on humans. Experiments in animals are expensive and results obtained in animals must be verified in long and expensive human clinical trials. Improved experimental models of the human brain are urgently required to understand disease mechanisms and test potential therapeutics.

SUMMARY OF THE INVENTION

As described below, the present invention features a neural organoid that recapitulates in vitro most characteristics of the brain (e.g., human), and methods of using this neural organoid to study disease and to identify therapeutic agents for the treatment of neurological diseases and disorders.

In one aspect, the invention features an in vitro generated three-dimensional neural organoid derived from a human induced pluripotent stem cell (hIPSC), the organoid containing a first region expressing retinal or cortical markers and one or more additional neural regions, each expressing markers of the brain stem, cerebellum, and/or spinal cord. In one embodiment, the organoid comprises a cell expressing one or more neural markers and a cell expressing an astrocytic marker, oligodendrocyte marker, microglia marker, and/or vascular marker. In another embodiment, the hIPSC comprises a genetic mutation associated with a neurological defect. In another embodiment, the genetic mutation is in TSC1, TSC2, PSEN1, or APP.

In one aspect, the invention features an in vitro generated three-dimensional neural organoid derived from human induced pluripotent stem cells, the organoid containing a first cell type expressing neural markers, and a second cell type expressing an astrocytic marker, oligodendrocyte marker, microglia marker, or vascular marker. In one embodiment, the retinal marker is retina specific Guanylate Cyclases (GUY2D, GUY2F), Retina And Anterior Neural Fold Homeobox (RAX), and retina specific Amine Oxidase, Copper Containing 2 (RAX). In another embodiment, the neural marker is a cortical marker that is doublecortin, NeuN, FOXP2, CNTN4, and TBR1. In another embodiment, the neural marker is a marker of dopaminergic neurons selected from the group consisting of tyrosine hydroxylase, vesicular monoamine transporter 2 (VMAT2), dopamine active transporter (DAT) and Dopamine receptor D2 (D2R). In another embodiment, the neural marker is ATOH1, PAX6, SOX2, LHX2, GRID2, or another cerebellar marker. In another embodiment, the neural marker is SOX2, NeuroD1, DCX, EMX2, FOXG1, PROX1, or another granule neuron marker. In another embodiment, the neural marker is FGF8, INSM1, GATA2, ASCL1, GATA3, or another brain stem marker. In another embodiment, the neural marker is a homeobox gene that is HOXA1, A2, A3, B4, A5, C8, or D13. In another embodiment, the neural marker is NKCC1, KCC2, or another GABAergic marker. In another embodiment, the astrocytic marker is GFAP, the oliogodendrocytic marker is OLIG2 or MBP, the microglia marker is AIF1 or CD4, and the vascular marker is NOS3.

In another aspect, the invention features a method for obtaining a neural organoid, the method includes selecting minimally adherent human induced pluripotent stem cells (hIPScs) from a mixed culture of hIPScs and gamma irradiated mouse embryonic fibroblast feeder cells (MEFs), and culturing the IPSCs under conditions that facilitate sphere formation to obtain an embryoid body (EB); transferring the EB to a plate and culture under conditions that induce neuroectodermal differentiation; culturing the EB in a three-dimensional matrix comprising growth factors for about 3-5 days under static conditions; culturing the EB in a three-dimensional matrix under conditions that facilitate the laminar flow of growth media, thereby obtaining a neural organoid.

In another aspect, the invention features a method for obtaining a neural organoid, the method involving culturing iPSCs alone or in the presence of irradiated MEFs; culturing the iPSCs from the previous step under conditions that promote germ layer differentiation in a low-attachment U-bottom plate in the presence of ROCK inhibitor and bFGF for about four days and then culturing the iPSCs in media lacking ROCK inhibitor or bFGF to form; plating the iPSCs from the previous step in a low-attachment plate under conditions that promote neural induction and selecting embryoid bodies displaying neuroectodermal outgrowth from the embryoid body; embedding the selected embryoid body in a 3-dimensional culture matrix and culturing under conditions that promote neural organoid development while gently oscillating the culture 2-3 times daily; and statically culturing the neural organoid.

In various embodiments of the above-aspects, beta mercaptoethanol is stored under conditions that minimize oxidation is added to the culture media at each step in the method. In other embodiments, the culture is gently oscillated for about 1-5 (e.g., 1, 2, 3, 4, 5) minutes twice daily to induce slow laminar flow of media within the culture. In other embodiments, the amount of 3-dimensional culture matrix is optimized to sequester morphogens and growth factor while permitting exchange of nutrients and gases. In another embodiment, the embryoid body is embedded in about 10, 20, or 30 μl of 3-dimensional culture matrix. In other embodiment, the hIPSCs are selected by allowing the MEFs to adhere to a substrate, then removing the non-adherent hIPSCs. In other embodiment, the three-dimensional matrix is a solubilized basement membrane preparation extracted from the Engelbreth-Holm-Swarm (EHS) sarcoma cells.

In another aspect, the invention features an in vitro derived neural organoid generated according to any previous aspect, wherein the organoid comprises a first region expressing retinal or cortical markers and one or more additional regions expressing markers of the midbrain, brain stem, cerebellum, and/or spinal cord.

Compositions and articles defined by the invention were isolated or otherwise manufactured. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "amyloid precursor protein" is meant a protein having at least about 85% identity to NCBI Ref Seq. NP_001129488 or a fragment thereof, which is associated with Alzheimer's disease. In one embodiment, an APP sequence is duplicated in Alzheimer's disease. An exemplary APP sequence is provided below:

```
  1 mdqledllvl finyvptdgn agllaepqia mfcgrlnmhm nvqngkwdsd psgtktcidt
 61 kegilqycqe vypelqitnv veanqpvtiq nwckrgrkqc kthphfvipy rclvgefvsd
121 allvpdkckf lhqermdvce thlhwhtvak etcsekstnl hdygmllpcg idkfrgvefv
181 ccplaeesdn vdsadaeedd sdvwwggadt dyadgsedkv vevaeeeeva eveeeeaddd
241 eddedgdeve eeaeepyeea terttsiatt tttttesvee vvrevcseqa etgpcramis
301 rwyfdvtegk capffyggcg gnrnnfdtee ycmavcgsai pttaastpda vdkyletpgd
361 enehahfqka kerleakhre rmsqvmrewe eaerqaknlp kadkkaviqh fqekvesleq
421 eaanerqqlv ethmarveam lndrrrlale nyitalqavp prprhvfnml kkyvraeqkd
481 rqhtlkhfeh vrmvdpkkaa qirsqvmthl rviyermnqs lsllynvpav aeeiqdevde
541 llqkeqnysd dvlanmisep risygndalm psltetkttv ellpvngefs lddlqpwhsf
601 gadsvpante nevepvdarp aadrglttrp gsgltnikte eisevkmdae frhdsgyevh
661 hqklvffaed vgsnkgaiig lmvggvviat vivitivmlk kkqytsihhg vvevdaavtp
721 eerhlskmqq ngyenptykf feqmqn
```

By "APP polynucleotide" is meant a nucleic acid molecule encoding an APP protein.

By "organoid" is meant an organized mass of cell types generated in vitro that mirrors at least to some degree the structure, marker expression, or function of a naturally occurring organ.

By "neural marker" is meant any protein or polynucleotide the expression of which is associated with a neural cell fate. Exemplary neural markers include markers associated with the cortex, retina, cerebellum, brain stem, granular neurons, dopaminergic, and GABAergic neurons. Exemplary cerebellar markers include but are not limited to ATOH1, PAX6, SOX2, LHX2, and GRID2. Exemplary markers of dopaminergic neurons include but are not limited to tyrosine hydroxylase, vesicular monoamine transporter 2 (VMAT2), dopamine active transporter (DAT) and Dopamine receptor D2 (D2R). Exemplary cortical markers include, but are not limited to, doublecortin, NeuN, FOXP2, CNTN4, and TBR1. Exemplary retinal markers s include but are not limited to retina specific Guanylate Cyclases (GUY2D, GUY2F), Retina And Anterior Neural Fold Homeobox (RAX), and retina specific Amine Oxidase, Copper Containing 2 (RAX). Exemplary granular neuron markers include, but are not limited to SOX2, NeuroD1, DCX, EMX2, FOXG1, and PROX1. Exemplary brain stem markers include, but are not limited to FGF8, INSM1, GATA2, ASCL1, GATA3. Exemplary spinal cord markers include, but are not limited to homeobox genes including but not limited to HOXA1, A2, A3, B4, A5, C8, or D13. Exemplary GABAergic markers include, but are not limited to NKCC1 or KCC2. Exemplary astrocytic markers include, but are not limited to GFAP. Exemplary oliogodendrocytic markers include, but are not limited to OLIG2 or MBP. Exemplary microglia markers include, but are not limited to AIF1 or CD4. Exemplary vascular markers include, but are not limited to NOS3.

By "TSC1 polypeptide" is meant a protein or fragment thereof having at least 85% amino acid identity to the sequence provided at NCBI Ref: NP_000359.1 that functions in brain development. An exemplary human amino acid sequence is provided below:

1 MAQQANVGEL LAMLDSPMLG VRDDVTAVFK ENLNSDRGPM LVNTLVDYYL ETSSQPALHI

61 LTTLQEPHDK HLLDRINEYV GKAATRLSIL SLLGHVIRLQ PSWKHKLSQA PLLPSLLKCL

121 KMDTDVVVLT TGVLVLITML PMIPQSGKQH LLDFFDIFGR LSSWCLKKPG HVAEVYLVHL

181 HASVYALFHR LYGMYPCNFV SFLRSHYSMK ENLETFEEVV KPMMEHVRIH PELVTGSKDH

241 ELDPRRWKRL ETHDVVIECA KISLDPTEAS YEDGYSVSHQ ISARFPHRSA DVTTSPYADT

301 QNSYGCATST PYSTSRLMLL NMPGQLPQTL SSPSTRLITE PPQATLWSPS MVCGMTTPPT

361 SPGNVPPDLS HPYSKVFGTT AGGKGTPLGT PATSPPPAPL CHSDDYVHIS LPQATVTPPR

421 KEERMDSARP CLHRQHHLLN DRGSEEPPGS KGSVTLSDLP GFLGDLASEE DSIEKDKEEA

481 AISRELSEIT TAEAEPVVPR GGFDSPFYRD SLPGSQRKTH SAASSSQGAS VNPEPLHSSL

541 DKLGPDTPKQ AFTPIDLPCG SADESPAGDR ECQTSLETSI FTPSPCKIPP PTRVGFGSGQ

601 PPPYDHLFEV ALPKTAHHFV IRKTEELLKK AKGNTEEDGV PSTSPMEVLD RLIQQGADAH

661 SKELNKLPLP SKSVDWTHFG GSPPSDEIRT LRDQLLLLHN QLLYERFKRQ QHALRNRRLL

721 RKVIKAAALE EHNAAMKDQL KLQEKDIQMW KVSLQKEQAR YNQLQEQRDT MVTKLHSQIR

781 QLQHDREEFY NQSQELQTKL EDCRNMIAEL RIELKKANNK VCHTELLLSQ VSQKLSNSES

841 VQQQMEFLNR QLLVLGEVNE LYLEQLQNKH SDTTKEVEMM KAAYRKELEK NRSHVLQQTQ

901 RLDTSQKRIL ELESHLAKKD HLLLEQKKYL EDVKLQARGQ LQAAESRYEA QKRITQVFEL

961 EILDLYGRLE KDGLLKKLEE EKAEAAEAAE ERLDCCNDGC SDSMVGHNEE ASGHNGETKT

1021 PRPSSARGSS GSRGGGGSSS SSSELSTPEK PPHQRAGPFS SRWETTMGEA SASIPTTVGS

1081 LPSSKSFLGM KARELFRNKS ESQCDEDGMT SSLSESLKTE LGKDLGVEAK IPLNLDGPHP

1141 SPPTPDSVGQ LHIMDYNETH HEHS"

By "TSC1 polynucleotide" is meant any nucleic acid sequence encoding an TSC1 polypeptide or fragment thereof. An exemplary human TSC1 nucleic acid sequence is provided at NCBI Ref NM_000368

1 acgacggggg aggtgctgta cgtccaagat ggcggcgccc tgtaggctgg agggactgtg 61 aggtaaacag ctgaggggga ggagacggtg gtgaccatga aagacaccag gttgacagca 121 ctggaaactg aagtaccagt tgtcgctaga acagtttggt agtggcccca atgaagaacc 181 ttcagaacct gtagcacacg tcctggagcc agcacagcgc cttcgagcga gagaatggcc 241 caacaagcaa atgtcgggga gcttcttgcc atgctggact cccccatgct gggtgtgcgg 301 gacgacgtga cagctgtctt taaagagaac ctcaattctg accgtggccc tatgcttgta 361 aacaccttgg tggattatta cctggaaacc agctctcagc cggcattgca catcctgacc 421 accttgcaag agccacatga caagcacctc ttggacagga ttaacgaata tgtgggcaaa 481 gccgccactc gtttatccat cctctcgtta ctgggtcatg tcataagact gcagccatct 541 tggaagcata agctctctca agcacctctt ttgccttctt tactaaaatg tctcaagatg 601 gacactgacg tcgttgtcct cacaacaggc gtcttggtgt tgataaccat gctaccaatg 661 attccacagt ctgggaaaca gcatcttctt gatttctttg acatttttgg ccgtctgtca 721 tcatggtgcc tgaagaaacc aggccacgtg gcggaagtct atctcgtcca tctccatgcc 781 agtgtgtacg cactctttca tcgcctttat ggaatgtacc cttgcaactt cgtctccttt 841 ttgcgttctc attacagtat gaaagaaaac ctggagactt ttgaagaagt ggtcaagcca 901 atgatggagc atgtgcgaat tcatccggaa ttagtgactg gatccaagga ccatgaactg 961 gaccctcgaa ggtggaagag attagaaact catgatgttg tgatcgagtg tgccaaaatc -continued 1021 tctctggatc ccacagaagc ctcatatgaa gatggctatt ctgtgtctca ccaaatctca 1081 gcccgctttc ctcatcgttc agccgatgtc accaccagcc cttatgctga cacacagaat 1141 agctatgggt gtgctacttc taccccttac tccacgtctc ggctgatgtt gttaaatatg 1201 ccagggcagc tacctcagac tctgagttcc ccatcgacac ggctgataac tgaaccacca 1261 caagctactc tttggagccc atctatggtt tgtggtatga ccactcctcc aacttctcct 1321 ggaaatgtcc cacctgatct gtcacaccct tacagtaaag tctttggtac aactgcaggt 1381 ggaaaaggaa ctcctctggg aaccccagca acctctcctc ctccagcccc actctgtcat 1441 tcggatgact acgtgcacat ttcactcccc caggccacag tcacaccccc caggaaggaa 1501 gagagaatgg attctgcaag accatgtcta cacagacaac accatcttct gaatgacaga 1561 ggatcagaag agccacctgg cagcaaaggt tctgtcactc taagtgatct tccagggttt 1621 ttaggtgatc tggcctctga agaagatagt attgaaaaag ataaagaaga agctgcaata 1681 tctagagaac tttctgagat caccacagca gaggcagagc ctgtggttcc tcgaggaggc 1741 tttgactctc ccttttaccg agacagtctc ccaggttctc agcggaagac ccactcggca 1801 gcctccagtt ctcagggcgc cagcgtgaac cctgagcctt tacactcctc cctggacaag 1861 cttgggcctg acacaccaaa gcaagccttt actcccatag acctgccctg cggcagtgct 1921 gatgaaagcc ctgcgggaga cagggaatgc cagacttctt tggagaccag tatcttcact 1981 cccagtcctt gtaaaattcc acctccgacg agagtgggct ttggaagcgg gcagcctccc 2041 ccgtatgatc atctttttga ggtggcattg ccaaagacag cccatcattt tgtcatcagg 2101 aagactgagg agctgttaaa gaaagcaaaa ggaaacacag aggaagatgg tgtgccctct 2161 acctccccaa tggaagtgct ggacagactg atacagcagg gagcagacgc gcacagcaag 2221 gagctgaaca agttgccttt acccagcaag tctgtcgact ggacccactt tggaggctct 2281 cctccttcag atgagatccg caccctccga gaccagttgc ttttactgca caaccagtta 2341 ctctatgagc gttttaagag gcagcagcat gccctccgga acaggcggct cctccgcaag 2401 gtgatcaaag cagcagctct ggaggaacat aatgctgcca tgaaagatca gttgaagtta 2461 caagagaagg acatccagat gtggaaggtt agtctgcaga aagaacaagc tagatacaat 2521 cagctccagg agcagcgtga cactatggta accaagctcc acagccagat cagacagctg 2581 cagcatgacc gagaggaatt ctacaaccag agccaggaat tacagacgaa gctggaggac 2641 tgcaggaaca tgattgcgga gctgcggata gaactgaaga aggccaacaa caaggtgtgt 2701 cacactgagc tgctgctcag tcaggtttcc caaaagctct caaacagtga gtcggtccag 2761 cagcagatgg agttcttgaa caggcagctg ttggttcttg gggaggtcaa cgagctctat 2821 ttggaacaac tgcagaacaa gcactcagat accacaaagg aagtagaaat gatgaaagcc 2881 gcctatcgga aagagctaga aaaaaacaga agccatgttc tccagcagac tcagaggctt 2941 gatacctccc aaaaacggat tttggaactg gaatctcacc tggccaagaa agaccacctt 3001 cttttggaac agaagaaata tctagaggat gtcaaactcc aggcaagagg acagctgcag 3061 gccgcagaga gcaggtatga ggctcagaaa aggataaccc aggtgtttga attggagatc 3121 ttagatttat atggcaggtt ggagaaagat ggcctcctga aaaaacttga agaagaaaaa 3181 gcagaagcag ctgaagcagc agaagaaagg cttgactgtt gtaatgacgg gtgctcagat 3241 tccatggtag ggcacaatga agaggcatct ggccacaacg gtgagaccaa gacccccagg 3301 cccagcagcg cccggggcag tagtggaagc agaggtggtg gaggcagcag cagcagcagc 3361 agcgagcttt ctaccccaga gaaaccccca caccagaggg caggcccatt cagcagtcgg -continued

```
3421 tgggagacga ctatgggaga agcgtctgcc agcatcccca ccactgtggg ctcacttccc
3481 agttcaaaaa gcttcctggg tatgaaggct cgagagttat ttcgtaataa gagcgagagc
3541 cagtgtgatg aggacggcat gaccagtagc ctttctgaga gcctaaagac agaactgggc
3601 aaagacttgg gtgtggaagc caagattccc ctgaacctag atggccctca cccgtctccc
3661 ccgaccccgg acagtgttgg acagctacat atcatggact acaatgagac tcatcatgaa
3721 cacagctaag gaatgatggt caatcagtgt taacttgcat attgttggca cagaacagga
3781 ggtgtgaatg cacgtttcaa agctttcctg tttccagggt ctgagtgcaa gttcatgtgt
3841 ggaaatggga cggaggtcct ttggacagct gactgaatgc agaacggttt ttggatctgg
3901 cattgaaatg cctcttgacc ttcccctcca cccgccctaa ccccctctca tttacctcgc
3961 agtgtgttct aatccaaggg ccagttggtg ttcctcagta gctttacttt cttcctttcc
4021 cccccaaatg gttgcgtcct ttgaacctgt gcaatatgag gccaaattta atctttgagt
4081 ctaacacacc actttctgct ttcccgaagt tcagataact gggttggctc tcaattagac
4141 caggtagttt gttgcattgc aggtaagtct ggttttgtcc cttccaggag gacatagcct
4201 gcaaagctgg ttgtctttac atgaaagcgt ttacatgaga ctttccgact gctttttga
4261 ttctgaagtt cagcatctaa agcagcaggt ctagaagaac aacggtttat tcatacttgc
4321 attcttttgg cagttctgat aagcttccta gaaagttctg tgtaaacaga agcctgtttc
4381 agaaatctgg agctggcact gtggagacca cacacccttt gggaaagctc ttgtctcttc
4441 ttcccccact acctcttatt tatttggtgt ttgcttgaat gctggtacta ttgtgaccac
4501 aggctggtgt gtaggtggta aaacctgttc tccataggag ggaaggagca gtcactggga
4561 gaggttaccc gagaagcact tgagcatgag gaactgcacc tttaggccat ctcagcttgc
4621 tgggcctttt gttaaaccct tctgtctact ggcctccctt tgtgtgcata cgcctcttgt
4681 tcatgtcagc ttatatgtga cactgcagca gaaaggctct gaaggtccaa agagtttctg
4741 caaagtgtat gtgaccatca tttcccaggc cattagggtt gcctcactgt agcaggttct
4801 aggctaccag aagaggggca gctttttcat accaattcca actttcaggg gctgactctc
4861 cagggagctg atgtcatcac actctccatg ttagtaatgg cagagcagtc taaacagagt
4921 ccgggagaat gctggcaaag gctggctgtg tatacccact aggctgcccc acgtgctccc
4981 gagagatgac actagtcaga aaattggcag tggcagagaa tccaaactca acaagtgctc
5041 ctgaaagaaa cgctagaagc ctaagaactg tggtctggtg ttccagctga ggcaggggga
5101 tttggtagga aggagccagt gaacttggct ttcctgtttc tatctttcat taaaaagaat
5161 agaaggattc agtcataaag aggtaaaaaa ctgtcacggt acgaaatctt agtgcccacg
5221 gaggcctcga gcagagagaa tgaaagtctt tttttttttt ttttttttt agcatggcaa
5281 taaatattct agcatcccta actaaagggg actagacagt tagagactct gtcaccctag
5341 ctataccagc agaaaacctg ttcaggcagg ctttctgggt gtgactgatt cccagcctgt
5401 ggcagggcgt ggtcccaact actcagccta gcacaggctg gcagttggta ctgaattgtc
5461 agatgtggag tattagtgac accacacatt taattcagct ttgtccaaag gaaagcttaa
5521 aacccaatac agtctagttt cctggttccg ttttagaaaa ggaaaacgtg aacaaactta
5581 gaaagggaag gaaatcccat cagtgaatcc tgaaactggt tttaagtgct ttccttctcc
5641 tcatgcccaa gagatctgtg ccatagaaca agataccagg cacttaaagc cttttcctga
5701 attggaaagg aaaagaggcc caagtgcaaa agaaaaaaca ttttagaaac ggacagctta
5761 taaaaataaa gggaagaaag gaggcagcat ggagagaggc ctgtgctaga agctccatgg
5821 acgtgtctgc acagggtcct cagctcatcc atgcggcctg ggtgtccttt tactcagctt
```

-continued 5881 tataacaaat gtggctccaa gctcaggtgc ctttgagttc taggaggctg tgggttttat 5941 tcaactacgg ttgggagaat gagacctgga gtcatgttga aggtgcccaa cctaaaaatg 6001 taggctttca tgttgcaaag aactccagag tcagtagtta ggtttggttt ggttttggac 6061 atgataaacc tgccaagagt caacaggtca cttgatcatg ctgcagtggg tagttctaag 6121 gatggaaagg tgacagtatt actctcgaga ggcaattcag tcctgggcaa aggtattagt 6181 acaataagcg ttaagggcag agtctacctt gaaaccaatt aagcagcttg gtattcataa 6241 atattgggat tggatggcct ccatccagaa atcactatgg gtgagcatac ctgtctcagc 6301 tgtttggcca atgtgcataa cctactcgga tccccacctg acactaacca gagtcagcac 6361 aggccccgag gagcccgaag tctgctgctg tgcagcatgg aattccttta aaaaggtgca 6421 ctacagtttt agcggggagg gggataggaa gacgcagagc aaatgagctc cggagtccct 6481 gcaggtgaat aaacacacag atctgcatct gatagaactt tgatggattt tcaaaaagcc 6541 gttgacaagg ctctgctata cagtctataa aaattgttat tatgggattg gaagaaacac 6601 gtggtcatga atagaaaaaa aacaaaccca aaggtaggaa ggtcaaggtc atttcttaga 6661 tggagaagtt gtgaaagatg tccttggaga tgagttttag gaccagcatt actaaggcag 6721 gtgggcagac agtgacctct ctaggtgtgt ccacagagtt tttcaggaga gaaaactgcc 6781 tgacctttgg gactaagctg cggaatcttc ttactaagct tgaagagtgg agaggcgaga 6841 ggtgagctac tttgtgagcc aaagcttatg tgacatggtt ggggaaacag tccaaactgt 6901 tctgagaagg tgaactgtta cgacccagga caattagaaa aattcaccca ccatgccgca 6961 cattactggg taaaagcagg gcagcaggga acaaaactcc agactcttgg gccgtcccca 7021 tttgcaacag cacacatagt ttctggtata tttgttggga aagataaaac tctagcagtt 7081 gttgagggga ggatgtataa aatggtcatg gggatgaaag gatctctgag accacagagg 7141 ctcagactca ctgttaagaa tagaaaactg ggtatgcgtt tcatgtagcc agcagaactg 7201 aagtgtgctg tgacaagcca atgtgaattt ctaccaaata gtagagcata ccacttgaag 7261 aaggaaagaa ccgaagagca aacaaaagtt ctgcgtaatg agactcacct tttctcgctg 7321 aaagcactaa gaggtgggag gaggcctgca caggctggag gagggtttgg gcagagcgaa 7381 gacccggcca ggaccttggt gagatggggt gccgcccacc tcctgcggat actcttggag 7441 agttgttccc ccagggggct ctgccccacc tggagaagga agctgcctgg tgtggagtga 7501 ctcaaatcag tatacctatc tgctgcacct tcactctcca gggtacatgc tttaaaaccg 7561 acccgcaaca agtattggaa aaatgtatcc agtctgaaga tgtttgtgta tctgtttaca 7621 tccagagttc tgtgacacat gccccccaga ttgctgcaaa gatcccaagg cattgattgc 7681 acttgattaa gcttttgtct gtaggtgaaa gaacaagttt aggtcgagga ctggccccta 7741 ggctgctgct gtgacccttg tcccatgtgg cttgtttgcc tgtccgggac tcttcgatgt 7801 gcccagggga gcgtgttcct gtctcttcca tgccgtcctg cagtccttat ctgctcgcct 7861 gagggaagag tagctgtagc tacaagggaa gcctgcctgg aagagccgag cacctgtgcc 7921 catggcttct ggtcatgaaa cgagttaatg atggcagagg agcttcctcc ccacttcgca 7981 gcgccacatt atccatcctc tgagataagt aggctggttt aaccattgga atggaccttt 8041 cagtggaaac cctgagagtc tgagaacccc cagaccaacc cttccctccc tttccccacc 8101 tcttacagtg tttggacagg agggtatggt gctgctctgt gtagcaagta ctttggctta 8161 tgaaagaggc agccacgcat tttgcactag gaagaatcag taatcacttt tcagaagact 8221 tctatggacc acaaatatat tacggaggaa cagattttgc taagacataa tctagtttta -continued

```
8281 taactcaatc atgaatgaac catgtgtggc aaacttgcag tttaaagggg tcccatcagt
8341 gaaagaaact gatttttttt aacggactgc ttttagttaa attgaagaaa gtcagctctt
8401 gtcaaaaggt ctaaactttc ccgcctcaat cctaaaagca tgtcaacaat ccacatcaga
8461 tgccataaat atgaactgca ggataaaatg gtacaatctt agtgaatggg aattggaatc
8521 aaaagagttt gctgtccttc ttagaatgtt ctaaaatgtc aaggcagttg cttgtgttta
8581 actgtgaaca aataaaaatt tattgttttg cactacaaaa aaaaaa
```

By "TSC2 polypeptide" is meant a protein or fragment thereof having at least 85% amino acid sequence identity to the sequence provided at NCBI Ref: NP_000539.2 that functions in brain development. An exemplary human amino acid sequence is provided below:

```
   1 MAKPTSKDSG LKEKFKILLG LGTPRPNPRS AEGKQTEFII TAEILRELSM ECGLNNRIRM
  61 IGQICEVAKT KKFEEHAVEA LWKAVADLLQ PERPLEARHA VLALLKAIVQ GQGERLGVLR
 121 ALFFKVIKDY PSNEDLHERL EVFKALTDNG RHITYLEEEL ADFVLQWMDV GLSSEFLLVL
 181 VNLVKFNSCY LDEYIARMVQ MICLLCVRTA SSVDIEVSLQ VLDAVVCYNC LPAESLPLFI
 241 VTLCRTINVK ELCEPCWKLM RNLLGTHLGH SAIYNMCHLM EDRAYMEDAP LLRGAVFEVG
 301 MALWGAHRLY SLRNSPTSVL PSFYQAMACP NEVVSYEIVL SITRLIKKYR KELQVVAWDI
 361 LLNIIERLLQ QLQTLDSPEL RTIVHDLLTT VEELCDQNEF HGSQERYFEL VERCADQRPE
 421 SSLLNLISYR AQSIHPAKDG WIQNLQALME RFFRSESRGA VRIKVLDVLS FVLLINRQFY
 481 EEELINSVVI SQLSHIPEDK DHQVRKLATQ LLVDLAEGCH THHFNSLLDI IEKVMARSLS
 541 PPPELEERDV AAYSASLEDV KTAVLGLLVI LQTKLYTLPA SHATRVYEML VSHIQLHYKH
 601 SYTLPIASSI RLQAFDFLLL LRADSLHRLG LPNKDGVVRF SPYCVCDYME PERGSEKKTS
 661 GPLSPPTGPP GPAPAGPAVR LGSVPYSLLF RVLLQCLKQE SDWKVLKLVL GRLPESLRYK
 721 VLIFTSPCSV DQLCSALCSM LSGPKTLERL RGAPEGFSRT DLHLAVVPVL TALISYHNYL
 781 DKTKQREMVY CLEQGLIHRC ASQCVVALSI CSVEMPDIII KALPVLVVKL THISATASMA
 841 VPLLEFLSTL ARLPHLYRNF AAEQYASVFA ISLPYTNPSK FNQYIVCLAH HVIAMWFIRC
 901 RLPFRKDFVP FITKGLRSNV LLSFDDTPEK DSFRARSTSL NERPKSLRIA RPPKQGLNNS
 961 PPVKEFKESS AAEAFRCRSI SVSEHVVRSR IQTSLTSASL GSADENSVAQ ADDSLKNLHL
1021 ELTETCLDMM ARYVFSNFTA VPKRSPVGEF LLAGGRTKTW LVGNKLVTVT TSVGTGTRSL
1081 LGLDSGELQS GPESSSSPGV HVRQTKEAPA KLESQAGQQV SRGARDRVRS MSGGHGLRVG
1141 ALDVPASQFL GSATSPGPRT APAAKPEKAS AGTRVPVQEK TNLAAYVPLL TQGWAEILVR
1201 RPTGNTSWLM SLENPLSPFS SDINNMPLQE LSNALMAAER FKEHRDTALY KSLSVPAAST
1261 AKPPPLPRSN TVASFSSLYQ SSCQGQLHRS VSWADSAVVM EEGSPGEVPV LVEPPGLEDV
1321 KAALGMDRRT DAYSRSSSVS SQEEKSLHAE ELVGRGIPIE RVVSSEGGRP SVDLSFQPSQ
1381 PLSKSSSSPE LQTLQDILGD PGDKADVGRL SPEVKARSQS GTLDGESAAW SASGEDSRGQ
1441 PEGPLPSSSP RSPSGLRPRG YTISDSAPSR RGKRVERDAL KSRATASNAE KVPGINPSFV
1501 FLQLYHSPFF GDESNKPILL PNESQSFERS VQLLDQIPSY DTHKIAVLYV GEGQSNSELA
1561 ILSNEHGSYR YTEFLTGLGR LIELKDCQPD KVYLGGLDVC GEDGQFTYCW HDDIMQAVFH
1621 IATLMPTKDV DKHRCDKKRH LGNDFVSIVY NDSGEDFKLG TIKGQFNFVH VIVTPLDYEC
1681 NLVSLQCRKD MEGLVDTSVA KIVSDRNLPF VARQMALHAN MASQVHHSRS NPTDIYPSKW
1741 IARLRHIKRL RQRICEEAAY SNPSLPLVHP PSHSKAPAQT PAEPTPGYEV GQRKRLISSV
1801 EDFTEFV
```

In one embodiment, a TSC2 polypeptide comprises a mutation affecting brain development. In another embodiment, a TSC2 polypeptide comprises ARG1743GLN where the Arginine in the 1743rd position from the N-terminal is replaced by a Glutamine. ARG1743GLN may also be termed as R1743Q.

By "TSC2 polynucleotide" is meant any nucleic acid sequence encoding a TSC2 polypeptide or fragment thereof. An exemplary human TSC2 nucleic acid sequence is provided at NCBI Ref NM_000548:

```
   1 tttccgccag agggcggcac agaactacaa ctcccagcaa gctcccaagg cggccctccg
  61 cgcaatgccg ctaccggaag tgcgggtcgc gcttccggcg gcgtcccggg gccagggggg
 121 tgcgcctttc tccgcgtcgg ggcggcccgg agcgcggtgg cgcggcgcgg gaggggtttt
 181 ctggtgcgtc ctggtccacc atggccaaac caacaagcaa agattcaggc ttgaaggaga
 241 agtttaagat tctgttggga ctgggaacac cgaggccaaa tcccaggtct gcagagggta
 301 aacagacgga gtttatcatc accgcggaaa tactgagaga actgagcatg gaatgtggcc
 361 tcaacaatcg catccggatg atagggcaga tttgtgaagt cgcaaaaacc aagaaatttg
 421 aagagcacgc agtggaagca ctctggaagg cggtcgcgga tctgttgcag ccggagcggc
 481 cgctggaggc ccggcacgcg gtgctggctc tgctgaaggc catcgtgcag gggcagggcg
 541 agcgtttggg ggtcctcaga gccctcttct ttaaggtcat caaggattac ccttccaacg
 601 aagaccttca cgaaaggctg gaggttttca aggccctcac agacaatggg agacacatca
 661 cctacttgga ggaagagctg gctgactttg tcctgcagtg gatggatgtt ggcttgtcct
 721 cggaattcct tctggtgctg gtgaacttgg tcaaattcaa tagctgttac ctcgacgagt
 781 acatcgcaag gatggttcag atgatctgtc tgctgtgcgt ccggaccgcg tcctctgtgg
 841 acatagaggt ctccctgcag gtgctggacg ccgtggtctg ctacaactgc ctgccggctg
 901 agagcctccc gctgttcatc gttaccctct gtcgcaccat caacgtcaag gagctctgcg
 961 agccttgctg gaagctgatg cggaacctcc ttggcaccca cctgggccac agcgccatct
1021 acaacatgtg ccacctcatg gaggacagag cctacatgga ggacgcgccc ctgctgagag
1081 gagccgtgtt ttttgtgggc atggctctct ggggagccca ccggctctat tctctcagga
1141 actcgccgac atctgtgttg ccatcatttt accaggccat ggcatgtccg aacgaggtgg
1201 tgtcctatga gatcgtcctg tccatcacca ggctcatcaa gaagtatagg aaggagctcc
1261 aggtggtggc gtgggacatt ctgctgaaca tcatcgaacg gctccttcag cagctccaga
1321 ccttggacag cccggagctc aggaccatcg tccatgacct gttgaccacg gtggaggagc
1381 tgtgtgacca gaacgagttc cacgggtctc aggagagata ctttgaactg gtggagagat
1441 gtgcggacca gaggcctgag tcctccctcc tgaacctgat ctcctataga gcgcagtcca
1501 tccacccggc caaggacggc tggattcaga acctgcaggc gctgatggag agattcttca
1561 ggagcgagtc ccgaggcgcc gtgcgcatca aggtgctgga cgtgctgtcc tttgtgctgc
1621 tcatcaacag gcagttctat gaggaggagc tgattaactc agtggtcatc tcgcagctct
1681 cccacatccc cgaggataaa gaccaccagg tccgaaagct ggccacccag ttgctggtgg
1741 acctggcaga gggctgccac acacaccact tcaacagcct gctggacatc atcgagaagg
1801 tgatggcccg ctccctctcc ccacccccgg agctggaaga aagggatgtg gccgcatact
1861 cggcctcctt ggaggatgtg aagacagccg tcctggggct tctggtcatc cttcagacca
1921 agctgtacac cctgcctgca agccacgcca cgcgtgtgta tgagatgctg gtcagccaca
1981 ttcagctcca ctacaagcac agctacaccc tgccaatcgc gagcagcatc cggctgcagg
```

-continued 2041 cctttgactt cctgttgctg ctgcgggccg actcactgca ccgcctgggc ctgcccaaca 2101 aggatggagt cgtgcggttc agcccctact gcgtctgcga ctacatggag ccagagagag 2161 gctctgagaa gaagaccagc ggcccccttt ctcctcccac agggcctcct ggcccggcgc 2221 ctgcaggccc cgccgtgcgg ctggggtccg tgccctactc cctgctcttc cgcgtcctgc 2281 tgcagtgctt gaagcaggag tctgactgga aggtgctgaa gctggttctg ggcaggctgc 2341 ctgagtccct gcgctataaa gtgctcatct ttacttcccc ttgcagtgtg gaccagctgt 2401 gctctgctct ctgctccatg ctttcaggcc caaagacact ggagcggctc cgaggcgccc 2461 cagaaggctt ctccagaact gacttgcacc tggccgtggt tccagtgctg acagcattaa 2521 tctcttacca taactacctg gacaaaacca aacagcgcga gatggtctac tgcctggagc 2581 agggcctcat ccaccgctgt gccagccagt gcgtcgtggc cttgtccatc tgcagcgtgg 2641 agatgcctga catcatcatc aaggcgctgc ctgttctggt ggtgaagctc acgcacatct 2701 cagccacagc cagcatggcc gtcccactgc tggagttcct gtccactctg gccaggctgc 2761 cgcacctcta caggaacttt gccgcggagc agtatgccag tgtgttcgcc atctccctgc 2821 cgtacaccaa cccctccaag tttaatcagt acatcgtgtg tctggcccat cacgtcatag 2881 ccatgtggtt catcaggtgc cgcctgccct tccggaagga ttttgtccct ttcatcacta 2941 agggcctgcg gtccaatgtc ctcttgtctt ttgatgacac ccccgagaag gacagcttca 3001 gggcccggag tactagtctc aacgagagac ccaagagtct gaggatagcc agacccccca 3061 aacaaggctt gaataactct ccacccgtga aagaattcaa ggagagctct gcagccgagg 3121 ccttccggtg ccgcagcatc agtgtgtctg aacatgtggt ccgcagcagg atacagacgt 3181 ccctcaccag tgccagcttg gggtctgcag atgagaactc cgtggcccag gctgacgata 3241 gcctgaaaaa cctccacctg gagctcacgg aaacctgtct ggacatgatg gctcgatacg 3301 tcttctccaa cttcacggct gtcccgaaga ggtctcctgt gggcgagttc ctcctagcgg 3361 gtggcaggac caaaacctgg ctggttggga acaagcttgt cactgtgacg acaagcgtgg 3421 gaaccgggac ccggtcgtta ctaggcctgg actcggggga gctgcagtcc ggcccggagt 3481 cgagctccag ccccggggtg catgtgagac agaccaagga ggcgccggcc aagctggagt 3541 cccaggctgg gcagcaggtg tcccgtgggg cccgggatcg ggtccgttcc atgtcggggg 3601 gccatggtct tcgagttggc gccctggacg tgccggcctc ccagttcctg ggcagtgcca 3661 cttctccagg accacggact gcaccagccg cgaaacctga gaaggcctca gctggcaccc 3721 gggttcctgt gcaggagaag acgaacctgg cggcctatgt gcccctgctg acccagggct 3781 gggcggagat cctggtccgg aggcccacag ggaacaccag ctggctgatg agcctggaga 3841 acccgctcag ccctttctcc tcggacatca acaacatgcc cctgcaggag ctgtctaacg 3901 ccctcatggc ggctgagcgc ttcaaggagc accgggacac agccctgtac aagtcactgt 3961 cggtgccggc agccagcacg gccaaacccc ctcctctgcc tcgctccaac acagtggcct 4021 ctttctcctc cctgtaccag tccagctgcc aaggacagct gcacaggagc gtttcctggg 4081 cagactccgc cgtggtcatg gaggagggaa gtccgggcga ggttcctgtg ctggtggagc 4141 ccccagggtt ggaggacgtt gaggcagcgc taggcatgga caggcgcacg gatgcctaca 4201 gcaggtcgtc ctcagtctcc agccaggagg agaagtcgct ccacgcggag gagctggttg 4261 gcaggggcat ccccatcgag cgagtcgtct cctcggaggg tggccggccc tctgtggacc 4321 tctccttcca gccctcgcag cccctgagca agtccagctc ctctcccgag ctgcagactc 4381 tgcaggacat cctcggggac cctggggaca aggccgacgt gggccggctg agccctgagg 4441 ttaaggcccg gtcacagtca gggaccctgg acggggaaag tgctgcctgg tcggcctcgg -continued

```
4501 gcgaagacag tcggggccag cccgagggtc ccttgccttc cagctccccc cgctcgccca
4561 gtggcctccg gccccgaggt tacaccatct ccgactcggc cccatcacgc aggggcaaga
4621 gagtagagag ggacgcctta aagagcagag ccacagcctc caatgcagag aaagtgccag
4681 gcatcaaccc cagtttcgtg ttcctgcagc tctaccattc cccctcttt ggcgacgagt
4741 caaacaagcc aatcctgctg cccaatgagt cacagtcctt tgagcggtcg gtgcagctcc
4801 tcgaccagat cccatcatac gacacccaca agatcgccgt cctgtatgtt ggagaaggcc
4861 agagcaacag cgagctcgcc atcctgtcca atgagcatgg ctcctacagg tacacggagt
4921 tcctgacggg cctgggccgg ctcatcgagc tgaaggactg ccagccggac aaggtgtacc
4981 tgggaggcct ggacgtgtgt ggtgaggacg gccagttcac ctactgctgg cacgatgaca
5041 tcatgcaagc cgtcttccac atcgccaccc tgatgcccac caaggacgtg gacaagcacc
5101 gctgcgacaa gaagcgccac ctgggcaacg actttgtgtc cattgtctac aatgactccg
5161 gtgaggactt caagcttggc accatcaagg gccagttcaa ctttgtccac gtgatcgtca
5221 ccccgctgga ctacgagtgc aacctggtgt ccctgcagtg caggaaagac atggagggcc
5281 ttgtggacac cagcgtggcc aagatcgtgt ctgaccgcaa cctgcccttc gtggcccgcc
5341 agatggccct gcacgcaaat atggcctcac aggtgcatca tagccgctcc aaccccaccg
5401 atatctaccc ctccaagtgg attgcccggc tccgccacat caagcggctc cgccagcgga
5461 tctgcgagga agccgcctac tccaacccca gcctacctct ggtgcaccct ccgtcccata
5521 gcaaagcccc tgcacagact ccagccgagc ccacacctgg ctatgaggtg ggccagcgga
5581 agcgcctcat ctcctcggtg gaggacttca ccgagtttgt gtgaggccgg ggccctccct
5641 cctgcactgg ccttggacgg tattgcctgt cagtgaaata aataaagtcc tgaccccagt
5701 gcacagacat agaggcacag attgcagtca gacaaaaaaa aaaaaaaaaa a
```

By "PSEN1 polypeptide" is meant a protein or fragment thereof having at least 85% amino acid sequence identity to the sequence provided at NCBI Ref: NP_000012.1 having enzymatic activity or functioning in regulating beta amyloid levels. An exemplary human amino acid sequence is provided below:

```
  1 MTELPAPLSY FQNAQMSEDN HLSNTVRSQN DNRERQEHND
    RRSLGHPEPL SNGRPQGNSR

 61 QVVEQDEEED EELTLKYGAK HVIMLFVPVT LCMVVVVATI
    KSVSFYTRKD GQLIYTPFTE

121 DTETVGQRAL HSILNAAIMI SVIVVMTILL VVLYKYRCYK
    VIHAWLIISS LLLLFFFSFI

181 YLGEVFKTYN VAVDYITVAL LIWNFGVVGM ISIHWKGPLR
    LQQAYLIMIS ALMALVFIKY
```

-continued

```
241 LPEWTAWLIL AVISVYDLVA VLCPKGPLRM LVETAQERNE
    TLFPALIYSS TMVWLVNMAE

301 GDPEAQRRVS KNSKYNAEST ERESQDTVAE NDDGGFSEEW
    EAQRDSHLGP HRSTPESRAA

361 VQELSSSILA GEDPEERGVK LGLGDFIFYS VLVGKASATA
    SGDWNTTIAC FVAILIGLCL

421 TLLLLAIFKK ALPALPISIT FGLVFYFATD YLVQPFMDQL
    AFHQFYI
```

In one embodiment, a PSEN1 polypeptide encompasses a mutation (e.g., ALA246GLU). In one embodiment, the PSEN1 polypeptide comprises an Alanine corresponding to the Alanine in the 246th position from the N-terminal in the exemplary PSEN1 polypeptide replaced by a Glutamic acid. ALA246GLU may also be termed as A246E.

By "PSEN1 polynucleotide" is meant any nucleic acid sequence encoding a PSEN1 polypeptide or fragment thereof. An exemplary human PSEN1 nucleic acid sequence is provided at NCBI Ref NM_000021:

```
  1 aaatgacgac aacggtgagg gttctcgggc ggggcctggg acaggcagct ccggggtccg
 61 cggtttcaca tcggaaacaa aacagcggct ggtctggaag gaacctgagc tacgagccgc
121 ggcggcagcg gggcggcggg gaagcgtata cctaatctgg gagcctgcaa gtgacaacag
181 cctttgcggt ccttagacag cttggcctgg aggagaacac atgaaagaaa gaacctcaag
241 aggctttgtt ttctgtgaaa cagtatttct atacagttgc tccaatgaca gagttacctg
```

-continued

```
 301 caccgttgtc ctacttccag aatgcacaga tgtctgagga caaccacctg agcaatactg
 361 tacgtagcca gaatgacaat agagaacggc aggagcacaa cgacagacgg agccttggcc
 421 accctgagcc attatctaat ggacgacccc agggtaactc ccggcaggtg gtggagcaag
 481 atgaggaaga agatgaggag ctgacattga aatatggcgc caagcatgtg atcatgctct
 541 ttgtccctgt gactctctgc atggtggtgg tcgtggctac cattaagtca gtcagctttt
 601 atacccggaa ggatgggcag ctaatctata ccccattcac agaagatacc gagactgtgg
 661 gccagagagc cctgcactca attctgaatg ctgccatcat gatcagtgtc attgttgtca
 721 tgactatcct cctggtggtt ctgtataaat acaggtgcta taaggtcatc catgcctggc
 781 ttattatatc atctctattg ttgctgttct ttttttcatt catttacttg gggggaagtgt
 841 ttaaaaccta taacgttgct gtggactaca ttactgttgc actcctgatc tggaattttg
 901 gtgtggtggg aatgatttcc attcactgga aaggtccact tcgactccag caggcatatc
 961 tcattatgat tagtgccctc atggccctgg tgtttatcaa gtacctccct gaatggactg
1021 cgtggctcat cttggctgtg atttcagtat atgatttagt ggctgttttg tgtccgaaag
1081 gtccacttcg tatgctggtt gaaacagctc aggagagaaa tgaaacgctt tttccagctc
1141 tcatttactc ctcaacaatg gtgtggttgg tgaatatggc agaaggagac ccggaagctc
1201 aaaggagagt atccaaaaat tccaagtata atgcagaaag cacagaaagg gagtcacaag
1261 acactgttgc agagaatgat gatggcgggt tcagtgagga atgggaagcc cagagggaca
1321 gtcatctagg gcctcatcgc tctacacctg agtcacgagc tgctgtccag gaactttcca
1381 gcagtatcct cgctggtgaa gacccagagg aaaggggagt aaaacttgga ttgggagatt
1441 tcattttcta cagtgttctg gttggtaaag cctcagcaac agccagtgga gactggaaca
1501 caaccatagc ctgtttcgta gccatattaa ttggtttgtg ccttacatta ttactccttg
1561 ccattttcaa gaaagcattg ccagctcttc caatctccat cacctttggg cttgttttct
1621 actttgccac agattatctt gtacagcctt ttatggacca attagcattc catcaatttt
1681 atatctagca tatttgcggt tagaatccca tggatgtttc ttctttgact ataacaaaat
1741 ctggggagga caaaggtgat ttttcctgtgt ccacatctaa caaagtcaag attcccggct
1801 ggacttttgc agcttccttc caagtcttcc tgaccacctt gcactattgg actttggaag
1861 gaggtgccta tagaaaacga ttttgaacat acttcatcgc agtggactgt gtccctcggt
1921 gcagaaacta ccagatttga gggacgaggt caaggagata tgataggccc ggaagttgct
1981 gtgccccatc agcagcttga cgcgtggtca caggacgatt tcactgacac tgcgaactct
2041 caggactacc gttaccaaga ggttaggtga agtggtttaa accaaacgga actcttcatc
2101 ttaaactaca cgttgaaaat caacccaata attctgtatt aactgaattc tgaacttttc
2161 aggaggtact gtgaggaaga gcaggcacca gcagcagaat ggggaatgga gaggtgggca
2221 ggggttccag cttccctttg attttttgct gcagactcat ccttttttaaa tgagacttgt
2281 tttcccctct ctttgagtca agtcaaatat gtagattgcc tttggcaatt cttcttctca
2341 agcactgaca ctcattaccg tctgtgattg ccatttcttc ccaaggccag tctgaacctg
2401 aggttgcttt atcctaaaag ttttaacctc aggttccaaa ttcagtaaat tttggaaaca
2461 gtacagctat ttctcatcaa ttctctatca tgttgaagtc aaatttggat tttccaccaa
2521 attctgaatt tgtagacata cttgtacgct cacttgcccc agatgcctcc tctgtcctca
2581 ttcttctctc ccacacaagc agtctttttc tacagccagt aaggcagctc tgtcgtggta
2641 gcagatggtc ccattattct agggtcttac tctttgtatg atgaaaagaa tgtgttatga
```

-continued

```
2701 atcggtgctg tcagccctgc tgtcagacct tcttccacag caaatgagat gtatgcccaa
2761 agacggtaga attaaagaag agtaaaatgg ctgttgaagc actttctgtc ctggtatttt
2821 gtttttgctt ttgccacaca gtagctcaga atttgaacaa atagccaaaa gctggtggtt
2881 gatgaattat gaactagttg tatcaacaca aagcaagagt tggggaaagc catatttaac
2941 ttggtgagct gtgggagaac ctggtggcag aaggagaacc aactgccaag gggaaagaga
3001 aggggcctcc agcagcgaag gggatacagt gagctaatga tgtcaaggag gagtttcagg
3061 ttattctcgt cagctccaca aatgggtgct ttgtggtctc tgcccgcgtt acctttcctc
3121 tcaatgtacc tttgtgtgaa ctgggcagtg gaggtgcctg ctgcagttac catggagttc
3181 aggctctggg cagctcagtc aggcaaaaca cacaaacagc catcagcctg tgtgggctca
3241 gggcacctct ggacaaaggc ttgtggggca taaccttctt taccacagag agcccttagc
3301 tatgctgatc agaccgtaag cgtttatgag aaacttagtt tcctcctgtg gctgaggagg
3361 ggccagcttt ttcttctttt gcctgctgtt ttctctccca atctatgata tgatatgacc
3421 tggtttgggg ctgtctttgg tgtttagaat atttgttttc tgtcccagga tatttcttat
3481 aagaacctaa cttcaagagt agtgtgcgag tactgatctg aatttaaatt aaaattggct
3541 tatattaggc agtcacagac aggaaaaata agagctatgc aaagaaaggg ggatttaaag
3601 tagtaggttc tatcatctca attcattttt ttccatgaaa tcccttcttc caagattcat
3661 tccctctctc agacatgtgc tagcatgggt attatcattg agaaagcaca gctacagcaa
3721 agccacctga atagcaattt gtgattggaa gcattcttga gggatcccta atctagagta
3781 atttatttgt gtaaggatcc caaatgtgtt gcacctttca tgatacattt cttctctgaa
3841 gagggtacgt ggggtgtgtg tatttaaatc catcctatgt attactgatt gtcctgtgta
3901 gaaagatggc aattattctg tctctttctc caagtttgag ccacatctca gccacattgt
3961 tagacagtgt acagagaacc tatctttcct tttttttttt ttaaaggaca ggattttgct
4021 gtgttgccca ggctagactt gaactcctgg gctcaagtaa tccacctcag cctgagtagc
4081 tgagactaca gcccatctta tttctttaaa tcattcatct caggcagaga acttttccct
4141 caaacattct ttttagaatt agttcagtca ttcctaaaac atccaaatgc tagtcttcca
4201 ccatgaaaaa tagattgtca ctggaaagaa cagtagcaat ttccataagg atgtgccttc
4261 actcacacgg gacaggcggt ggttatagag tcgggcaaaa ccagcagtag agtatgacca
4321 gccaagccaa tctgcttaat aaaaagatgg aagacagtaa ggaaggaaag tagccactaa
4381 gagtctgagt ctgactgggc tacagaataa agggtattta tggacagaat gtcattacat
4441 gcctatggga ataccaatca tatttggaag atttgcagat ttttttttcag agaggaaaga
4501 ctcaccttcc tgtttttggt tctcagtagg ttcgtgtgtg ttcctagaat cacagctctg
4561 actccaaatg actcaatttc tcaattagaa aaagtagaag ctttctaagc aacttggaag
4621 aaaacagtca taagtaagca atttgttgat tttactacag aagcaacaac tgaagaggca
4681 gtgtttttac tttcagactc cgggattccc attctgtagt ctctctgctt ttaaaaaccc
4741 tccttttgca atagatgccc aaacagatga tgtttattac ttgttattta cgtggcctca
4801 gacagtgtat gtattctcga tataacttgt agagtgtgaa atataagttt aactaccaaa
4861 taaggtctcc cagggttaga tgactgcggg aagcctttga tcccaacccc caaggctttg
4921 tatatttgat catttgtgat ctaaccctgg aagaaaaaga gctcagaaac cactatgaaa
4981 aaatttgttc agtgttttct gtgttcccgt aggttctgga gtctgaggat gcaaagatga
5041 ataagataaa ttctcagaat gtagttataa tctcttgttt tctggtatat gccatctttc
5101 tttaacttct ctaaaatatt gggtatttgt caaataacca cttttaacag ttaccattac
```

-continued

```
5161 tgagggctta tacattggtg ttataaaagt gacttgattc agaaatcaat ccattcagta

5221 aagtactcct tctctaaatt tgctgttatg tctataagga acagtttgac ctgcccttct

5281 cctcacctcc tcacctgcct tccaacattg aatttggaag gagacgtgaa aattggacat

5341 ttggttttgc ccttgggctg gaaactatca tataatcata agtttgagcc tagaagtgat

5401 ccttgtgatc ttctcacctc tttaaattcc cacaacacaa gagattaaaa acagaggttt

5461 cagctcttca tagtgcgttg tgaaatggct ggccagagtg taccaacaaa gctgtcatcg

5521 ggctcacagc tcagagacat ctgcatgtga tcatctgcat agtcctctcc tctaacggga

5581 aacacctcag atttgcatat aaaaaagcac cctggtgctg aaatgaaccc ctttcttgaa

5641 catcaaagct gtctcccaca gccttgggca gcagggtgcc tcttagtgga tgtgctgggt

5701 ccaccctgag ccctgacatg tggtggcagc attgccagtt ggtctgtgtg tctgtgtagc

5761 agggacgatt tcccagaaag caattttcct tttgaaatac gtaattgttg agactaggca

5821 gtttcaaagt cagctgcata tagtagcaag tacaggactg tcttgttttt ggtgtccttg

5881 gaggtgctgg ggtgagggtt tcagtgggat catttactct cacatgttgt ctgccttctg

5941 cttctgtgga cactgctttg tacttaattc agacagactg tgaatacacc tttttataa

6001 ataccttca aattcttggt aagatataat tttgatagct gattgcagat tttctgtatt

6061 tgtcagatta ataaagactg catgaatcca aaaaaaaaaa aaaaaaa
```

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, a 25% change, a 40% change, or even a 50% or greater change in expression levels."

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include neurological conditions, including tuberous sclerosis or Alzheimer's Disease.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. In one embodiment, the preparation is at least 75%. In other embodiments, at least about 90-99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide analyte having an expression level or activity associated with a particular cell type. In one embodiment, transcriptomics are used to measure the levels of markers associated with cell fate, cell differentiation, and cell specific structure or function.

As used herein, "obtaining" as in "obtaining an agent" includes synthesizing, purchasing, or otherwise acquiring the agent.

By "reference" is meant a standard or control condition.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 5B provides a table showing a representative part of the entire transcriptomic profile of brain organoids in culture for ~12 weeks measured using a transcriptome sequencing approach that is commercially available as AmpliSeq. This technique highlighted the expression of neuronal markers for diverse populations of neurons and other cell types that are comparable to those expressed in an adult human brain reference (HBR) purchased from Clontech and also the publicly available embryonic human brain (BRAINSCAN) atlas of the Allen Institute database.

FIG. DC provides a table showing Ampliseq gene expression data comparing gene expression in an organoid (column 2) after ~12 weeks in culture in vitro versus Human Brain Reference (column 3). A concordance of greater than 98% was observed.

FIG. 5D provides a table showing Ampliseq gene expression data comparing organoids generated during two independent experiments after ~12 weeks in culture (column 2 and 3). Gene expression reproducibility between the two organoids was greater than 99%. Note that values are RPKM (Reads Per Kilo Base per Million reads) in the tables and <1 is background.

Figure 6A:
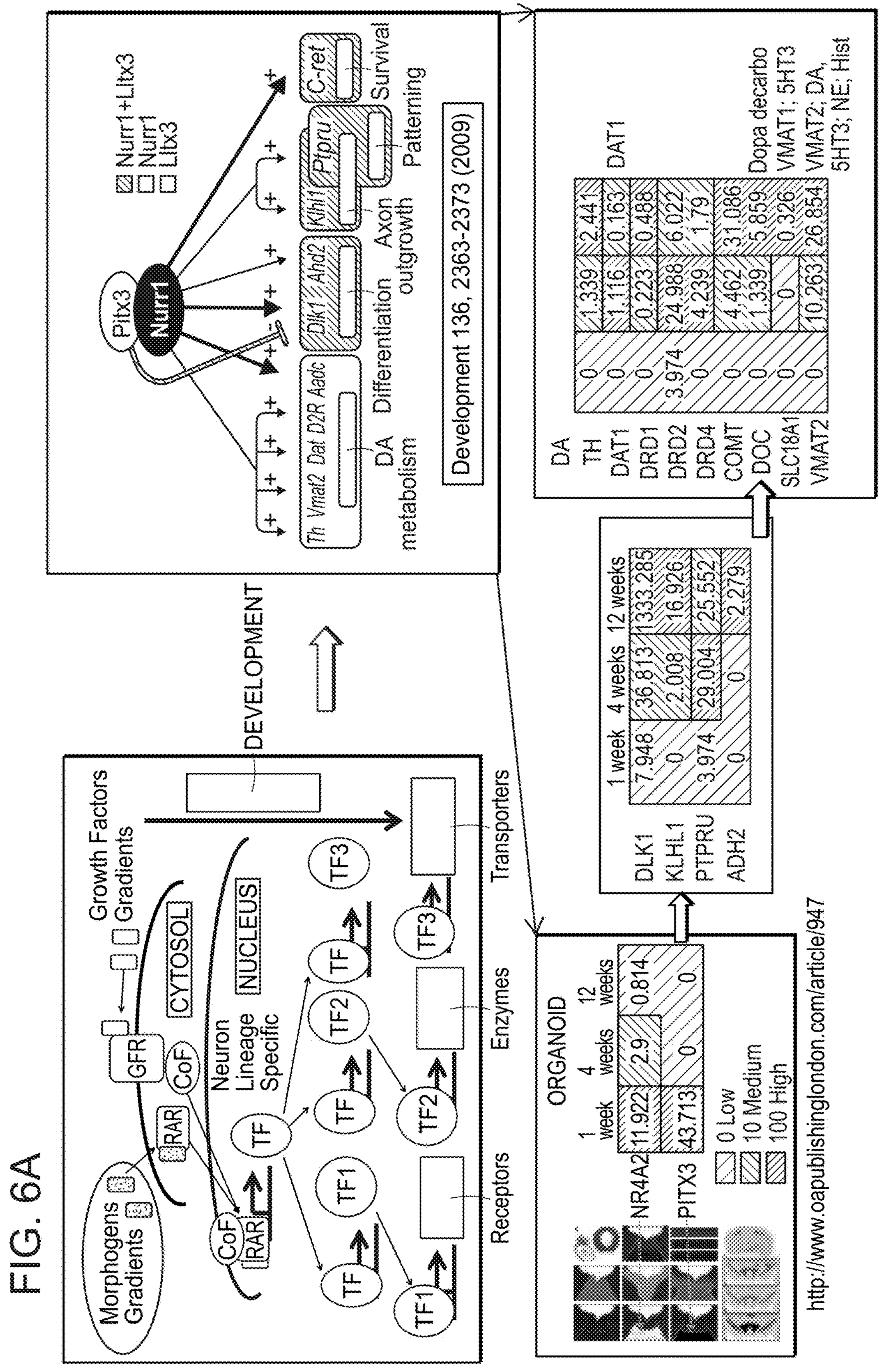

FIG. 6A is a schematic showing results of developmental transcriptomics. Brain organoid development in vitro follows KNOWN Boolean logic for the expression pattern of transcription factors during initiation of developmental programs of the brain. Time Points: 1, 4 and 12 Weeks. PITX3 and NURR1 (NR4A) are transcription factors that initiate midbrain development (early; at week 1), DLK1, KLHL1, PTPRU, and ADH2 respond to these two transcription factors to further promote midbrain development (mid; at week 4 &12), and TH, VMAT2, DAT and D2R define dopamine neuron functions mimicking in vivo development expression patterns. The organoid expresses genes previously known to be involved in the development of dopaminergic neurons (Blaess S, Ang S L. Genetic control of midbrain dopaminergic neuron development. Wiley Interdiscip Rev Dev Biol. 2015 Jan. 6. doi: 10.1002/wdev.169).

FIG. 6B is a table showing Ampliseq gene expression data for genes not expressed in organoid (column 2) and Human Brain Reference (column 3). This data indicates that the organoids generated do not express genes that are characteristic of non-neural tissues. This gene expression concordance is less than 5% for approximately 800 genes that are considered highly enriched or specifically expressed in a non-neural tissue. The olfactory receptor genes expressed in the olfactory epithelium shown are a representative example. Gene expression for most genes in table is zero.

FIG. 6C is a continuation of the table shown in FIG. 6B.

FIG. 6D is a continuation of the table shown in FIG. 6B.

Figure 7:
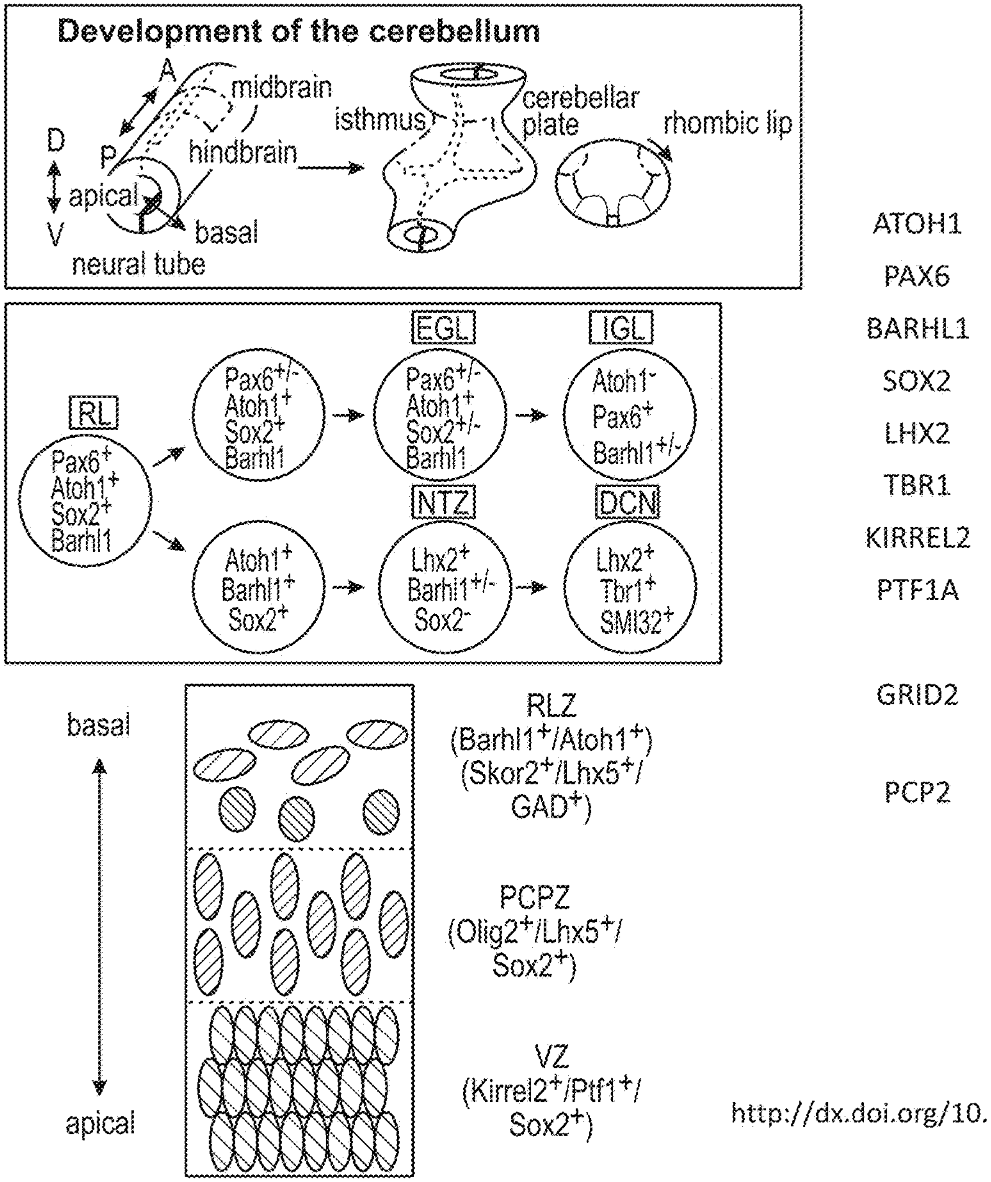

FIG. 7 includes schematics showing developmental heat maps of transcription factors (TF) expressed in cerebellum development and of specific Markers GRID 2.

Figure 8:
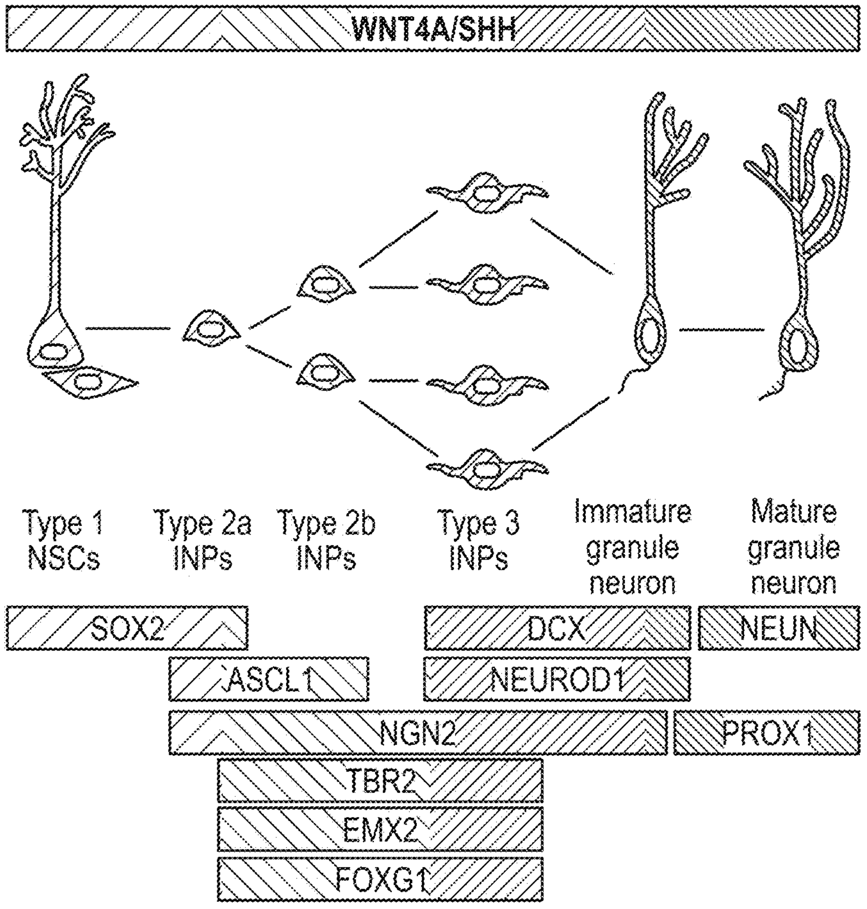

FIG. 8 provides a schematic and a developmental heat map of transcription factors expressed in Hippocampus Dentate Gyrus.

Figure 9:
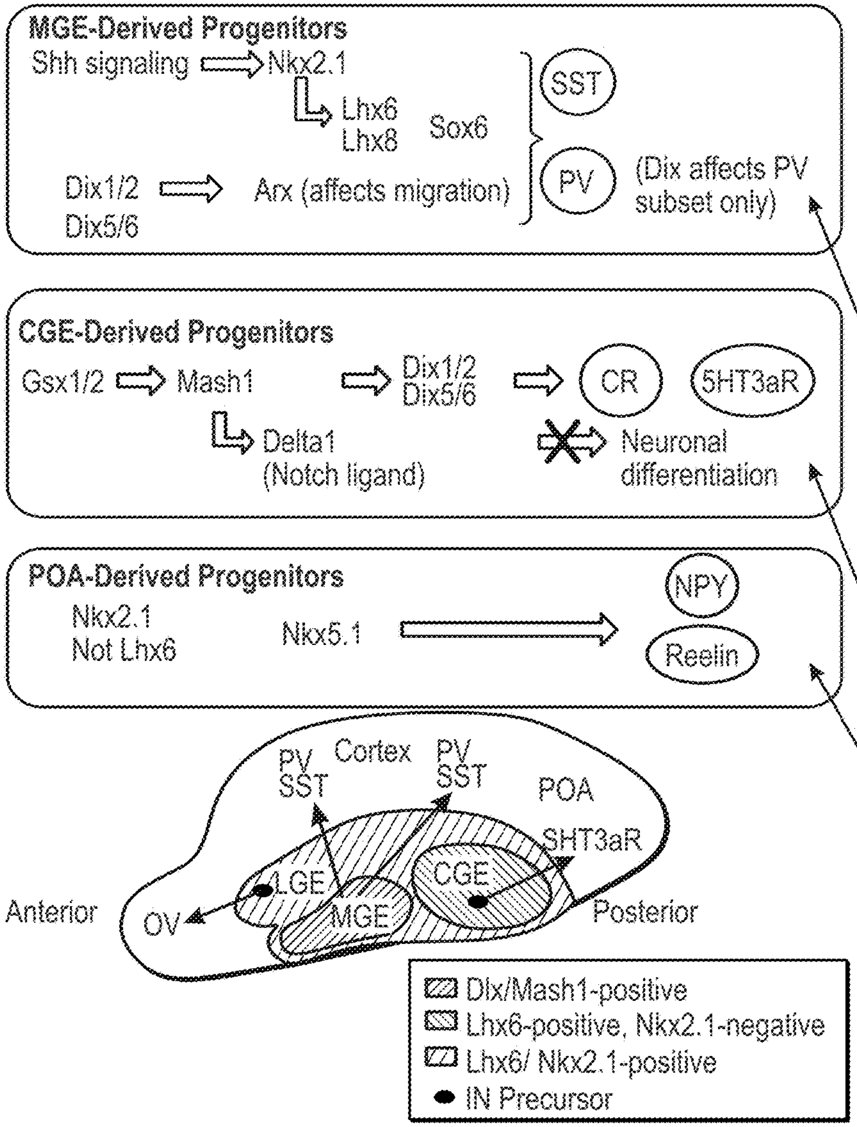

FIG. 9 provides a schematic and a developmental heat map of transcription factors expressed in GABAergic Interneuron Development. GABAergic Interneurons develop late in vitro.

Figure 10:
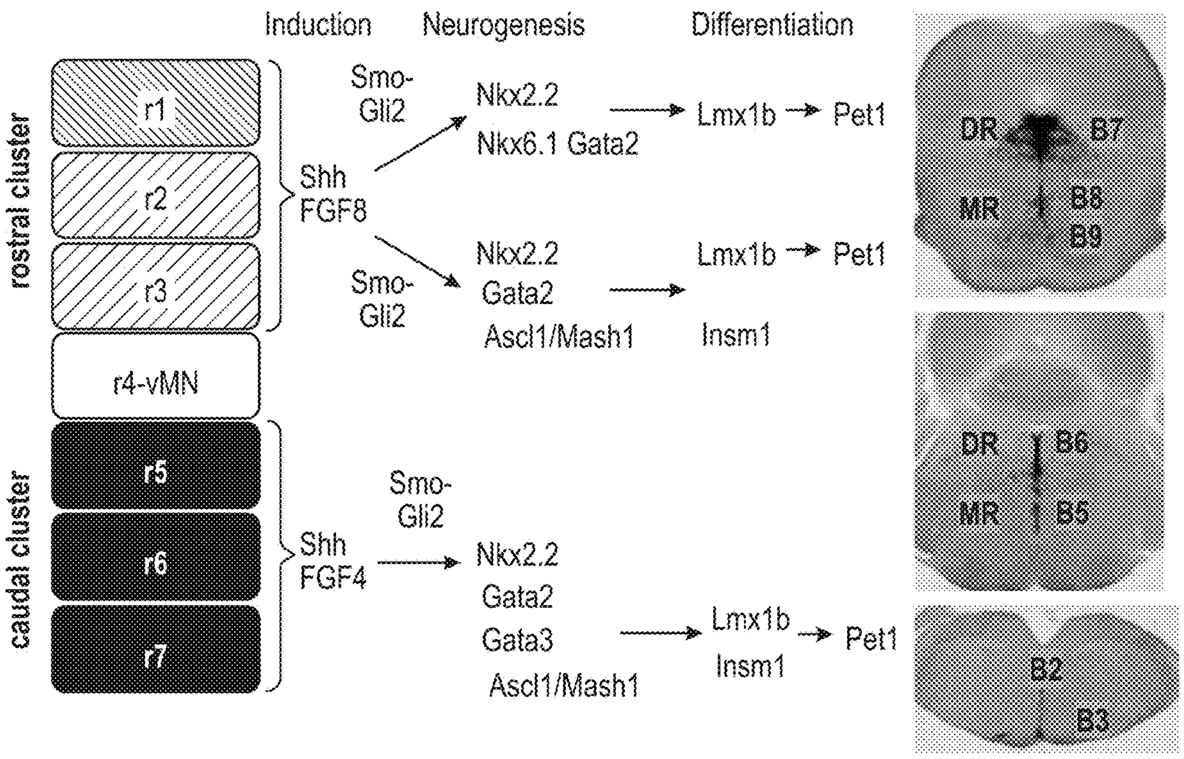

FIG. 10 provides a schematic and a developmental heat map of transcription factors expressed in Serotonergic Raphe Nucleus Markers of the Pons.

Figure 11A:
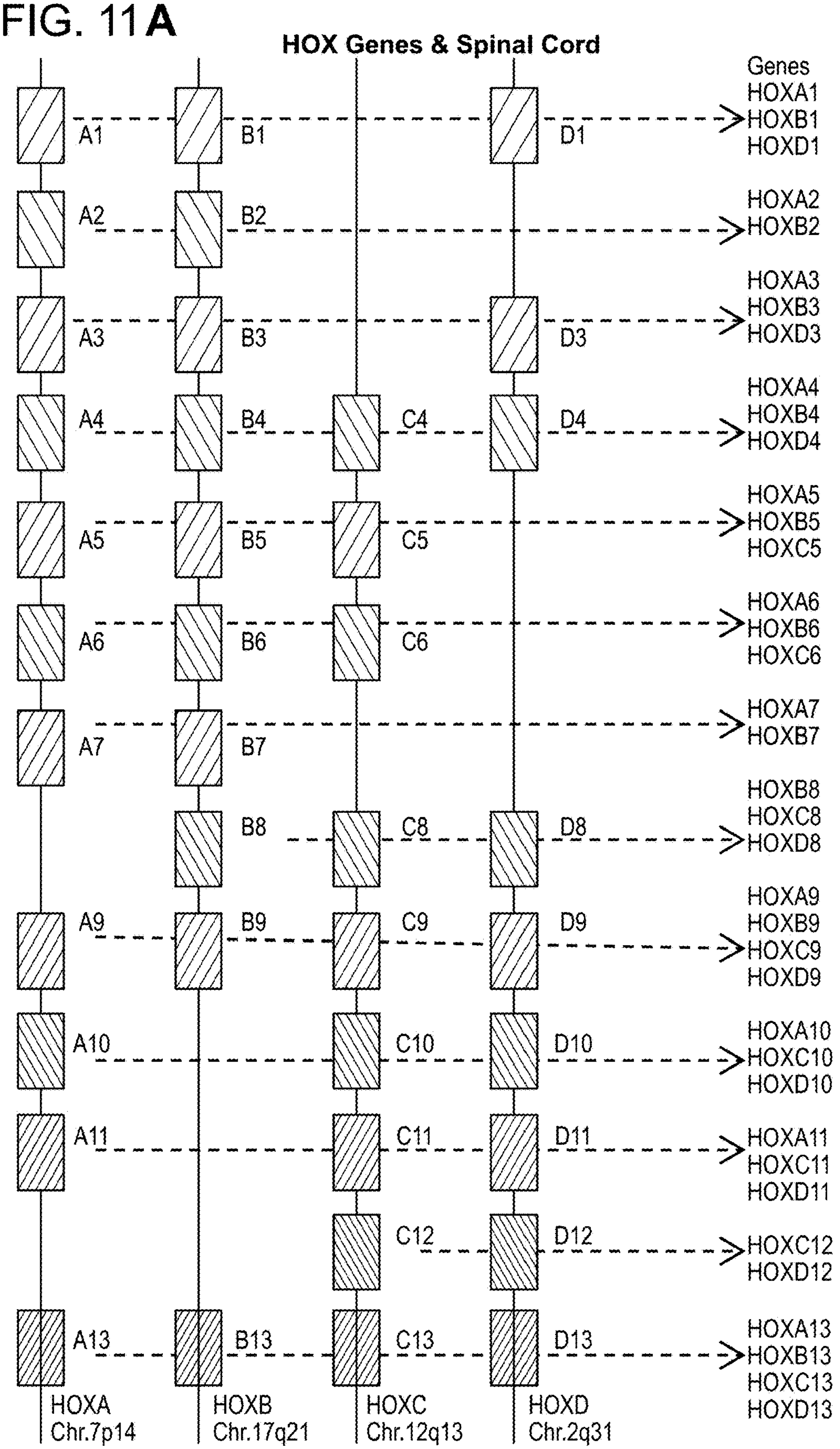
Figure 11B:
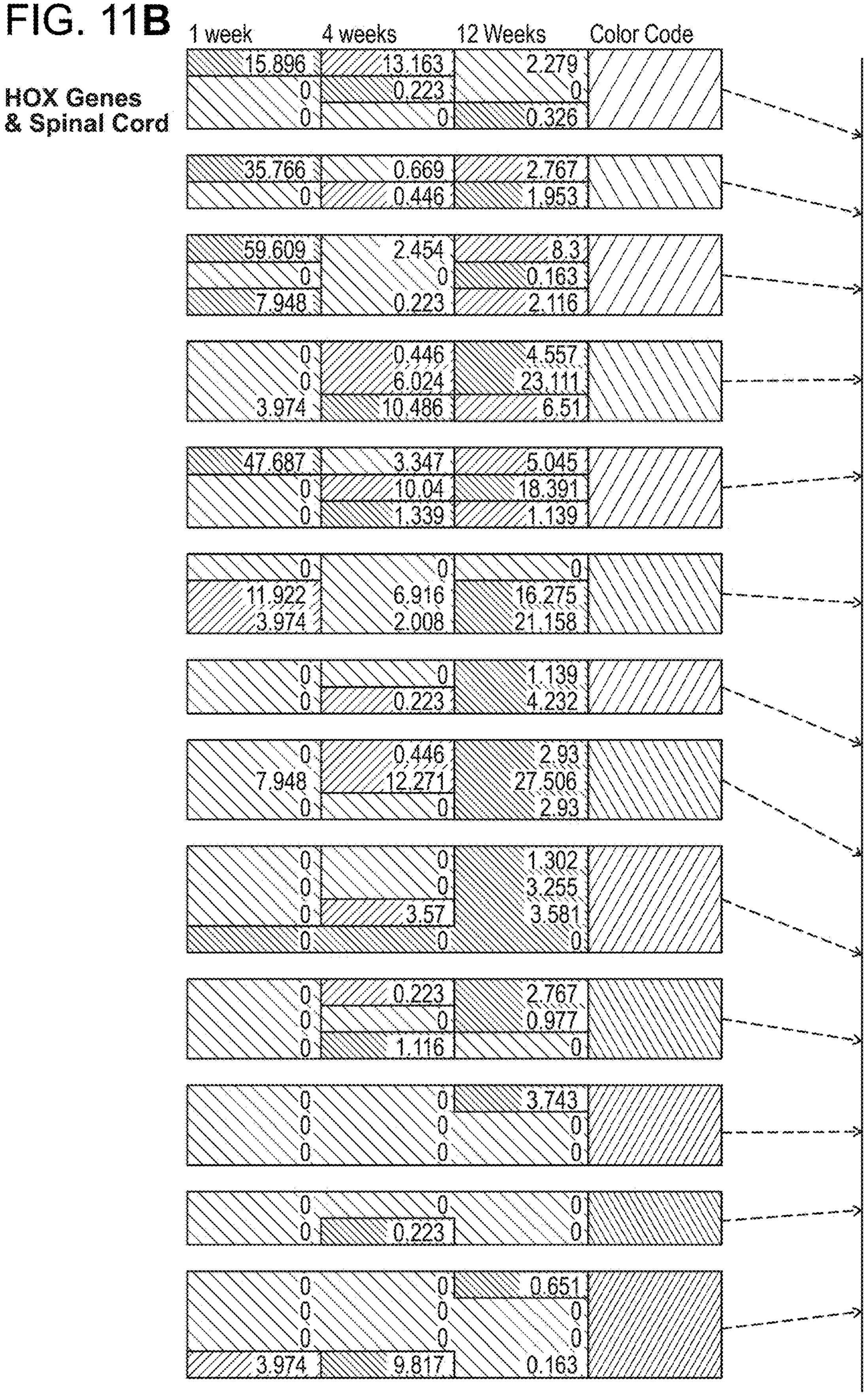

FIGS. 11A-B provide a schematic and a developmental heat map of transcription factor transcriptomics. Hox genes involved in spinal cord cervical, thoracic and lumbar region segmentation are expressed at discrete times in utero. The expression pattern of these Hox gene in organoids as a function of in vitro developmental time (1 week; 4 weeks; 12 weeks)

Figure 12:
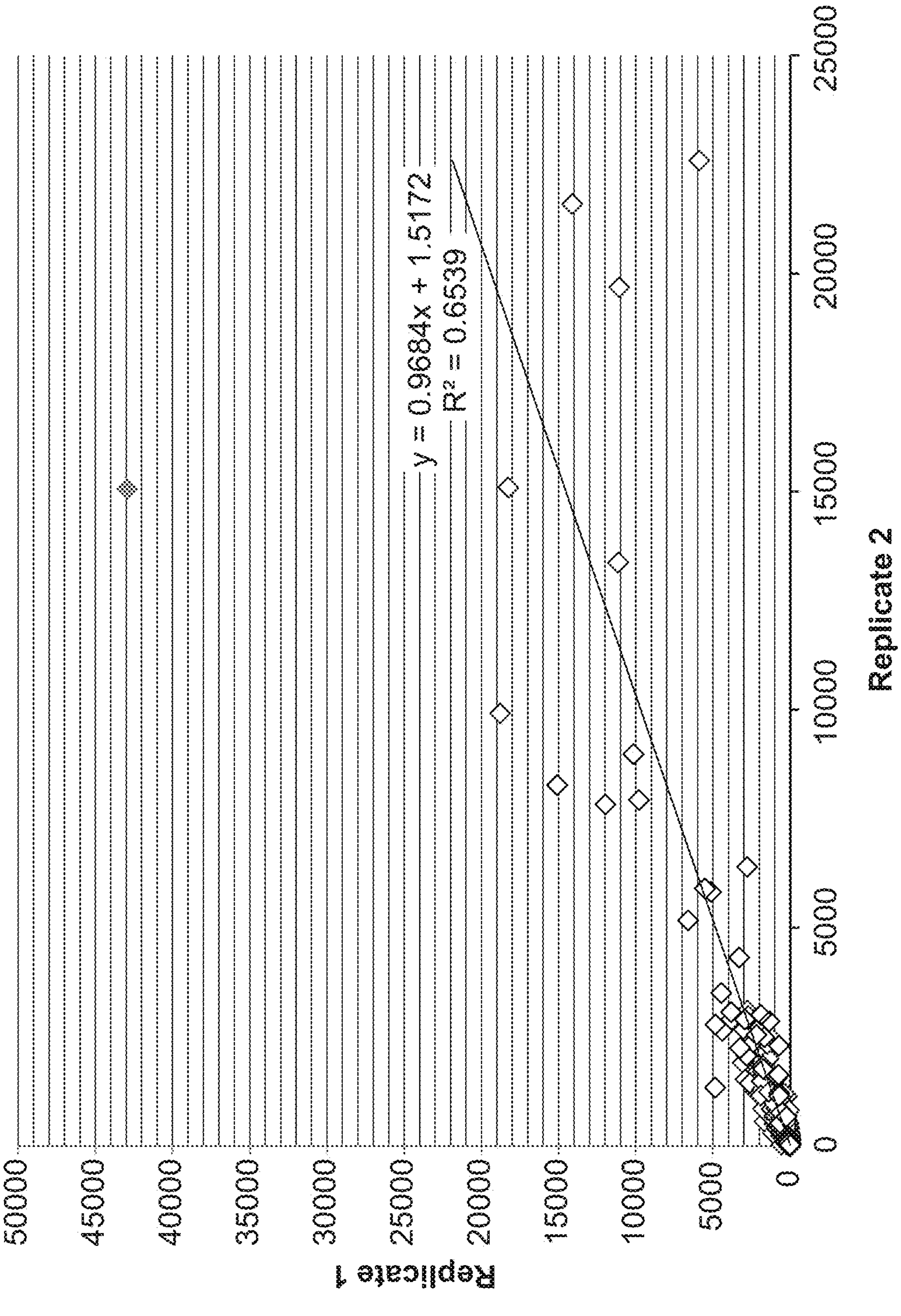

FIG. 12 is a graph showing the replicability of brain organoid development from two independent experiments. Transcriptomic results were obtained by Ampliseq analysis of normal 12 week old brain organoids.

Figure 13:
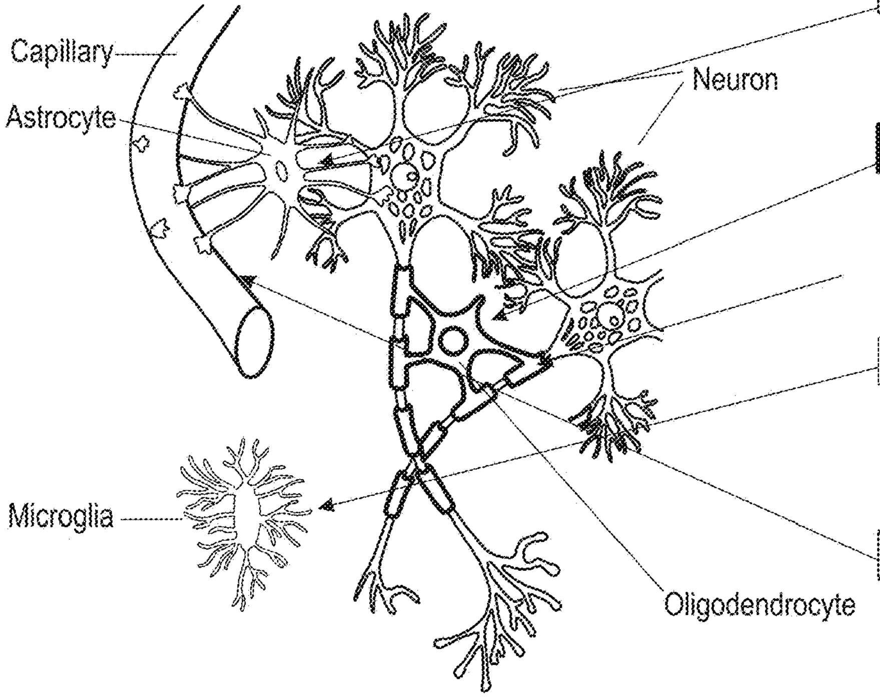

FIG. 13 provides a schematic and gene expression quantification of markers for astrocytes, oligodendrocytes, microglia and vasculature cells.

Figure 14:
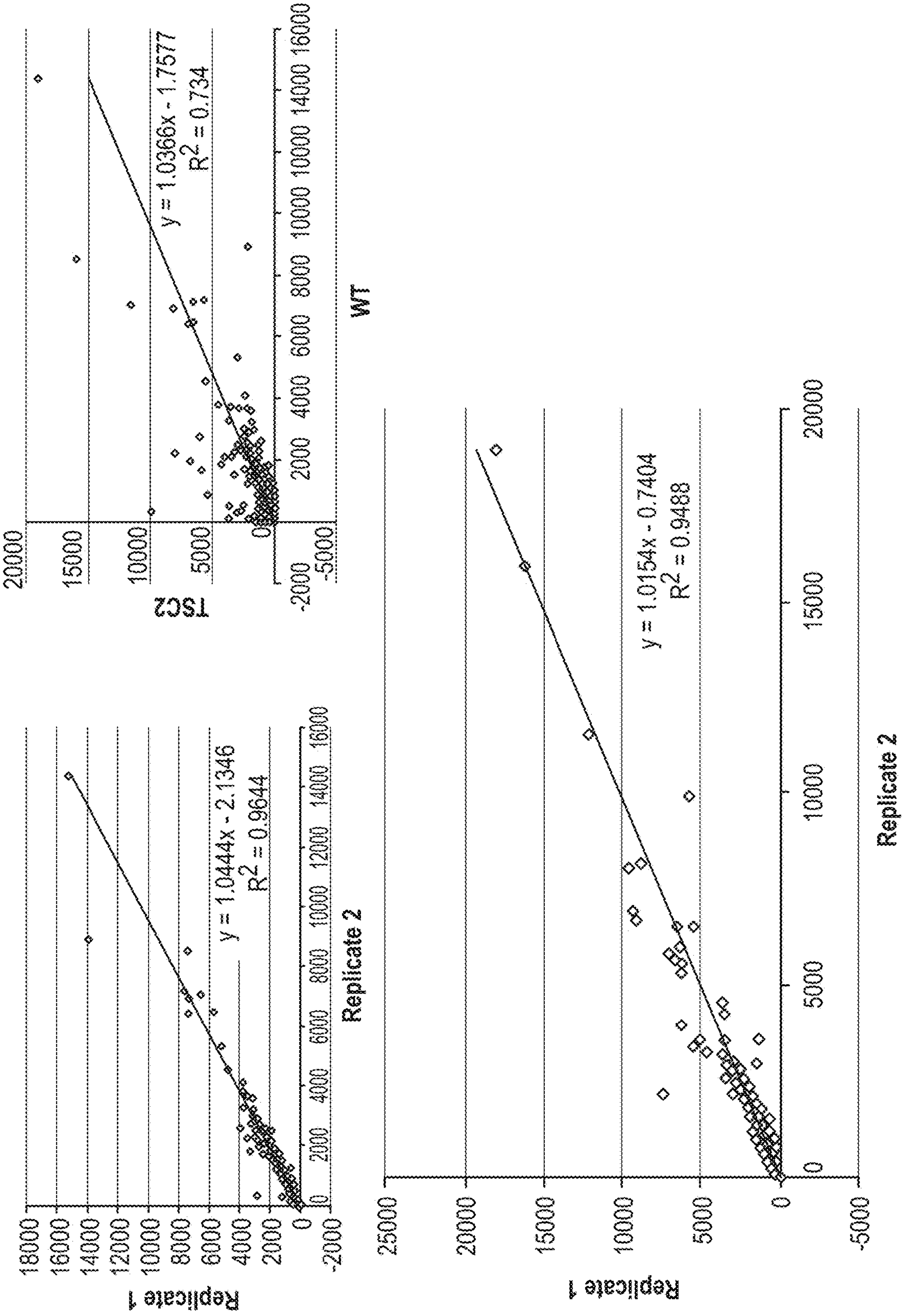

FIG. 14 includes scatter plots of Ampliseq whole genome transcriptomics data from technical replicates for Normal (WT), Tuberous Sclerosis (TSC2) and TSC2 versus WT at ~1 week in culture. Approximately 13,000 gene transcripts are represented in each replicate.

FIG. 15 shows developmental heat maps of transcription factors (TF) expressed in retina development and other specific Markers. Retinal markers are described, for example, in Farkas et al. BMC Genomics 2013, 14:486.

Figure 17:
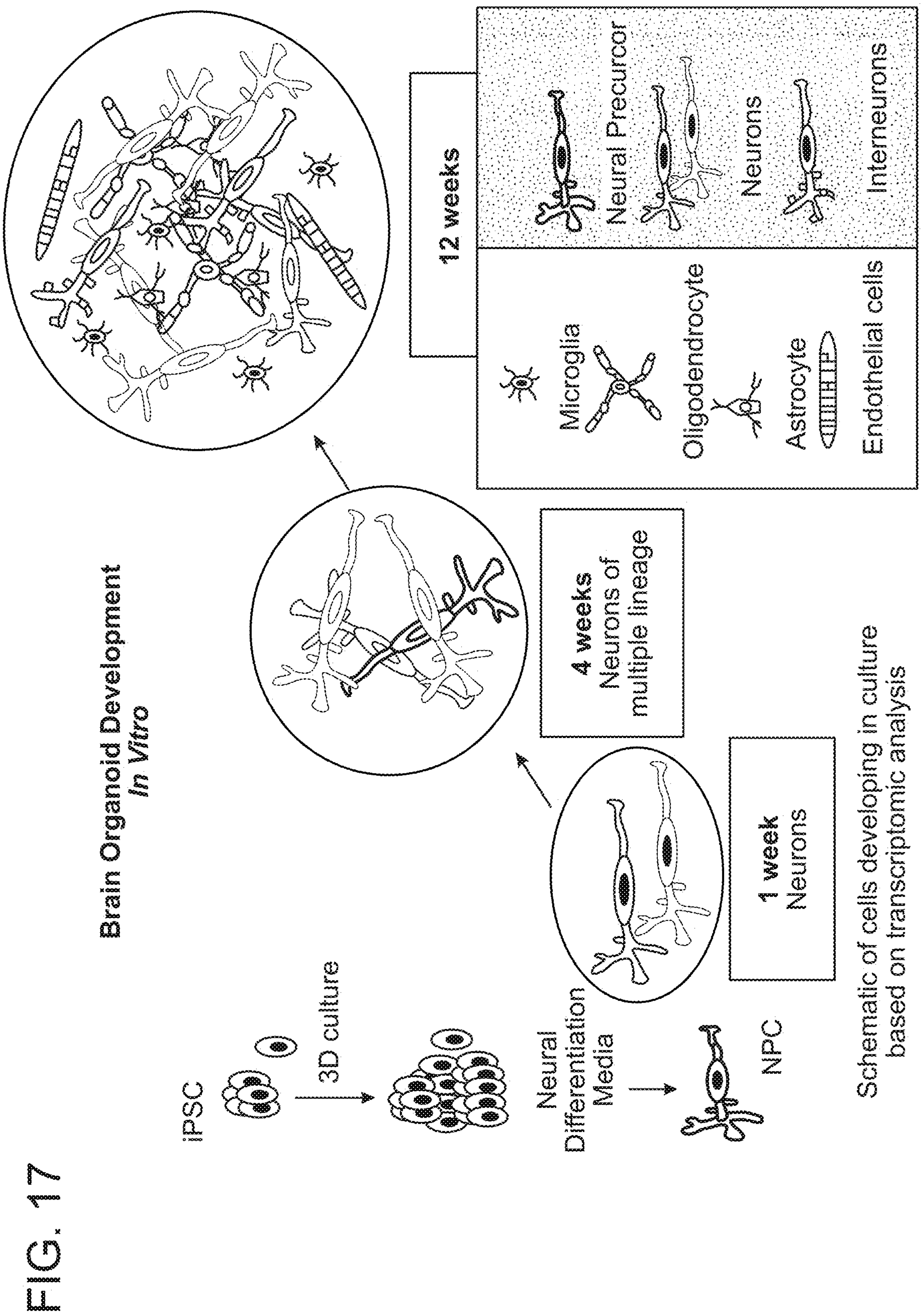

FIG. 16 shows developmental heat maps of transcription factors (TF) and Markers expressed in radial glial cells and neurons of the cortex during development FIG. 17 is a schematic showing the brain organoid development in vitro. iPSC stands for induced pluripotent stem cells. NPC stands for neural progenitor cell.

Figure 18:
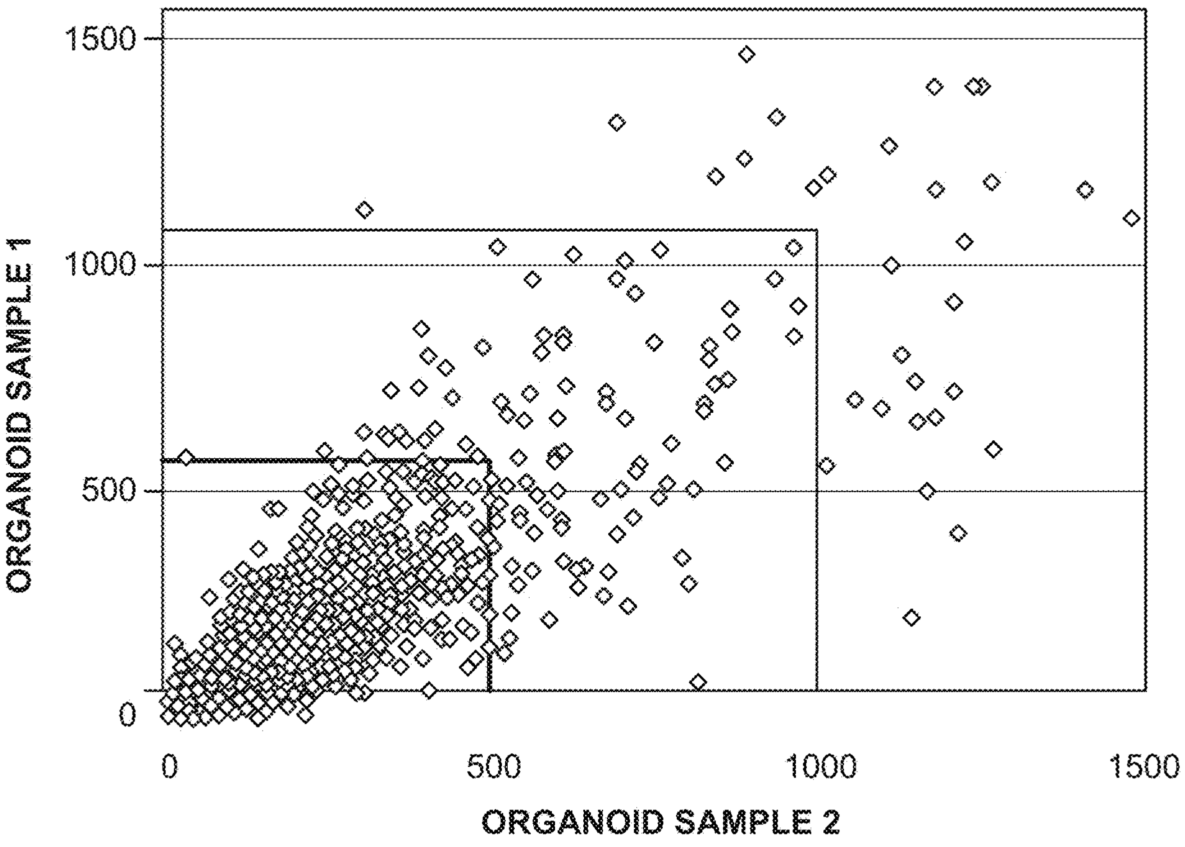

FIG. 18 is a graph showing the replicability of brain organoid development from two independent experiments.

FIGS. 19A-C are tables showing the change in the expression level of certain genes in TSC2 (ARG1743GLN) organoid. About 13,000 gene were analyzed, among which 995 genes are autism related and 121 genes are cancer related.

Figure 20:
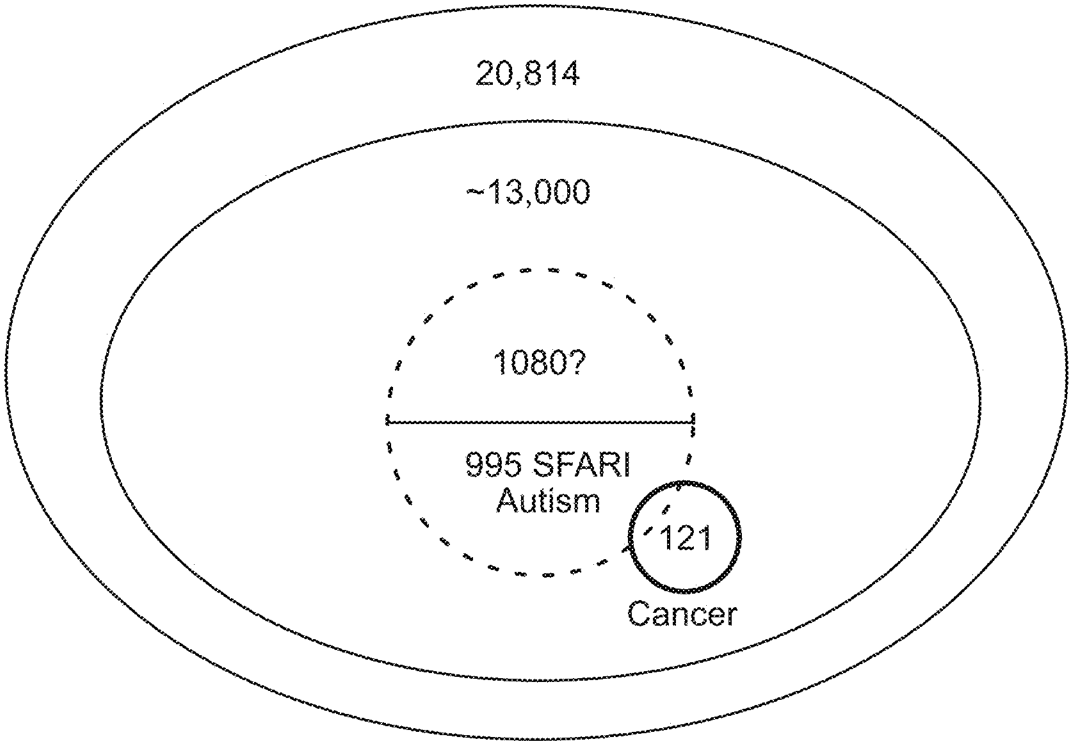

FIG. 20 is a schematic showing the analysis of gene expression in TSC2 (ARG1743GLN) organoid.

FIGS. 21A and 21B are two tables showing the change in the expression level of certain genes in APP gene duplication (ALA246GLU) organoid.

DETAILED DESCRIPTION OF THE INVENTION

The invention features an induced pluripotent stem cell (iPSC) derived organoid useful as an in vitro model to study genetic, molecular, and cellular abnormalities associated with human disorders. This organoid recapitulates in vitro the development, physiology, and other characteristics of the brain (e.g., human, rodent). The invention further provides methods of using this neural organoid to study disease and to identify therapeutic agents for the treatment of neurological diseases and disorders.

The invention is based, at least in part on methods useful for engineering a human brain organoid that after ~12 weeks of culture in vitro exhibits a level of development comparable to that of a human embryonic brain after about 5 weeks in utero. These organoids express markers characteristic of a large variety of neurons. The organoids also include markers for astrocytic, oligodendritic, microglial, and vascular cells. These organoids form all the major regions of the brain including the retina, cortex, midbrain, brain stem, and the spinal cord in a single brain structure which expresses >98% of the genes known to be expressed in the human brain. This organoid is useful as a platform to enable screening of therapeutic agents for efficacy, safety, and toxicity prior to in vivo use in humans.

In particular embodiments, organoids are derived from iPSCs of fibroblast origin. The full development of major parts of brain: retina, cortex, midbrain, hindbrain, and spinal cord within 12 weeks can be observed in these organoids. These organoids may be formed on 96-well plates. Interactive milieu of brain circuits are present in these organoids. Neural niche effects, such as exchange of miRNAs and proteins by exosomes among neurons as well as glial cells, are maintained in these organoids. Results from two independent experiments show greater than 99% reproducibility in gene expression patterns. These have been matched to a human brain reference. Technical replicates from three independent iPSC lines show greater than 99% gene expression patterns. Results from three independent brain organoids, one of which is derived from a female, show greater than 99% gene pattern similarity except for specific diseases pathology. The organoid model is under development to reach an FDA metric for clinical diagnostic use and drug development.

Screening Assays

Neural organoids can be used for toxicity and efficacy screening of agents that treat or prevent the development of a neurological condition. In one embodiment, an organoid generated according to the methods described herein is contacted with a candidate agent. The viability of the organoid (or various cells within the organoid) is compared to the viability of an untreated control organoid to characterize the toxicity of the candidate compound. Assays for measuring cell viability are known in the art, and are described, for example, by Crouch et al. (J. Immunol. Meth. 160, 81-8); Kangas et at (Med. Biol. 62, 338-43, 1984); Lundin et al., (Meth. Enzymol. 133, 27-42, 1986); Petty et al. (Comparison of J. Biolum. Chemilum.10, 29-34, 0.1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega).

In another embodiment, the organoid comprises a genetic mutation that effects neurodevelopment, activity, or function. Polypeptide or polynucleotide expression of cells within the organoid can be compared by procedures well known in the art, such as Western blotting, flow cytometry, immunocytochemistry, in situ hybridization, fluorescence in situ hybridization (FISH), ELISA, microarray analysis, RT-PCR, Northern blotting, or colorimetric assays, such as the Bradford Assay and Lowry Assay.

In one working example, one or more candidate agents are added at varying concentrations to the culture medium containing an organoid. An agent that promotes the expression of a polypeptide of interest expressed in the cell is considered useful in the invention; such an agent may be used, for example, as a therapeutic to prevent, delay, ameliorate, stabilize, or treat an injury, disease or disorder characterized by a defect in neurodevelopment or neurological function. Once identified, agents of the invention may be used to treat or prevent a neurological condition.

In another embodiment, the activity or function of a cell of the organoid is compared in the presence and the absence of a candidate compound. Compounds that desirably alter the activity or function of the cell are selected as useful in the methods of the invention.

Test Compounds and Extracts

In general, agents useful in the invention are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of neurological conditions. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have the desired activity further fractionation of the positive lead extract is necessary to isolate molecular constituents responsible for the observed effect. Thus, the goal of the extraction, fractionation, and purification process is the careful characterization and identification of a chemical entity within the crude extract that treats or prevents a neurological defect. Methods of fractionation and purification of such heterogenous extracts are known in the art. If desired, compounds shown to be useful as therapeutics are chemically modified according to methods known in the art.

Kits

In one embodiment, the invention provides for kits comprising an organoid of the invention. In another embodiment, the invention provides reagents for obtaining an organoid described herein, alone or in combination with directions for the use of such reagents. Associated with such kits may be a notice in the form prescribed by a governmental agency regulating the manufacture, use or sale of biological products, which notice reflects approval by the agency of manufacture, use or sale for human administration.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Generation of Human Induced Pluripotent Stem Cell-Derived Neural Organoids Human induced pluripotent stem cell-derived neural organoids were generated as follows.

Preparation of MEFs

Plate irradiated murine embryonic fibroblasts (MEFs) on gelatin coated substrate in MEF media at a density of $2\times10^5$ cells per well. Place the plate in the 37° C. incubator overnight.

Passaging Induced Pluripotent Stem Cells (iPSCs):

Wash MEFs with prewarmed PBS. Replace media with 1 ml iPSC media/ROCK inhibitor per well.

Remove the iPSC plate from the incubator. Feed iPSC cells with iPSC media. Using a sterile StemPro EZPassage tool, cut and resuspend the iPSC colonies. Gently resuspend cells, and divide and transfer to the MEF containing wells (1:1)

1. Making Embryoid Bodies (EBs):

Coat a 100 mm culture dish with 0.1% gelatin. Put in 37° C. incubator for 20 minutes. Remove gelatin, and let the dish air dry in BSC till ready to use.

Two wells of a 6 well plate should provide enough cells for a 96 well plate. Wash wells containing iPSCs and MEFs with prewarmed PBS that lacks Ca2+/Mg2+. Remove the PBS solution and replace with 1 ml/well of ACCUTASE™, a prewarmed cell detachment solution of proteolytic and collagenolytic enzymes. Incubate plates at 37° C. incubator for 20 minutes until all of the cells are detached.

Add prewarmed iPSC media to each well and gently triturate to break up visible colonies.

Add additional pre-warmed media to 15 mls, and move the cells onto a gelatin-coated culture plate at 37° C. incubator for 60 minutes to allow MEFs to adhere to the coated surface. The iPSCs present in the cell suspension are counted.

Centrifuge the suspension at 300×g for 5 minutes at room temperature. Discard the supernatant and resuspend the cells in EB media with ROCK inhibitor (50 uM final concentration) to a volume of 9,000 cells/150 μl.

Plate 150 μl in a LIPIDURE® low-attachment U-bottom 96-well plate incubate at 37° C. The LIPIDURE coating contains MPC Polymer, a biocompatible polymer composed by Phosphoryl Choline.

2. Initiation of Germ Layer Differentiation:

EBs are fed every other day by gently replacing three fourths of the EB media without disturbing the EB forming at the bottom of the well. It is important that the interactions among the iPSC cells within the EB are not perturbed by shear stress during pipetting. For the first four days, the EB media includes 50 uM ROCK inhibitor and 4 ng/ml bFGF. For the remaining two to three days, no ROCK inhibitor or bFGF is added to the EB.

3. Induction of Primitive Neuroepithelia:

EBs in the LIPIDURE® 96 well plate are transferred on the sixth or seventh day to two 24 well plates containing 500 μl/well Neural Induction media. Two EBs are gently plated in each well.

After 2 days, the media is changed. The EBs should take on a "halo" around their perimeter, indicating neuroectodermal differentiation. Only EBs having a "halo" are selected for embedding in matrigel. Other EBs are discarded.

4. Matrigel Embedding:

Sterilize plastic paraffin film (PARAFILM) rectangles [5 cm×7 cm] using 3% hydrogen peroxide and create a series of dimples in the rectangles. This may be accomplished, for example, by centering the rectangles onto an empty sterile 200 ul tip box press, and pressing the rectangles gently to dimple it with the impression of the holes in the box. Spray the boxes with ethanol, and let them stay in the BSC to dry.

Thaw frozen Matrigel matrix aliquots (500 μl) on ice in the refrigerator for 2-3 hours until equilibrated at 4° C.

A single EB from Step 3 is transferred to each dimple of the film. A 7 cm×5 cm rectangle should be hold 20 EBs. 20 μl aliquots of Matrigel are transferred onto the EB after removing extra media with a pipette. Incubate at 37° C. for 30 min to allow the Matrigel to polymerize. The 20 μl droplet of viscous Matrigel was found to form an optimal 3D environment that supports the proper growth of the brain organoid from EBs by sequestering the gradients of morphogens and growth factors secreted by cells within the EB early, yet permitting exchange of essential nutrients and gases. Gentle oscillation by hand twice a day for a few minutes within a tissue culture incubator (37° C./5% $CO_2$) further allows optimal exchange of gases and nutrients to the embedded EBs.

Add Differentiation Media 1 a 100 mm tissue culture dish. Invert the film containing the EB in Matrigel onto the media and incubate at 37° C. for 16 hours.

After 16 hours, the EB/Matrigel droplets are transferred from the film into culture dishes containing media. Static culture at 37° C. is continued for 4 days to form stable neural organoids.

5. Organoid Development:

Organoids are gently transferred to culture dishes containing differentiation media 2. The flasks are set on an orbital shaker rotating at 40 rpm within the 37° C./5% incubator. Without wishing to be bound by theory, these conditions were selected to minimize disturbance of diffusion gradients among early progenitors of neurons of different lineages that are may affect patterning during development of the brain organoids into more complex and complete structures that include the retina, cortex, midbrain, hindbrain and spinal cord; to provide optimum exchange of gases within the matrix for survival of organoids and prevent apoptosis; provide nutrients to diffuse into the matrix optimally; and allow efflux of waste products effectively mimicking the function of the cerebrospinal fluid. The media is changed in the flasks every 3-4 days to provide sufficient time for morphogen and growth factor gradients to act on targets within the recipient cells forming relevant structures of the brains. The change of media is done with care to avoid unnecessary perturbations to the morphogen/secreted growth factor gradients setting up in the outer most periphery of the organoids as the structures grow into larger organoids.

FIG. 16 illustrates the brain organoid development in vitro. Based on transcriptomic analysis, iPSC cells form a body of cells after 3D culture, which becomes neural progenitor cells (NPC) after neural differentiation media treatment. Neurons can be observed in the cell culture in about one week. In about four (4) weeks, neurons of multiple lineage appear. In about twelve (12) weeks, the organoid develops to a stage that has different types of cells, including microglia, oligodendrocyte, astrocyte, neural precursor, neurons, and interneurons.

Example 2: Human Induced Pluripotent Stem Cell-Derived Neural Organoids Express Characteristics of Human Brain Development After ~12 weeks in culture in vitro, transcriptomic and immunohistochemical analysis indicate that organoids generated according to the methods delineated in Example 1, contain cells expressing markers characteristic of neurons, astrocytes, oligodendrocytes, microglia, and vasculature (FIGS. 1-14) and all major brain structures of neuroectodermal derivation. Morpologically by bright field imaging, the organoids include readily identifiable neural structures including cerebral cortex, cephalic flexture, and optic stalk (Grey's anatomy text book). Their gene expression pattern is >98% concordant with those of the adult human brain reference (Clontech). They also express genes in a developmentally organized manner previously described (for the midbrain mescencephalic dopaminergic neurons, for example; Blaese et al., 2015). They also stain for multiple neural specific markers (dendrites, axons, nuclei), cortical neurons (Doublecortin) midbrain dopamine neurons (Tyrosine Hydroxylase) and astrocytes (GFAP by immunohistology).

Figure 1A:
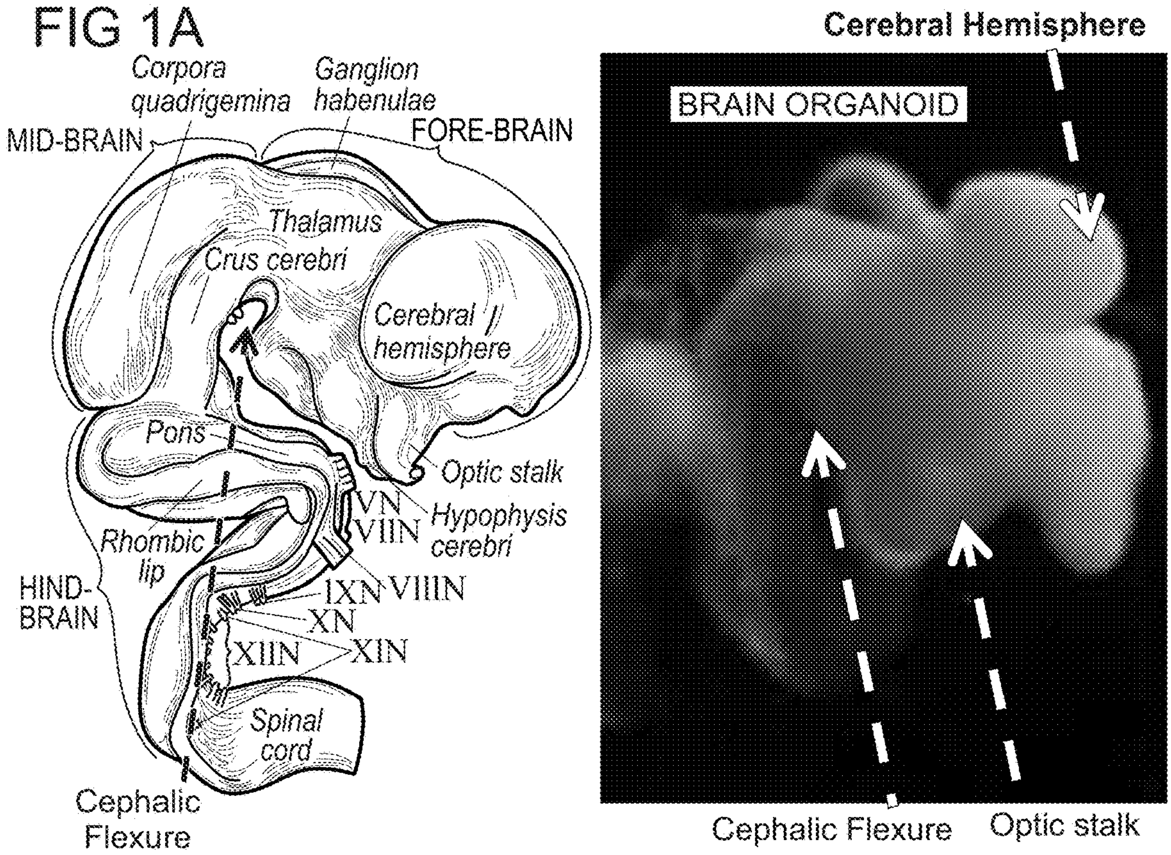
FIG. 1A is a micrograph showing a 4× dark field image of Brain Organoid Structures typical of approximately 5 week in utero development achieved in 12 weeks in vitro. Average size: 2-3 mm long.
Figure 1B:
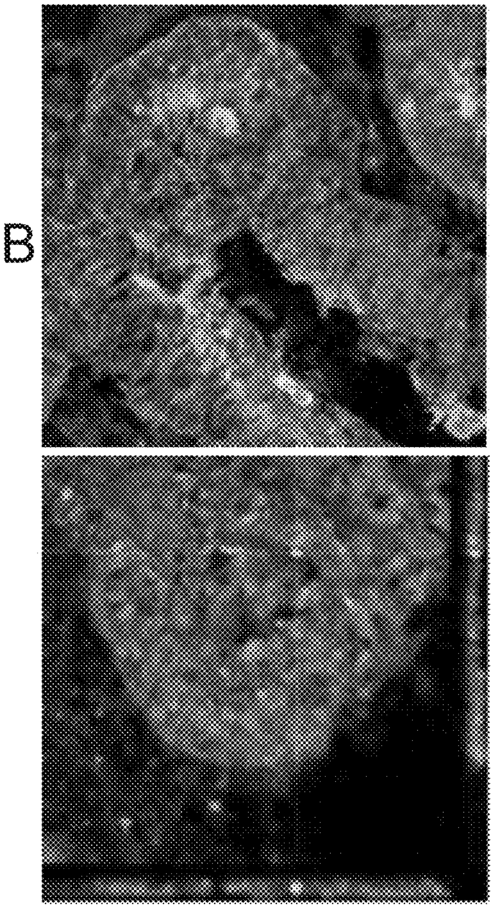
FIG. 1B shows immuno-fluorescence images of sections of iPSC-derived human brain organoid after approximately 12 weeks in culture. Z-stack of thirty three optical sections, 0.3 microns thick, obtained using laser confocal imaging with a 40× lens. Stained with Top panel: beta III tubulin (green: axons); MAP2 (red: dendrites); Hoechst (blue: nuclei); Bottom panel: Doublecortin (red)
Figure 2:
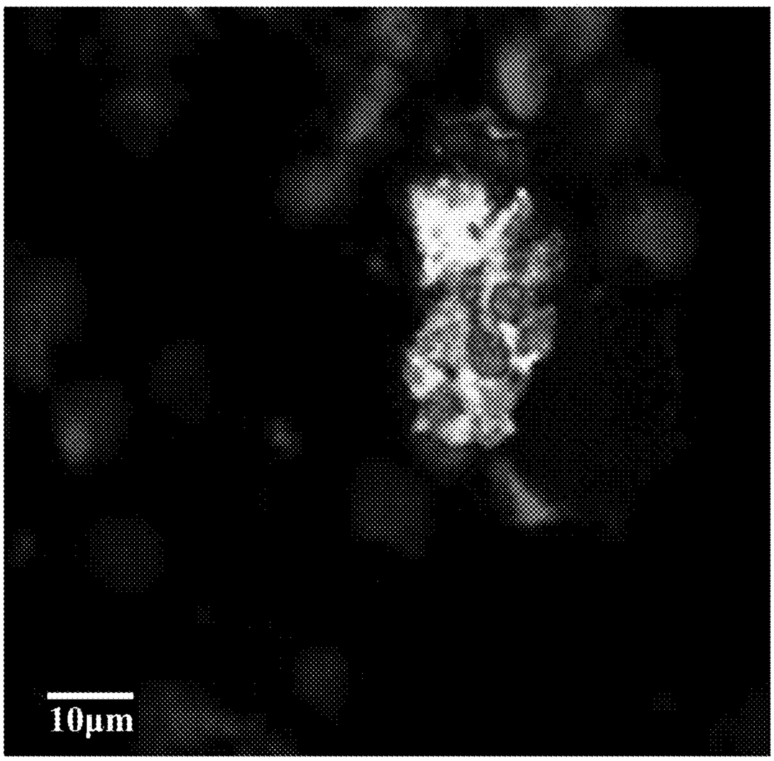
FIG. 2 is a micrograph showing immunohistochemical staining of brain organoid section with the midbrain marker tyrosine hydroxylase. Paraformaldehyde fixed sections of a 8-week old brain organoid was stained with an Ab to tyrosine hydroxylase and detected with Alexa 488 conjugated secondary Abs (green) and counter stained with Hoechst to mark cell nuclei (blue). spinning disc confocal image (40× lens) of section stained with an antibody that binds tyrosine hydroxylase and Hoechst (scale bar: 10 μm).
Figure 3:
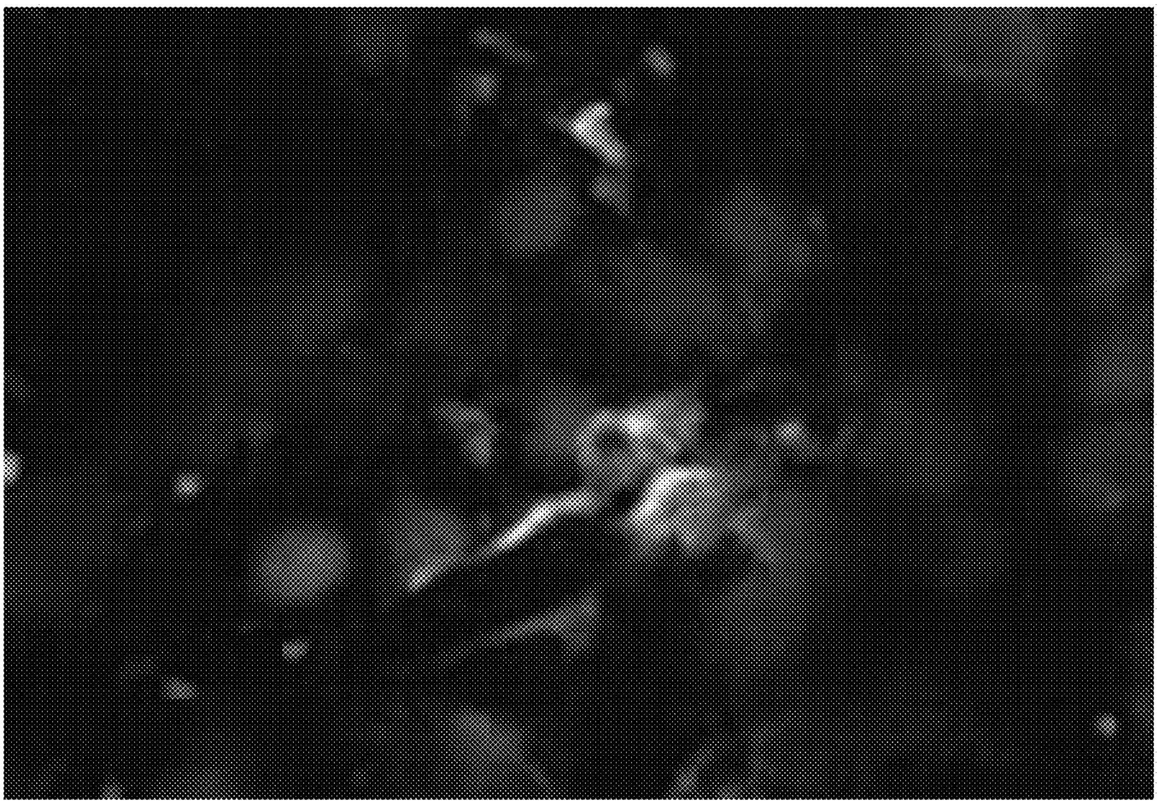
FIG. 3: Spinning disc confocal image (40× lens) of section. Astrocytes stained with GFAP (red) and mature neurons with NeuN (green).
Figure 4:
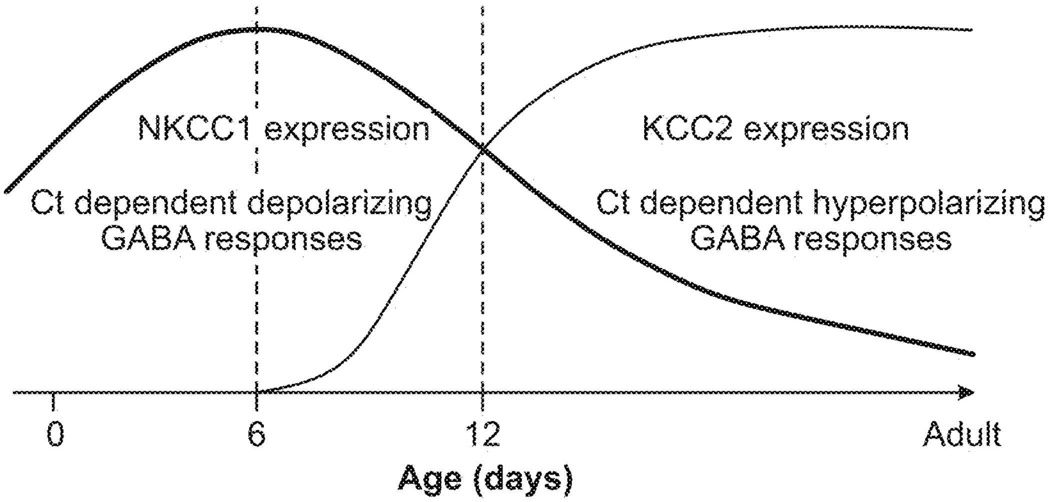
FIG. 4 is a schematic showing in the upper panel a Developmental Expression Profile for transcripts as Heat Maps of NKCC1 and KCC2 expression at week 1, 4 and 12 of organoid culture as compared to approximate known profiles (lower panel). NKCC1: Na(+)-K(+)-Cl(−) cotransporter isoform 1. KCC2: K(+)-Cl(−) cotransporter isoform 2.
Figure 5A:
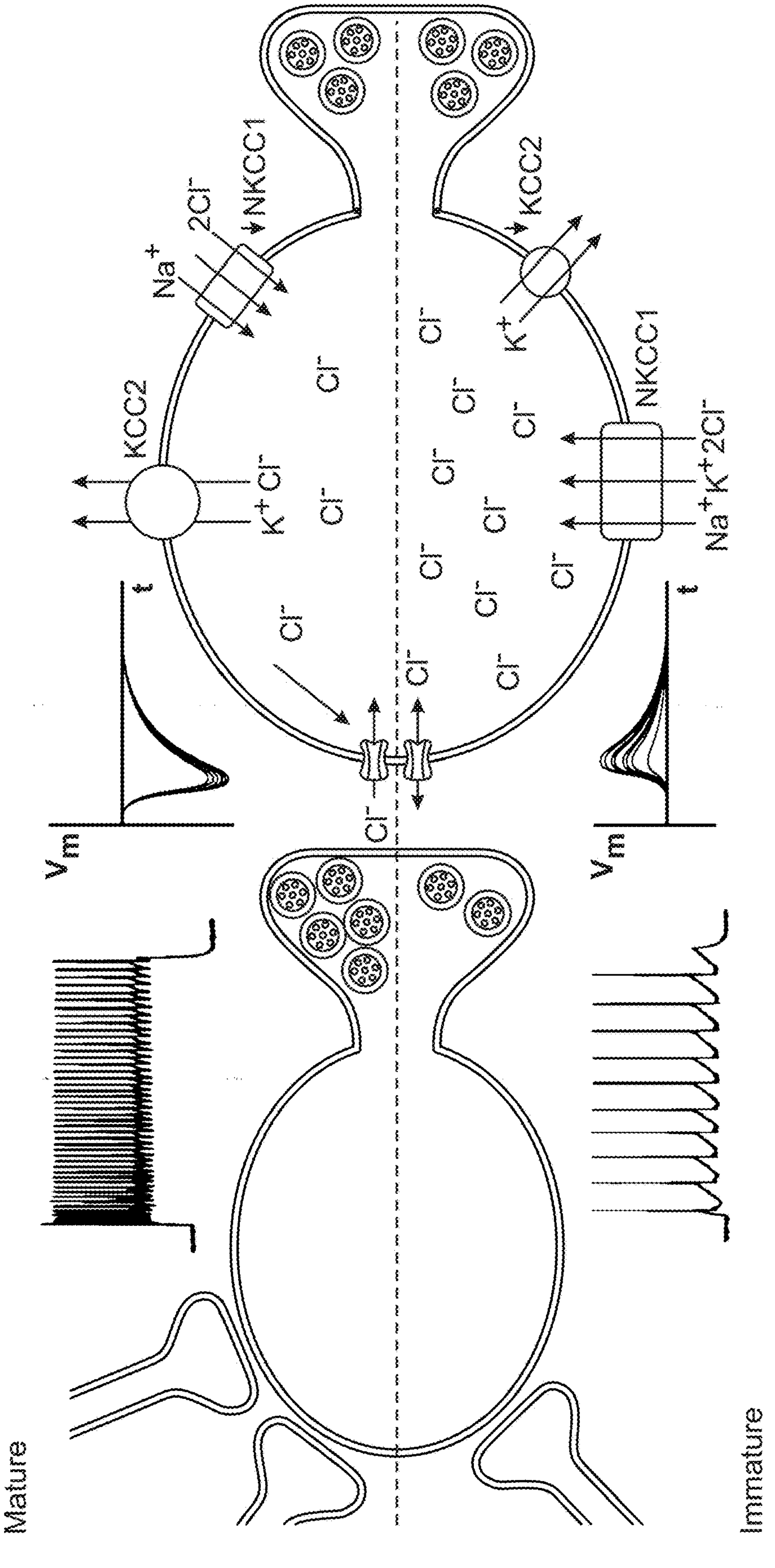
FIG. 5A is a schematic showing GABAergic chloride gradient regulation by NKCC1 and KCC2.

All human organoids were derived from iPSCs of fibroblast origin (from System Biosciences, Inc). The development of a variety of brain structures was characterized in the organoids. Retinal markers are shown in FIG. 15. Doublecortin (DCX) a microtubule associated protein expressed during cortical development was observed (FIG. 1A and FIG. 1B, FIG. 16. Midbrain development was characterized using a marker for tyrosine hydroxylase (FIG. 2). Transcriptomics was used to detect the expression of the midbrain markers DLK1, KLHL1, and PTPRU (FIG. 6A). Staining with GFAP was used to identify the presence of astrocytes in the organoids (FIG. 3). The presence of mature neurons was characterized with staining for NeuN (FIG. 3). The presence of NKCC1 and KCC2, a neuron-specific membrane protein, was observed (FIG. 4). A schematic of the roles of NKCC1 and KCC2 is provided at FIG. 5A. FIG. 5B indicates that a variety of markers that are expressed during human brain development are also expressed in the organoids generated as described in Example 1.

Markers expressed within the organoids are consistent with the presence of the following cell types: excitatory, inhibitory, cholinergic, dopaminergic, serotonergic, astrocytic, oligodendritic, microglial, vasculature. These markers are consistent with those identified by the Human Brain Reference (HBR) from Clontech (FIG. 5C) and were reproducible in independent experiments (FIG. 5D). Markers characteristic of tissues outside the brain were not observed (FIG. 6B).

Figure 11B:
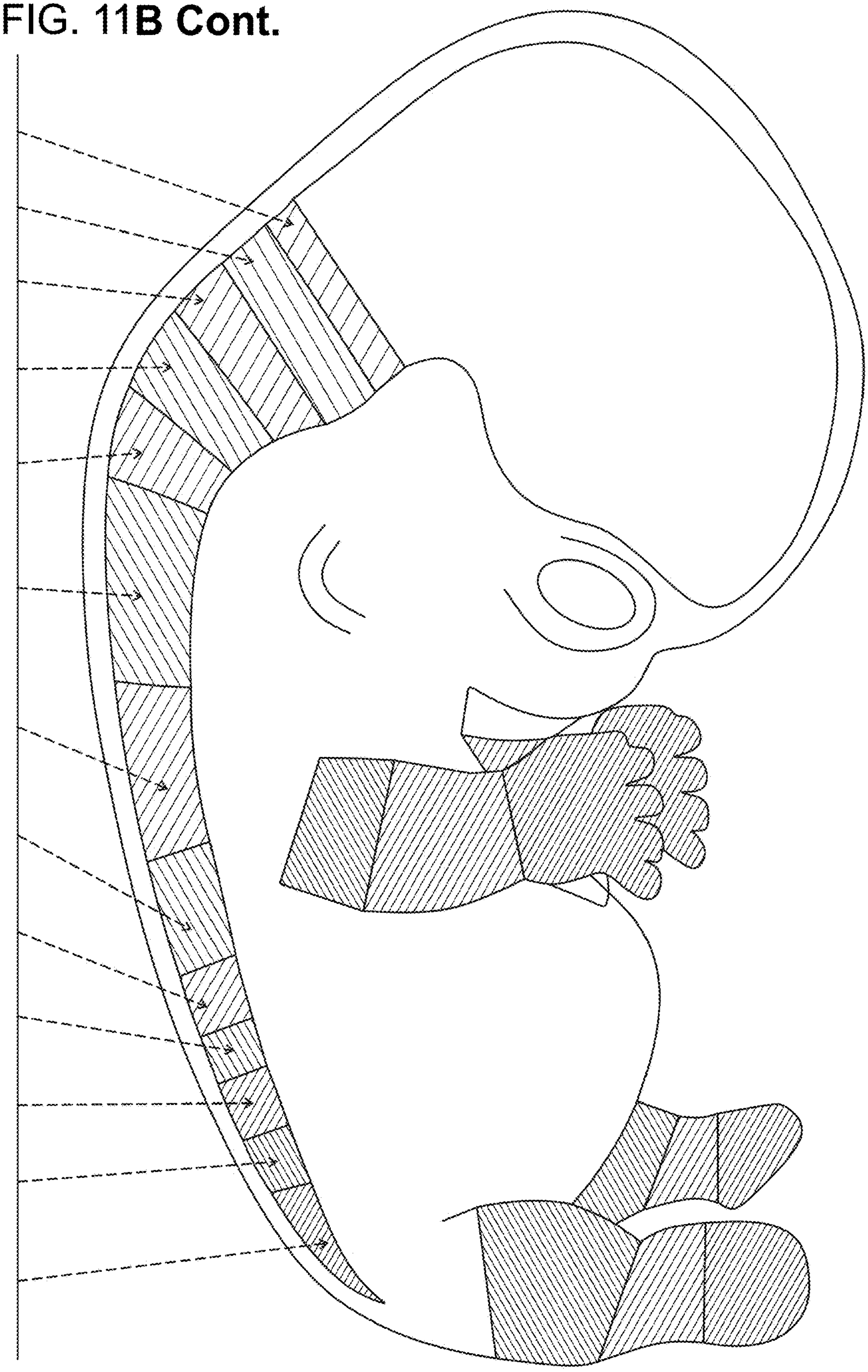

Tyrosine hydroxylase, which is an enzyme used in the synthesis of dopamine, was observed in the organoids using immunocytochemistry (FIG. 5B) and transcriptomics (FIG. 6A). The expression of other dopaminergic markers, including vesicular monoamine transporter 2 (VMAT2), dopamine active transporter (DAT) and Dopamine receptor D2 (D2R) were observed using transcriptomic analysis. FIG. 7 delineates the expression of markers characteristic of cerebellar development. FIG. 8 provides a list of markers identified using transcriptomics that are characteristic of neurons present in the hippocampus dentate gyrus. spinal cord was observed after 12 weeks of in vitro culture. FIG. 9 provides a list of markers identified using transcriptomics that are characteristic of GABAergic interneuron development. FIG. 10 provides a list of markers identified using transcriptomics that are characteristic of the brain stem, in particular, markers associated with the serotonergic raphe nucleus of the pons. FIG. 11 lists the expression of various Hox genes that are expressed during the development of the cervical, thoracic and lumbar regions of the spinal cord.

FIG. 12 shows that results are reproducible between experiments. The expression of markers detected using transcriptomics is summarized in FIG. 13.

In sum, the results reported herein support that the invention provides an in vitro cultured organoid that resembles a ~5 week old human fetal brain based on size and specific morphological features with great likeness to the optical stock, the cerebral hemisphere, and cephalic flexure in a ~2-3 mm organoid that can be grown in culture dishes. High resolution morphology analysis was carried out using immunohistological methods on sections and confocal imaging of the organoid to establish the presence of neurons, axons, dendrites, laminar development of cortex, and the presence of midbrain marker.

This organoid includes an interactive milieu of brain circuits as represented by the laminar organization of the cortical structures in Fig. X and thus supports formation of native neural niches in which exchange of miRNA and proteins by exosomes can occur among different cell types.

The brain organoids were evaluated at weeks 1, 4 and 12 by transcriptomics. The organoid is reproducible and replicable (FIGS. 5C, 5D, FIG. 12, and FIG. 18). Brain organoids generated in two independent experiments and subjected to transcriptomic analysis showed >99% replicability of the expression pattern and comparable expression levels of most genes with <2-fold variance among some of them.

Gene expression patterns were analyzed using whole genome transcriptomics as a function of time in culture. Results reported herein indicates that known developmental order of gene expression in vivo occurs, but on a somewhat slower timeline. Using the transcription factors NURR1 and PITX3 that are uniquely expressed in the development of mesencephalic neurons in the midbrain as examplars, we show that their temporal expression patterns in vitro replicate known in vivo gene expression patterns (FIG. 6A). Similarly, the transition from GABA mediating excitation to inhibition, occurs following the switch over of the expression of the Na(+)-K(+)-2Cl(−)) cotransporter NKCC1 (SLC12A2), which increases intracellular chloride ions, to the K(+)-Cl(−) cotransporter KCC2 (SLC12A5) (Owens and Kriegstein, 2002), which decreases intracellular chloride ions (Blaesse et al., 2009). We have data on the development of the brain organoids in culture in which the expression profile of NKCC1 and KCC2 changes in a manner consistent with an embryonic brain transitioning from GABA being excitatory to being inhibitory (FIGS. 4 & 5) and can be monitored by developmental transcriptomics.

The organoids described above were obtained using the following methods and materials.

Cells:

Human iPSCs, feeder-dependent (System Bioscience. WT SC600A-W)

CF-1 mouse embryonic fibroblast feeder cells, gamma-irradiated (Applied StemCell, Inc #ASF-1217)

Growth Media and Supplements

DMEM non-essential amino acids (MEM-NEAA, Invitrogen #11140-050)

Phosphate Buffered Saline, sterile (Invitrogen #14040-091)

Phosphate Buffered Saline, Ca++ and Mg++ free (Invitrogen #14190-094)

Gentamicin Reagent Solution (Invitrogen #15750-060)

Antibiotic-Antimycotic (Invitrogen #15240-062)

2-mercaptoethanol (EmbryoMAX, EMBMillipore #ES-007-E)

Basic fibroblast growth factor (FGF, PeproTech #051408-1)

Heparin (Sigma, #H3149-25KU) Insulin solution (Sigma #I9278-5 ml)

Dimethyl sulfoxide (#D9170-5VL) ROCK Inhibitor Y27632 (Millipore #SCM075)

Gelatin solution, Type B (Sigma #G1393-100 ml)

Matrigel Matrix (BD Bioscience #354234), NOT Growth Factor Reduced Matrigel

Accutase (Sigma #A6964)

Hydrogen Peroxide (Fisher #H325-500)

Ethanol

Sterile H2O

Media Composition:

MEF Media: DMEM media supplemented with:

10% Feta Bovine Serum 100 units/ml penicillin 100 microgram/ml streptomycin 0.25 microgram/ml Fungizone IPSC Media: DMEM/F12 media supplemented with:

20% KnockOut Replacement Serum

3% Fetal Bovine Serum o 2 mM Glutamax

1× Minimal Essential Medium Nonessential Amino Acids 20 nanogram/ml basic Fibroblast Growth Factor EB Media: Dulbecco's Modified Eagle's Medium (DMEM) (DMEM)/Ham's F-12 media (commercially available from Invitrogen) supplemented with:

20% KnockOut Replacement Serum

3% Fetal Bovine Serum o 2 mM Glutamax

1× Minimal Essential Medium Nonessential Amino Acids 55 microM beta-mercaptoethanol 4 ng/ml basic Fibroblast Growth Factor Neural Induction Media: DMEM/F12 media supplemented with:

1:50 dilution N2 Supplement

1:50 dilution GlutaMax

1:50 dilution MEM-NEAA 10 microgram/ml Heparin

Differentiation Media 1: DMEM/F12 media: Neurobasal media (1:1) (each of which is commercially available from Invitrogen) supplemented with:

1:200 dilution N2 supplement

1:100 dilution B27−vitamin A 2.5 microgram/ml insulin 55 microM beta-mercaptoethanol kept under nitrogen mask and frozen at −20° C.

100 units/ml penicillin 100 microgram/ml streptomycin 0.25 microgram/ml Fungizone DIFFERENTIATION MEDIA 2: DMEM/F12 media: Neurobasal media (1:1) supplemented with:

1:200 dilution N2 supplement

1:100 dilution B27+vitamin A 2.5 microgram/ml Insulin 55 uM beta-mercaptoethanol kept under nitrogen mask and frozen at −20° C. Without wishing to be bound by theory, beta-mercaptoethanol provides a redox condition for proper iPSC health and growth into EBs in the 20% oxygen environment, which likely promotes production of toxic reactive oxygen species, in the incubator and any loss of its redox capacity due to improper storage conditions may impair proper development of organoids from EBs derived from iPSC.

100 units/ml penicillin 100 microgram/ml streptomycin 0.25 microgram/ml Fungizone DIFFERENTIATION MEDIA 3: DMEM/F12 media: Neurobasal media (1:1) supplemented with:

1:200 dilution N2 supplement o 1:100 dilution B27+ vitamin A 2.5 microgram/ml insulin 55 microM beta-mercaptoethanol kept under nitrogen mask and frozen at −20° C. Without intending to be bound by theory, beta-mercaptoethanol may contribute to the development of midbrain structures in brain organoids from EBs 100 units/ml penicillin 100 microgram/ml streptomycin 0.25 microgram/ml Fungizone melatonin

TSH

Equipment:

StemPro EZPassage (Invitrogen #23181-010) Without wishing to be bound by theory, the EZPassage tool cuts uniform squares of iPSCs which lead to more uniform iPSc colonies for subcloning. The uniformity enhances downstream homogeneity when making EBs.

Tissue Culture Flasks, 115 cm2 reclosable (TPP #TP90652)

Tissue Culture Flask, 150 cm2 reclosable (TPP #TP90552)

Lipidure coat plate, 96 wells, U-bottom (LCU96)

Lipidure coat MULTI dish, 24 well (510101619)

Parafilm (Sigma #P7793) Sterile Filtration Units for 150 ml/250 ml solutions (TPP99150, TPP99250)

Benchtop Tissue Culture Centrifuge CO2 incubator, maintained at 37° C. and 5% CO2

Example 3: Tuberous Sclerosis Complex Model

Tuberous sclerosis complex (TSC) is a genetic disorder that causes non-malignant tumors to form in many different organs, including the brain. TSC strongly impacts quality of life because patients have seizures, developmental delay, intellectual disability and autism. Two genes have been identified that can cause tuberous sclerosis complex. The TSC1 gene is located on chromosome 9 and is called the hamartin gene. The other gene, TSC2, is located on chromosome 16 and is called the tuberin gene.

We have derived a human brain organoid from iPSC cells derived from a patient with a gene variant of the TSC2 gene (ARG1743GLN) from iPSCs (Cat #GM25318 Coriell Institute Repository, NJ). This organoid serves as a genetic model of a tuberous sclerosis TSC2 mutant. Both normal and TSC2 mutant models were subject to genome wide transcriptomic analysis using the Ampliseq analysis to assess changes in gene expression and how well they correlated with known clinical pathology associated with TSC patients (FIG. 14).

The whole genome transcriptomic data shows that of all the genes expressed (~13,000), less than 1 dozen show >2-fold variance in the replicates for both WT and TSC2. This is additional supporting evidence for the robustness and replicability of our brain organoids derivation process at 1 week in culture. TS patients clinically have tumors typically in multiple organs including their brains, lungs, heart, kidneys and skin (Harmatomas). In the comparison of WT versus TSC2, the genes that show >2-fold to 300-fold difference, include those correlated with 1) tumor formation and 2) autism mapped using whole genome and exome sequencing strategies (SFARI site data base) (FIGS. 19 and 20).

FIG. 19 shows Ampliseq gene expression data for genes in the Simon Foundation (SFARI) data base compared between replicates of organoids from the TSC2 (Arg1743G1n) model (column 2 and 3) and the WT (normal) model (column 3 and 4). Highlighted are autism genes and genes associated with other clinical symptoms with fold change (column 5) and SFARI data base status or known tumor forming status.

Thus, the transcriptomic data correlates well with known clinical phenotypes of tumors, autism and other clinical symptoms in Tuberous Sclerosis patients and demonstrates the utility of the human brain organoid development model.

Example 4: Alzheimer's Disease APP1 Gene Duplication Human Brain Organoid Model Alzheimer's is a common form of dementia, associated with memory loss and other intellectual abilities that interfere with daily life. Alzheimer's disease accounts for 60 to 80 percent of dementia cases. Two abnormal structures called plaques and tangles are thought to damage and kill nerve cells. Plaques are deposits of a protein fragment called beta-amyloid that build up in the spaces between nerve cells. Tangles are twisted fibers of another protein called tau that build up inside cells.

A human brain organoid was generated from iPSC cells derived from a patient with a variant of the amyloid precursor protein (APP) gene in which the gene is duplicated from a 60 years old woman with early onset of AD. The iPSC was obtained from Coriell Institute in NJ.

The PSEN1 gene provides encodes a protein called presenilin 1. This protein is one part (subunit) of a complex called gamma- (γ-)secretase. Presenilin 1 carries out the major function of the complex, which is to cleave other proteins into smaller peptides by proteolysis, and presenilin 1 is described as the proteolytic subunit of γ-secretase.

The γ-secretase complex is located in the membrane that surrounds cells, where it cleaves many different proteins that span the cell membrane (transmembrane proteins). This cleavage is an important step in several chemical signaling pathways that transmit signals from outside the cell into the nucleus. One of these pathways, known as Notch signaling, is essential for the normal maturation and division of hair follicle cells and other types of skin cells. Notch signaling is also involved in normal immune system function.

The γ-secretase complex may be best known for its role in processing amyloid precursor protein (APP), which is made in the brain and other tissues. γ-secretase cuts APP into smaller peptides, including soluble amyloid precursor protein (sAPP) and several versions of amyloid-beta (β) peptide. Evidence suggests that sAPP has growth-promoting properties and may play a role in the formation of nerve cells (neurons) in the brain both before and after birth. Other functions of sAPP and amyloid-β peptide are under investigation.

The utility of the brain organoid model system was tested by engineering a genetic brain organoid model of an Alzheimer's patient with an APP mutation. Both normal and the APP mutant models were subject to whole genome transcriptomic analysis to assess changes in gene expression at 4 week in culture and how well they correlated with known clinical pathology associated with AD patients.

FIGS. 21A and 21B show the Ampliseq gene expression comparison for genes in SFARI database between replicates of organoids from the AD (APP) model (column 2 and 3) and the WT (normal) model (column 4 and 5) with fold change (column 6). These are representative examples of genes whose expression are dysregulated in the Alzeimer's Disease model.

The whole genome transcriptomic data shows that of all the genes expressed (~13,000 at 4 week in culture), only 1800 show >2-fold variance in the replicates for both WT and APP. This is additional supporting evidence for the robustness and replicability of the brain organoids derivation process.

In summary, because about eighteen hundreds of dysregulated genes map to databases dedicated to Alzheimer's disease, a new gene regulatory network perturbed by the APP mutation was identified as an "Alzheimer's network". The implications are that the hundreds of gene variants correlated with autism identified by genomics likely represent only a few Alzheimer's networks suggesting that identifying the nodes in these networks will vast simplify identifying therapeutic targets for AD.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An in vitro generated three-dimensional neural organoid derived from a human induced pluripotent stem cell (hIPSC), the organoid comprising: identifiable neural structures including a cerebral cortex, a cephalic flexure, and an optic stalk.

2. The neural organoid of claim 1, wherein the organoid comprises a cell expressing one or more neural markers and a cell expressing a marker selected from the group consisting of: astrocytic markers, oligodendrocyte markers, microglial markers, and/or vascular markers.

3. The neural organoid of claim 1, wherein the hIPSC comprises a genetic mutation associated with a neurological defect.

4. The neural organoid of claim 1, wherein the genetic mutation is in TSC1, TSC2, PSEN1, or APP.

5. An in vitro generated three-dimensional neural organoid derived from human induced pluripotent stem cells, the organoid comprising:

identifiable neural structures including a cerebral cortex, a cephalic flexure, and an optic stalk; and a mutation associated with a disease.

6. The neural organoid of claim 2, wherein the neural marker is a retinal marker selected from the group consisting of: retina specific Guanylate Cyclases (GUY2D, GUY2F), Retina And Anterior Neural Fold Homeobox (RAX), and retina specific Amine Oxidase, Copper Containing 2 (RAX).

7. The neural organoid of claim 2, wherein the neural marker is a cortical marker selected from the group consisting of: doublecortin, NeuN, FOXP2, CNTN4, and TBR1.

8. The neural organoid of claim 2, wherein the neural marker is a marker of dopaminergic neurons selected from the group consisting of: tyrosine hydroxylase, vesicular monoamine transporter 2 (VMAT2), dopamine active transporter (DAT) and Dopamine receptor $D_2$ (D2R).

9. The neural organoid of claim 2, wherein the neural marker is ATOH1, PAX6, SOX2, LHX2, GRID2, or another cerebellar marker.

10. The neural organoid of claim 2, wherein the neural marker is SOX2, NeuroD1, DCX, EMX2, FOXG1, PROX1, or another granule neuron marker.

11. The neural organoid of claim 2, wherein the neural marker is FGF8, INSM1, GATA2, ASCL1, GATA3, or another brain stem marker.

12. The neural organoid of claim 2, wherein the neural marker is a homeobox gene selected from the group consisting of: HOXA1, A2, A3, B4, A5, C8, or D13.

13. The neural organoid of claim 2, wherein the neural marker is NKCC1, KCC2, or another GABAergic marker.

14. The neural organoid of claim 2, wherein the astrocytic marker is GFAP, the oliogodendrocytic marker is OLIG2 or MBP, the microglia marker is AIF1 or CD4, and the vascular marker is NOS3.

15. The neural organoid of claim 1, wherein the neural organoid further comprises one or more additional neural regions.

16. The neural organoid of claim 15, wherein the one or more additional neural regions each express a marker of the brain stem, the cerebellum, the retina, the cortex, the midbrain, the hindbrain, or the spinal cord.

17. A method of screening a therapeutic agent, the method comprising:

(a) contacting the neural organoid of claim 1 with a therapeutic agent; and (b) detecting an alteration in the organoid in response to the therapeutic agent, wherein the organoid comprises identifiable neural structures including a cerebral cortex, a cephalic flexure, and an optic stalk.

18. The method of claim 17, wherein the alteration is an alteration in viability of the organoid compared to viability of an untreated control organoid; or an alteration in the expression of a neural marker compared to the expression of the neural marker of an untreated control organoid.

19. The method of claim 17, wherein the organoid comprises a genetic alteration associated with a disease.

20. The method of claim 19, wherein the genetic alteration is in a polynucleotide encoding a TSC1, TSC2, PSEN1, or APP polypeptide.

* * * * *

SEQUENCE LISTING

```
<160> NUMBER OF SEQ ID NOS: 7

<210> SEQ ID NO 1
<211> LENGTH: 746
<212> TYPE: PRT
<213> ORGANISM: Homo sapiens

<400> SEQUENCE: 1
```

```
Met Asp Gln Leu Glu Asp Leu Leu Val Leu Phe Ile Asn Tyr Val Pro
1               5                   10                  15

Thr Asp Gly Asn Ala Gly Leu Leu Ala Glu Pro Gln Ile Ala Met Phe
            20                  25                  30

Cys Gly Arg Leu Asn Met His Met Asn Val Gln Asn Gly Lys Trp Asp
        35                  40                  45

Ser Asp Pro Ser Gly Thr Lys Thr Cys Ile Asp Thr Lys Glu Gly Ile
    50                  55                  60

Leu Gln Tyr Cys Gln Glu Val Tyr Pro Glu Leu Gln Ile Thr Asn Val
65                  70                  75                  80

Val Glu Ala Asn Gln Pro Val Thr Ile Gln Asn Trp Cys Lys Arg Gly
                85                  90                  95

Arg Lys Gln Cys Lys Thr His Pro His Phe Val Ile Pro Tyr Arg Cys
            100                 105                 110

Leu Val Gly Glu Phe Val Ser Asp Ala Leu Leu Val Pro Asp Lys Cys
        115                 120                 125

Lys Phe Leu His Gln Glu Arg Met Asp Val Cys Glu Thr His Leu His
    130                 135                 140

Trp His Thr Val Ala Lys Glu Thr Cys Ser Glu Lys Ser Thr Asn Leu
145                 150                 155                 160

His Asp Tyr Gly Met Leu Leu Pro Cys Gly Ile Asp Lys Phe Arg Gly
                165                 170                 175

Val Glu Phe Val Cys Cys Pro Leu Ala Glu Glu Ser Asp Asn Val Asp
            180                 185                 190

Ser Ala Asp Ala Glu Glu Asp Asp Ser Asp Val Trp Trp Gly Gly Ala
        195                 200                 205

Asp Thr Asp Tyr Ala Asp Gly Ser Glu Asp Lys Val Val Glu Val Ala
    210                 215                 220

Glu Glu Glu Glu Val Ala Glu Val Glu Glu Glu Glu Ala Asp Asp Asp
225                 230                 235                 240

Glu Asp Asp Glu Asp Gly Asp Glu Val Glu Glu Glu Ala Glu Glu Pro
                245                 250                 255

Tyr Glu Glu Ala Thr Glu Arg Thr Thr Ser Ile Ala Thr Thr Thr Thr
            260                 265                 270

Thr Thr Thr Glu Ser Val Glu Glu Val Val Arg Glu Val Cys Ser Glu
        275                 280                 285

Gln Ala Glu Thr Gly Pro Cys Arg Ala Met Ile Ser Arg Trp Tyr Phe
    290                 295                 300

Asp Val Thr Glu Gly Lys Cys Ala Pro Phe Phe Tyr Gly Gly Cys Gly
305                 310                 315                 320

Gly Asn Arg Asn Asn Phe Asp Thr Glu Glu Tyr Cys Met Ala Val Cys
                325                 330                 335

Gly Ser Ala Ile Pro Thr Thr Ala Ala Ser Thr Pro Asp Ala Val Asp
            340                 345                 350

Lys Tyr Leu Glu Thr Pro Gly Asp Glu Asn Glu His Ala His Phe Gln
        355                 360                 365

Lys Ala Lys Glu Arg Leu Glu Ala Lys His Arg Glu Arg Met Ser Gln
    370                 375                 380

Val Met Arg Glu Trp Glu Glu Ala Glu Arg Gln Ala Lys Asn Leu Pro
385                 390                 395                 400

Lys Ala Asp Lys Lys Ala Val Ile Gln His Phe Gln Glu Lys Val Glu
                405                 410                 415
```

Ser Leu Glu Gln Glu Ala Ala Asn Glu Arg Gln Gln Leu Val Glu Thr
420 425 430

His Met Ala Arg Val Glu Ala Met Leu Asn Asp Arg Arg Arg Leu Ala
435 440 445

Leu Glu Asn Tyr Ile Thr Ala Leu Gln Ala Val Pro Pro Arg Pro Arg
450 455 460

His Val Phe Asn Met Leu Lys Lys Tyr Val Arg Ala Glu Gln Lys Asp
465 470 475 480

Arg Gln His Thr Leu Lys His Phe Glu His Val Arg Met Val Asp Pro
485 490 495

Lys Lys Ala Ala Gln Ile Arg Ser Gln Val Met Thr His Leu Arg Val
500 505 510

Ile Tyr Glu Arg Met Asn Gln Ser Leu Ser Leu Leu Tyr Asn Val Pro
515 520 525

Ala Val Ala Glu Glu Ile Gln Asp Glu Val Asp Glu Leu Leu Gln Lys
530 535 540

Glu Gln Asn Tyr Ser Asp Asp Val Leu Ala Asn Met Ile Ser Glu Pro
545 550 555 560

Arg Ile Ser Tyr Gly Asn Asp Ala Leu Met Pro Ser Leu Thr Glu Thr
565 570 575

Lys Thr Thr Val Glu Leu Leu Pro Val Asn Gly Glu Phe Ser Leu Asp
580 585 590

Asp Leu Gln Pro Trp His Ser Phe Gly Ala Asp Ser Val Pro Ala Asn
595 600 605

Thr Glu Asn Glu Val Glu Pro Val Asp Ala Arg Pro Ala Ala Asp Arg
610 615 620

Gly Leu Thr Thr Arg Pro Gly Ser Gly Leu Thr Asn Ile Lys Thr Glu
625 630 635 640

Glu Ile Ser Glu Val Lys Met Asp Ala Glu Phe Arg His Asp Ser Gly
645 650 655

Tyr Glu Val His His Gln Lys Leu Val Phe Phe Ala Glu Asp Val Gly
660 665 670

Ser Asn Lys Gly Ala Ile Ile Gly Leu Met Val Gly Gly Val Val Ile
675 680 685

Ala Thr Val Ile Val Ile Thr Leu Val Met Leu Lys Lys Lys Gln Tyr
690 695 700

Thr Ser Ile His His Gly Val Val Glu Val Asp Ala Ala Val Thr Pro
705 710 715 720

Glu Glu Arg His Leu Ser Lys Met Gln Gln Asn Gly Tyr Glu Asn Pro
725 730 735

Thr Tyr Lys Phe Phe Glu Gln Met Gln Asn
740 745

<210> SEQ ID NO 2
<211> LENGTH: 1164
<212> TYPE: PRT
<213> ORGANISM: Homo sapiens

<400> SEQUENCE: 2

Met Ala Gln Gln Ala Asn Val Gly Glu Leu Leu Ala Met Leu Asp Ser
1 5 10 15

Pro Met Leu Gly Val Arg Asp Asp Val Thr Ala Val Phe Lys Glu Asn
20 25 30

Leu Asn Ser Asp Arg Gly Pro Met Leu Val Asn Thr Leu Val Asp Tyr
35 40 45

-continued

```
Tyr Leu Glu Thr Ser Ser Gln Pro Ala Leu His Ile Leu Thr Thr Leu
    50                  55                  60

Gln Glu Pro His Asp Lys His Leu Leu Asp Arg Ile Asn Glu Tyr Val
65                  70                  75                  80

Gly Lys Ala Ala Thr Arg Leu Ser Ile Leu Ser Leu Leu Gly His Val
                85                  90                  95

Ile Arg Leu Gln Pro Ser Trp Lys His Lys Leu Ser Gln Ala Pro Leu
            100                 105                 110

Leu Pro Ser Leu Leu Lys Cys Leu Lys Met Asp Thr Asp Val Val Val
        115                 120                 125

Leu Thr Thr Gly Val Leu Val Leu Ile Thr Met Leu Pro Met Ile Pro
    130                 135                 140

Gln Ser Gly Lys Gln His Leu Leu Asp Phe Phe Asp Ile Phe Gly Arg
145                 150                 155                 160

Leu Ser Ser Trp Cys Leu Lys Lys Pro Gly His Val Ala Glu Val Tyr
                165                 170                 175

Leu Val His Leu His Ala Ser Val Tyr Ala Leu Phe His Arg Leu Tyr
            180                 185                 190

Gly Met Tyr Pro Cys Asn Phe Val Ser Phe Leu Arg Ser His Tyr Ser
        195                 200                 205

Met Lys Glu Asn Leu Glu Thr Phe Glu Glu Val Val Lys Pro Met Met
    210                 215                 220

Glu His Val Arg Ile His Pro Glu Leu Val Thr Gly Ser Lys Asp His
225                 230                 235                 240

Glu Leu Asp Pro Arg Arg Trp Lys Arg Leu Glu Thr His Asp Val Val
                245                 250                 255

Ile Glu Cys Ala Lys Ile Ser Leu Asp Pro Thr Glu Ala Ser Tyr Glu
            260                 265                 270

Asp Gly Tyr Ser Val Ser His Gln Ile Ser Ala Arg Phe Pro His Arg
        275                 280                 285

Ser Ala Asp Val Thr Thr Ser Pro Tyr Ala Asp Thr Gln Asn Ser Tyr
    290                 295                 300

Gly Cys Ala Thr Ser Thr Pro Tyr Ser Thr Ser Arg Leu Met Leu Leu
305                 310                 315                 320

Asn Met Pro Gly Gln Leu Pro Gln Thr Leu Ser Ser Pro Ser Thr Arg
                325                 330                 335

Leu Ile Thr Glu Pro Pro Gln Ala Thr Leu Trp Ser Pro Ser Met Val
            340                 345                 350

Cys Gly Met Thr Thr Pro Pro Thr Ser Pro Gly Asn Val Pro Pro Asp
        355                 360                 365

Leu Ser His Pro Tyr Ser Lys Val Phe Gly Thr Thr Ala Gly Gly Lys
    370                 375                 380

Gly Thr Pro Leu Gly Thr Pro Ala Thr Ser Pro Pro Pro Ala Pro Leu
385                 390                 395                 400

Cys His Ser Asp Asp Tyr Val His Ile Ser Leu Pro Gln Ala Thr Val
                405                 410                 415

Thr Pro Pro Arg Lys Glu Glu Arg Met Asp Ser Ala Arg Pro Cys Leu
            420                 425                 430

His Arg Gln His His Leu Leu Asn Asp Arg Gly Ser Glu Glu Pro Pro
        435                 440                 445

Gly Ser Lys Gly Ser Val Thr Leu Ser Asp Leu Pro Gly Phe Leu Gly
    450                 455                 460
```

-continued

```
Asp Leu Ala Ser Glu Glu Asp Ser Ile Glu Lys Asp Lys Glu Glu Ala
465                 470                 475                 480

Ala Ile Ser Arg Glu Leu Ser Glu Ile Thr Thr Ala Glu Ala Glu Pro
                485                 490                 495

Val Val Pro Arg Gly Gly Phe Asp Ser Pro Phe Tyr Arg Asp Ser Leu
            500                 505                 510

Pro Gly Ser Gln Arg Lys Thr His Ser Ala Ala Ser Ser Ser Gln Gly
        515                 520                 525

Ala Ser Val Asn Pro Glu Pro Leu His Ser Ser Leu Asp Lys Leu Gly
    530                 535                 540

Pro Asp Thr Pro Lys Gln Ala Phe Thr Pro Ile Asp Leu Pro Cys Gly
545                 550                 555                 560

Ser Ala Asp Glu Ser Pro Ala Gly Asp Arg Glu Cys Gln Thr Ser Leu
                565                 570                 575

Glu Thr Ser Ile Phe Thr Pro Ser Pro Cys Lys Ile Pro Pro Pro Thr
            580                 585                 590

Arg Val Gly Phe Gly Ser Gly Gln Pro Pro Pro Tyr Asp His Leu Phe
        595                 600                 605

Glu Val Ala Leu Pro Lys Thr Ala His His Phe Val Ile Arg Lys Thr
    610                 615                 620

Glu Glu Leu Leu Lys Lys Ala Lys Gly Asn Thr Glu Glu Asp Gly Val
625                 630                 635                 640

Pro Ser Thr Ser Pro Met Glu Val Leu Asp Arg Leu Ile Gln Gln Gly
                645                 650                 655

Ala Asp Ala His Ser Lys Glu Leu Asn Lys Leu Pro Leu Pro Ser Lys
            660                 665                 670

Ser Val Asp Trp Thr His Phe Gly Gly Ser Pro Pro Ser Asp Glu Ile
        675                 680                 685

Arg Thr Leu Arg Asp Gln Leu Leu Leu Leu His Asn Gln Leu Leu Tyr
    690                 695                 700

Glu Arg Phe Lys Arg Gln Gln His Ala Leu Arg Asn Arg Arg Leu Leu
705                 710                 715                 720

Arg Lys Val Ile Lys Ala Ala Ala Leu Glu Glu His Asn Ala Ala Met
                725                 730                 735

Lys Asp Gln Leu Lys Leu Gln Glu Lys Asp Ile Gln Met Trp Lys Val
            740                 745                 750

Ser Leu Gln Lys Glu Gln Ala Arg Tyr Asn Gln Leu Gln Glu Gln Arg
        755                 760                 765

Asp Thr Met Val Thr Lys Leu His Ser Gln Ile Arg Gln Leu Gln His
    770                 775                 780

Asp Arg Glu Glu Phe Tyr Asn Gln Ser Gln Glu Leu Gln Thr Lys Leu
785                 790                 795                 800

Glu Asp Cys Arg Asn Met Ile Ala Glu Leu Arg Ile Glu Leu Lys Lys
                805                 810                 815

Ala Asn Asn Lys Val Cys His Thr Glu Leu Leu Leu Ser Gln Val Ser
            820                 825                 830

Gln Lys Leu Ser Asn Ser Glu Ser Val Gln Gln Gln Met Glu Phe Leu
        835                 840                 845

Asn Arg Gln Leu Leu Val Leu Gly Glu Val Asn Glu Leu Tyr Leu Glu
    850                 855                 860

Gln Leu Gln Asn Lys His Ser Asp Thr Thr Lys Glu Val Glu Met Met
865                 870                 875                 880

Lys Ala Ala Tyr Arg Lys Glu Leu Glu Lys Asn Arg Ser His Val Leu
```

-continued

```
            885                 890                 895

Gln Gln Thr Gln Arg Leu Asp Thr Ser Gln Lys Arg Ile Leu Glu Leu
        900                 905                 910

Glu Ser His Leu Ala Lys Lys Asp His Leu Leu Leu Glu Gln Lys Lys
    915                 920                 925

Tyr Leu Glu Asp Val Lys Leu Gln Ala Arg Gly Gln Leu Gln Ala Ala
930                 935                 940

Glu Ser Arg Tyr Glu Ala Gln Lys Arg Ile Thr Gln Val Phe Glu Leu
945                 950                 955                 960

Glu Ile Leu Asp Leu Tyr Gly Arg Leu Glu Lys Asp Gly Leu Leu Lys
            965                 970                 975

Lys Leu Glu Glu Glu Lys Ala Glu Ala Ala Glu Ala Ala Glu Glu Arg
        980                 985                 990

Leu Asp Cys Cys Asn Asp Gly Cys  Ser Asp Ser Met Val  Gly His Asn
    995                 1000                1005

Glu Glu  Ala Ser Gly His Asn  Gly Glu Thr Lys Thr  Pro Arg Pro
    1010                1015                1020

Ser Ser  Ala Arg Gly Ser Ser  Gly Ser Arg Gly Gly  Gly Gly Ser
    1025                1030                1035

Ser Ser  Ser Ser Ser Glu Leu  Ser Thr Pro Glu Lys  Pro Pro His
    1040                1045                1050

Gln Arg  Ala Gly Pro Phe Ser  Ser Arg Trp Glu Thr  Thr Met Gly
    1055                1060                1065

Glu Ala  Ser Ala Ser Ile Pro  Thr Thr Val Gly Ser  Leu Pro Ser
    1070                1075                1080

Ser Lys  Ser Phe Leu Gly Met  Lys Ala Arg Glu Leu  Phe Arg Asn
    1085                1090                1095

Lys Ser  Glu Ser Gln Cys Asp  Glu Asp Gly Met Thr  Ser Ser Leu
    1100                1105                1110

Ser Glu  Ser Leu Lys Thr Glu  Leu Gly Lys Asp Leu  Gly Val Glu
    1115                1120                1125

Ala Lys  Ile Pro Leu Asn Leu  Asp Gly Pro His Pro  Ser Pro Pro
    1130                1135                1140

Thr Pro  Asp Ser Val Gly Gln  Leu His Ile Met Asp  Tyr Asn Glu
    1145                1150                1155

Thr His  His Glu His Ser
    1160


<210> SEQ ID NO 3
<211> LENGTH: 8626
<212> TYPE: DNA
<213> ORGANISM: Homo sapiens

<400> SEQUENCE: 3

acgacggggg aggtgctgta cgtccaagat ggcggcgccc tgtaggctgg agggactgtg      60

aggtaaacag ctgaggggga ggagacggtg gtgaccatga aagacaccag gttgacagca     120

ctggaaactg aagtaccagt tgtcgctaga acagtttggt agtggcccca atgaagaacc     180

ttcagaacct gtagcacacg tcctggagcc agcacagcgc cttcgagcga gagaatggcc     240

caacaagcaa atgtcgggga gcttcttgcc atgctggact cccccatgct gggtgtgcgg     300

gacgacgtga cagctgtctt taaagagaac ctcaattctg accgtggccc tatgcttgta     360

aacaccttgg tggattatta cctggaaacc agctctcagc cggcattgca catcctgacc     420

accttgcaag agccacatga caagcacctc ttggacagga ttaacgaata tgtgggcaaa     480
```

gccgccactc gtttatccat cctctcgtta ctgggtcatg tcataagact gcagccatct 540
tggaagcata agctctctca agcacctctt ttgccttctt tactaaaatg tctcaagatg 600
gacactgacg tcgttgtcct cacaacaggc gtcttggtgt tgataaccat gctaccaatg 660
attccacagt ctgggaaaca gcatcttctt gatttctttg acatttttgg ccgtctgtca 720
tcatggtgcc tgaagaaacc aggccacgtg gcggaagtct atctcgtcca tctccatgcc 780
agtgtgtacg cactctttca tcgcctttat ggaatgtacc cttgcaactt cgtctccttt 840
ttgcgttctc attacagtat gaaagaaaac ctggagactt ttgaagaagt ggtcaagcca 900
atgatggagc atgtgcgaat tcatccggaa ttagtgactg gatccaagga ccatgaactg 960
gaccctcgaa ggtggaagag attagaaact catgatgttg tgatcgagtg tgccaaaatc 1020
tctctggatc ccacagaagc ctcatatgaa gatggctatt ctgtgtctca ccaaatctca 1080
gcccgctttc ctcatcgttc agccgatgtc accaccagcc cttatgctga cacacagaat 1140
agctatgggt gtgctacttc taccccttac tccacgtctc ggctgatgtt gttaaatatg 1200
ccagggcagc tacctcagac tctgagttcc ccatcgacac ggctgataac tgaaccacca 1260
caagctactc tttggagccc atctatggtt tgtggtatga ccactcctcc aacttctcct 1320
ggaaatgtcc cacctgatct gtcacaccct tacagtaaag tctttggtac aactgcaggt 1380
ggaaaaggaa ctcctctggg aaccccagca acctctcctc ctccagcccc actctgtcat 1440
tcggatgact acgtgcacat ttcactcccc caggccacag tcacaccccc caggaaggaa 1500
gagagaatgg attctgcaag accatgtcta cacagacaac accatcttct gaatgacaga 1560
ggatcagaag agccacctgg cagcaaaggt tctgtcactc taagtgatct tccagggttt 1620
ttaggtgatc tggcctctga agaagatagt attgaaaaag ataaagaaga agctgcaata 1680
tctagagaac tttctgagat caccacagca gaggcagagc ctgtggttcc tcgaggaggc 1740
tttgactctc ccttttaccg agacagtctc ccaggttctc agcggaagac ccactcggca 1800
gcctccagtt ctcagggcgc cagcgtgaac cctgagcctt tacactcctc cctggacaag 1860
cttgggcctg acacaccaaa gcaagccttt actcccatag acctgccctg cggcagtgct 1920
gatgaaagcc ctgcgggaga cagggaatgc cagacttctt tggagaccag tatcttcact 1980
cccagtcctt gtaaaattcc acctccgacg agagtgggct ttggaagcgg gcagcctccc 2040
ccgtatgatc atctttttga ggtggcattg ccaaagacag cccatcattt tgtcatcagg 2100
aagactgagg agctgttaaa gaaagcaaaa ggaaacacag aggaagatgg tgtgccctct 2160
acctccccaa tggaagtgct ggacagactg atacagcagg gagcagacgc gcacagcaag 2220
gagctgaaca agttgccttt acccagcaag tctgtcgact ggacccactt tggaggctct 2280
cctccttcag atgagatccg caccctccga gaccagttgc ttttactgca caaccagtta 2340
ctctatgagc gttttaagag gcagcagcat gccctccgga acaggcggct cctccgcaag 2400
gtgatcaaag cagcagctct ggaggaacat aatgctgcca tgaaagatca gttgaagtta 2460
caagagaagg acatccagat gtggaaggtt agtctgcaga aagaacaagc tagatacaat 2520
cagctccagg agcagcgtga cactatggta accaagctcc acagccagat cagacagctg 2580
cagcatgacc gagaggaatt ctacaaccag agccaggaat tacagacgaa gctggaggac 2640
tgcaggaaca tgattgcgga gctgcggata gaactgaaga aggccaacaa caaggtgtgt 2700
cacactgagc tgctgctcag tcaggtttcc caaaagctct caaacagtga gtcggtccag 2760
cagcagatgg agttcttgaa caggcagctg ttggttcttg gggaggtcaa cgagctctat 2820

```
ttggaacaac tgcagaacaa gcactcagat accacaaagg aagtagaaat gatgaaagcc   2880
gcctatcgga aagagctaga aaaaaacaga agccatgttc tccagcagac tcagaggctt   2940
gatacctccc aaaaacggat tttggaactg gaatctcacc tggccaagaa agaccacctt   3000
cttttggaac agaagaaata tctagaggat gtcaaactcc aggcaagagg acagctgcag   3060
gccgcagaga gcaggtatga ggctcagaaa aggataaccc aggtgtttga attggagatc   3120
ttagatttat atggcaggtt ggagaaagat ggcctcctga aaaaacttga agaagaaaaa   3180
gcagaagcag ctgaagcagc agaagaaagg cttgactgtt gtaatgacgg gtgctcagat   3240
tccatggtag ggcacaatga agaggcatct ggccacaacg gtgagaccaa gacccccagg   3300
cccagcagcg cccggggcag tagtggaagc agaggtggtg gaggcagcag cagcagcagc   3360
agcgagcttt ctaccccaga gaaaccccca caccagaggg caggcccatt cagcagtcgg   3420
tgggagacga ctatgggaga agcgtctgcc agcatcccca ccactgtggg ctcacttccc   3480
agttcaaaaa gcttcctggg tatgaaggct cgagagttat ttcgtaataa gagcgagagc   3540
cagtgtgatg aggacggcat gaccagtagc ctttctgaga gcctaaagac agaactgggc   3600
aaagacttgg gtgtggaagc caagattccc ctgaacctag atggccctca cccgtctccc   3660
ccgaccccgg acagtgttgg acagctacat atcatggact acaatgagac tcatcatgaa   3720
cacagctaag gaatgatggt caatcagtgt taacttgcat attgttggca cagaacagga   3780
ggtgtgaatg cacgtttcaa agctttcctg tttccagggt ctgagtgcaa gttcatgtgt   3840
ggaaatggga cggaggtcct ttggacagct gactgaatgc agaacggttt ttggatctgg   3900
cattgaaatg cctcttgacc ttcccctcca cccgccctaa ccccctctca tttacctcgc   3960
agtgtgttct aatccaaggg ccagttggtg ttcctcagta gctttacttt cttcctttcc   4020
cccccaaatg gttgcgtcct ttgaacctgt gcaatatgag gccaaattta atctttgagt   4080
ctaacacacc actttctgct ttcccgaagt tcagataact gggttggctc tcaattagac   4140
caggtagttt gttgcattgc aggtaagtct ggttttgtcc cttccaggag gacatagcct   4200
gcaaagctgg ttgtctttac atgaaagcgt ttacatgaga ctttccgact gctttttga    4260
ttctgaagtt cagcatctaa agcagcaggt ctagaagaac aacggtttat tcatacttgc   4320
attcttttgg cagttctgat aagcttccta gaaagttctg tgtaaacaga agcctgtttc   4380
agaaatctgg agctggcact gtggagacca cacacccttt gggaaagctc ttgtctcttc   4440
ttcccccact acctcttatt tatttggtgt ttgcttgaat gctggtacta ttgtgaccac   4500
aggctggtgt gtaggtggta aaacctgttc tccataggag ggaaggagca gtcactggga   4560
gaggttaccc gagaagcact tgagcatgag gaactgcacc tttaggccat ctcagcttgc   4620
tgggcctttt gttaaaccct tctgtctact ggcctccctt tgtgtgcata cgcctcttgt   4680
tcatgtcagc ttatatgtga cactgcagca gaaaggctct gaaggtccaa agagtttctg   4740
caaagtgtat gtgaccatca tttcccaggc cattagggtt gcctcactgt agcaggttct   4800
aggctaccag aagaggggca gctttttcat accaattcca actttcaggg gctgactctc   4860
cagggagctg atgtcatcac actctccatg ttagtaatgg cagagcagtc taaacagagt   4920
ccgggagaat gctggcaaag gctggctgtg tatacccact aggctgcccc acgtgctccc   4980
gagagatgac actagtcaga aaattggcag tggcagagaa tccaaactca acaagtgctc   5040
ctgaaagaaa cgctagaagc ctaagaactg tggtctggtg ttccagctga ggcaggggga   5100
tttggtagga aggagccagt gaacttggct ttcctgtttc tatctttcat taaaaagaat   5160
agaaggattc agtcataaag aggtaaaaaa ctgtcacggt acgaaatctt agtgcccacg   5220
```

```
gaggcctcga gcagagagaa tgaaagtctt tttttttttt tttttttttt agcatggcaa   5280
taaatattct agcatcccta actaaagggg actagacagt tagagactct gtcaccctag   5340
ctataccagc agaaaacctg ttcaggcagg ctttctgggt gtgactgatt cccagcctgt   5400
ggcagggcgt ggtcccaact actcagccta gcacaggctg gcagttggta ctgaattgtc   5460
agatgtggag tattagtgac accacacatt taattcagct ttgtccaaag gaaagcttaa   5520
aacccaatac agtctagttt cctggttccg ttttagaaaa ggaaaacgtg aacaaactta   5580
gaaagggaag gaaatcccat cagtgaatcc tgaaactggt tttaagtgct ttccttctcc   5640
tcatgcccaa gagatctgtg ccatagaaca agataccagg cacttaaagc cttttcctga   5700
attggaaagg aaaagaggcc caagtgcaaa agaaaaaaca ttttagaaac ggacagctta   5760
taaaaataaa gggaagaaag gaggcagcat ggagagaggc ctgtgctaga agctccatgg   5820
acgtgtctgc acagggtcct cagctcatcc atgcggcctg ggtgtccttt tactcagctt   5880
tataacaaat gtggctccaa gctcaggtgc ctttgagttc taggaggctg tgggttttat   5940
tcaactacgg ttgggagaat gagacctgga gtcatgttga aggtgcccaa cctaaaaatg   6000
taggctttca tgttgcaaag aactccagag tcagtagtta ggtttggttt ggttttggac   6060
atgataaacc tgccaagagt caacaggtca cttgatcatg ctgcagtggg tagttctaag   6120
gatggaaagg tgacagtatt actctcgaga ggcaattcag tcctgggcaa aggtattagt   6180
acaataagcg ttaagggcag agtctacctt gaaaccaatt aagcagcttg gtattcataa   6240
atattgggat tggatggcct ccatccagaa atcactatgg gtgagcatac ctgtctcagc   6300
tgtttggcca atgtgcataa cctactcgga tccccacctg acactaacca gagtcagcac   6360
aggccccgag gagcccgaag tctgctgctg tgcagcatgg aattccttta aaaaggtgca   6420
ctacagtttt agcggggagg gggataggaa gacgcagagc aaatgagctc cggagtccct   6480
gcaggtgaat aaacacacag atctgcatct gatagaactt tgatggattt tcaaaaagcc   6540
gttgacaagg ctctgctata cagtctataa aaattgttat tatgggattg gaagaaacac   6600
gtggtcatga atagaaaaaa aacaaaccca aaggtaggaa ggtcaaggtc atttcttaga   6660
tggagaagtt gtgaaagatg tccttggaga tgagttttag gaccagcatt actaaggcag   6720
gtgggcagac agtgacctct ctaggtgtgt ccacagagtt tttcaggaga gaaaactgcc   6780
tgacctttgg gactaagctg cggaatcttc ttactaagct tgaagagtgg agaggcgaga   6840
ggtgagctac tttgtgagcc aaagcttatg tgacatggtt ggggaaacag tccaaactgt   6900
tctgagaagg tgaactgtta cgacccagga caattagaaa aattcaccca ccatgccgca   6960
cattactggg taaaagcagg gcagcaggga acaaaactcc agactcttgg gccgtcccca   7020
tttgcaacag cacacatagt ttctggtata tttgttggga aagataaaac tctagcagtt   7080
gttgagggga ggatgtataa aatggtcatg gggatgaaag gatctctgag accacagagg   7140
ctcagactca ctgttaagaa tagaaaactg ggtatgcgtt tcatgtagcc agcagaactg   7200
aagtgtgctg tgacaagcca atgtgaattt ctaccaaata gtagagcata ccacttgaag   7260
aaggaaagaa ccgaagagca aacaaaagtt ctgcgtaatg agactcacct tttctcgctg   7320
aaagcactaa gaggtgggag gaggcctgca caggctggag gagggtttgg gcagagcgaa   7380
gacccggcca ggaccttggt gagatggggt gccgcccacc tcctgcggat actcttggag   7440
agttgttccc ccagggggct ctgccccacc tggagaagga agctgcctgg tgtggagtga   7500
ctcaaatcag tatacctatc tgctgcacct tcactctcca gggtacatgc tttaaaaccg   7560
```

```
acccgcaaca agtattggaa aaatgtatcc agtctgaaga tgtttgtgta tctgtttaca   7620
tccagagttc tgtgacacat gccccccaga ttgctgcaaa gatcccaagg cattgattgc   7680
acttgattaa gcttttgtct gtaggtgaaa gaacaagttt aggtcgagga ctggccccta   7740
ggctgctgct gtgacccttg tcccatgtgg cttgtttgcc tgtccgggac tcttcgatgt   7800
gcccagggga gcgtgttcct gtctcttcca tgccgtcctg cagtccttat ctgctcgcct   7860
gagggaagag tagctgtagc tacaagggaa gcctgcctgg aagagccgag cacctgtgcc   7920
catggcttct ggtcatgaaa cgagttaatg atggcagagg agcttcctcc ccacttcgca   7980
gcgccacatt atccatcctc tgagataagt aggctggttt aaccattgga atggaccttt   8040
cagtggaaac cctgagagtc tgagaacccc cagaccaacc cttccctccc tttccccacc   8100
tcttacagtg tttggacagg agggtatggt gctgctctgt gtagcaagta ctttggctta   8160
tgaaagaggc agccacgcat tttgcactag gaagaatcag taatcacttt tcagaagact   8220
tctatggacc acaaatatat tacggaggaa cagattttgc taagacataa tctagtttta   8280
taactcaatc atgaatgaac catgtgtggc aaacttgcag tttaaagggg tcccatcagt   8340
gaaagaaact gatttttttt aacggactgc ttttagttaa attgaagaaa gtcagctctt   8400
gtcaaaaggt ctaaactttc ccgcctcaat cctaaaagca tgtcaacaat ccacatcaga   8460
tgccataaat atgaactgca ggataaaatg gtacaatctt agtgaatggg aattggaatc   8520
aaaagagttt gctgtccttc ttagaatgtt ctaaaatgtc aaggcagttg cttgtgttta   8580
actgtgaaca aataaaaatt tattgttttg cactacaaaa aaaaaa                  8626
```

```
<210> SEQ ID NO 4
<211> LENGTH: 1807
<212> TYPE: PRT
<213> ORGANISM: Homo sapiens

<400> SEQUENCE: 4

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
    50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190
```

-continued

```
Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
        355                 360                 365

Leu Gln Gln Leu Gln Thr Leu Asp Ser Pro Glu Leu Arg Thr Ile Val
    370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Ala Leu
        435                 440                 445

Met Glu Arg Phe Phe Arg Ser Glu Ser Arg Gly Ala Val Arg Ile Lys
    450                 455                 460

Val Leu Asp Val Leu Ser Phe Val Leu Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Pro Glu
    530                 535                 540

Leu Glu Glu Arg Asp Val Ala Ala Tyr Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Met Leu Val Ser
            580                 585                 590

His Ile Gln Leu His Tyr Lys His Ser Tyr Thr Leu Pro Ile Ala Ser
        595                 600                 605
```

```
Ser Ile Arg Leu Gln Ala Phe Asp Phe Leu Leu Leu Leu Arg Ala Asp
    610                 615                 620

Ser Leu His Arg Leu Gly Leu Pro Asn Lys Asp Gly Val Val Arg Phe
625                 630                 635                 640

Ser Pro Tyr Cys Val Cys Asp Tyr Met Glu Pro Glu Arg Gly Ser Glu
                645                 650                 655

Lys Lys Thr Ser Gly Pro Leu Ser Pro Pro Thr Gly Pro Pro Gly Pro
            660                 665                 670

Ala Pro Ala Gly Pro Ala Val Arg Leu Gly Ser Val Pro Tyr Ser Leu
        675                 680                 685

Leu Phe Arg Val Leu Leu Gln Cys Leu Lys Gln Glu Ser Asp Trp Lys
    690                 695                 700

Val Leu Lys Leu Val Leu Gly Arg Leu Pro Glu Ser Leu Arg Tyr Lys
705                 710                 715                 720

Val Leu Ile Phe Thr Ser Pro Cys Ser Val Asp Gln Leu Cys Ser Ala
                725                 730                 735

Leu Cys Ser Met Leu Ser Gly Pro Lys Thr Leu Glu Arg Leu Arg Gly
            740                 745                 750

Ala Pro Glu Gly Phe Ser Arg Thr Asp Leu His Leu Ala Val Val Pro
        755                 760                 765

Val Leu Thr Ala Leu Ile Ser Tyr His Asn Tyr Leu Asp Lys Thr Lys
    770                 775                 780

Gln Arg Glu Met Val Tyr Cys Leu Glu Gln Gly Leu Ile His Arg Cys
785                 790                 795                 800

Ala Ser Gln Cys Val Val Ala Leu Ser Ile Cys Ser Val Glu Met Pro
                805                 810                 815

Asp Ile Ile Ile Lys Ala Leu Pro Val Leu Val Val Lys Leu Thr His
            820                 825                 830

Ile Ser Ala Thr Ala Ser Met Ala Val Pro Leu Leu Glu Phe Leu Ser
        835                 840                 845

Thr Leu Ala Arg Leu Pro His Leu Tyr Arg Asn Phe Ala Ala Glu Gln
    850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Phe Ile
            900                 905                 910

Thr Lys Gly Leu Arg Ser Asn Val Leu Leu Ser Phe Asp Asp Thr Pro
        915                 920                 925

Glu Lys Asp Ser Phe Arg Ala Arg Ser Thr Ser Leu Asn Glu Arg Pro
    930                 935                 940

Lys Ser Leu Arg Ile Ala Arg Pro Pro Lys Gln Gly Leu Asn Asn Ser
945                 950                 955                 960

Pro Pro Val Lys Glu Phe Lys Glu Ser Ser Ala Ala Glu Ala Phe Arg
                965                 970                 975

Cys Arg Ser Ile Ser Val Ser Glu His Val Val Arg Ser Arg Ile Gln
            980                 985                 990

Thr Ser Leu Thr Ser Ala Ser Leu  Gly Ser Ala Asp Glu  Asn Ser Val
        995                 1000                 1005

Ala Gln  Ala Asp Asp Ser Leu  Lys Asn Leu His Leu  Glu Leu Thr
    1010                 1015                 1020

Glu Thr  Cys Leu Asp Met Met  Ala Arg Tyr Val Phe  Ser Asn Phe
```

```
    1025                1030                1035

Thr Ala  Val Pro Lys Arg Ser  Pro Val Gly Glu Phe  Leu Leu Ala
    1040                1045                1050

Gly Gly  Arg Thr Lys Thr Trp  Leu Val Gly Asn Lys  Leu Val Thr
    1055                1060                1065

Val Thr  Thr Ser Val Gly Thr  Gly Thr Arg Ser Leu  Leu Gly Leu
    1070                1075                1080

Asp Ser  Gly Glu Leu Gln Ser  Gly Pro Glu Ser Ser  Ser Ser Pro
    1085                1090                1095

Gly Val  His Val Arg Gln Thr  Lys Glu Ala Pro Ala  Lys Leu Glu
    1100                1105                1110

Ser Gln  Ala Gly Gln Gln Val  Ser Arg Gly Ala Arg  Asp Arg Val
    1115                1120                1125

Arg Ser  Met Ser Gly Gly His  Gly Leu Arg Val Gly  Ala Leu Asp
    1130                1135                1140

Val Pro  Ala Ser Gln Phe Leu  Gly Ser Ala Thr Ser  Pro Gly Pro
    1145                1150                1155

Arg Thr  Ala Pro Ala Ala Lys  Pro Glu Lys Ala Ser  Ala Gly Thr
    1160                1165                1170

Arg Val  Pro Val Gln Glu Lys  Thr Asn Leu Ala Ala  Tyr Val Pro
    1175                1180                1185

Leu Leu  Thr Gln Gly Trp Ala  Glu Ile Leu Val Arg  Arg Pro Thr
    1190                1195                1200

Gly Asn  Thr Ser Trp Leu Met  Ser Leu Glu Asn Pro  Leu Ser Pro
    1205                1210                1215

Phe Ser  Ser Asp Ile Asn Asn  Met Pro Leu Gln Glu  Leu Ser Asn
    1220                1225                1230

Ala Leu  Met Ala Ala Glu Arg  Phe Lys Glu His Arg  Asp Thr Ala
    1235                1240                1245

Leu Tyr  Lys Ser Leu Ser Val  Pro Ala Ala Ser Thr  Ala Lys Pro
    1250                1255                1260

Pro Pro  Leu Pro Arg Ser Asn  Thr Val Ala Ser Phe  Ser Ser Leu
    1265                1270                1275

Tyr Gln  Ser Ser Cys Gln Gly  Gln Leu His Arg Ser  Val Ser Trp
    1280                1285                1290

Ala Asp  Ser Ala Val Val Met  Glu Glu Gly Ser Pro  Gly Glu Val
    1295                1300                1305

Pro Val  Leu Val Glu Pro Pro  Gly Leu Glu Asp Val  Glu Ala Ala
    1310                1315                1320

Leu Gly  Met Asp Arg Arg Thr  Asp Ala Tyr Ser Arg  Ser Ser Ser
    1325                1330                1335

Val Ser  Ser Gln Glu Glu Lys  Ser Leu His Ala Glu  Glu Leu Val
    1340                1345                1350

Gly Arg  Gly Ile Pro Ile Glu  Arg Val Val Ser Ser  Glu Gly Gly
    1355                1360                1365

Arg Pro  Ser Val Asp Leu Ser  Phe Gln Pro Ser Gln  Pro Leu Ser
    1370                1375                1380

Lys Ser  Ser Ser Ser Pro Glu  Leu Gln Thr Leu Gln  Asp Ile Leu
    1385                1390                1395

Gly Asp  Pro Gly Asp Lys Ala  Asp Val Gly Arg Leu  Ser Pro Glu
    1400                1405                1410

Val Lys  Ala Arg Ser Gln Ser  Gly Thr Leu Asp Gly  Glu Ser Ala
    1415                1420                1425
```

```
Ala Trp Ser Ala Ser Gly Glu Asp Ser Arg Gly Gln Pro Glu Gly
    1430                1435                1440

Pro Leu Pro Ser Ser Ser Pro Arg Ser Pro Ser Gly Leu Arg Pro
    1445                1450                1455

Arg Gly Tyr Thr Ile Ser Asp Ser Ala Pro Ser Arg Arg Gly Lys
    1460                1465                1470

Arg Val Glu Arg Asp Ala Leu Lys Ser Arg Ala Thr Ala Ser Asn
    1475                1480                1485

Ala Glu Lys Val Pro Gly Ile Asn Pro Ser Phe Val Phe Leu Gln
    1490                1495                1500

Leu Tyr His Ser Pro Phe Phe Gly Asp Glu Ser Asn Lys Pro Ile
    1505                1510                1515

Leu Leu Pro Asn Glu Ser Gln Ser Phe Glu Arg Ser Val Gln Leu
    1520                1525                1530

Leu Asp Gln Ile Pro Ser Tyr Asp Thr His Lys Ile Ala Val Leu
    1535                1540                1545

Tyr Val Gly Glu Gly Gln Ser Asn Ser Glu Leu Ala Ile Leu Ser
    1550                1555                1560

Asn Glu His Gly Ser Tyr Arg Tyr Thr Glu Phe Leu Thr Gly Leu
    1565                1570                1575

Gly Arg Leu Ile Glu Leu Lys Asp Cys Gln Pro Asp Lys Val Tyr
    1580                1585                1590

Leu Gly Gly Leu Asp Val Cys Gly Glu Asp Gly Gln Phe Thr Tyr
    1595                1600                1605

Cys Trp His Asp Asp Ile Met Gln Ala Val Phe His Ile Ala Thr
    1610                1615                1620

Leu Met Pro Thr Lys Asp Val Asp Lys His Arg Cys Asp Lys Lys
    1625                1630                1635

Arg His Leu Gly Asn Asp Phe Val Ser Ile Val Tyr Asn Asp Ser
    1640                1645                1650

Gly Glu Asp Phe Lys Leu Gly Thr Ile Lys Gly Gln Phe Asn Phe
    1655                1660                1665

Val His Val Ile Val Thr Pro Leu Asp Tyr Glu Cys Asn Leu Val
    1670                1675                1680

Ser Leu Gln Cys Arg Lys Asp Met Glu Gly Leu Val Asp Thr Ser
    1685                1690                1695

Val Ala Lys Ile Val Ser Asp Arg Asn Leu Pro Phe Val Ala Arg
    1700                1705                1710

Gln Met Ala Leu His Ala Asn Met Ala Ser Gln Val His His Ser
    1715                1720                1725

Arg Ser Asn Pro Thr Asp Ile Tyr Pro Ser Lys Trp Ile Ala Arg
    1730                1735                1740

Leu Arg His Ile Lys Arg Leu Arg Gln Arg Ile Cys Glu Glu Ala
    1745                1750                1755

Ala Tyr Ser Asn Pro Ser Leu Pro Leu Val His Pro Pro Ser His
    1760                1765                1770

Ser Lys Ala Pro Ala Gln Thr Pro Ala Glu Pro Thr Pro Gly Tyr
    1775                1780                1785

Glu Val Gly Gln Arg Lys Arg Leu Ile Ser Ser Val Glu Asp Phe
    1790                1795                1800

Thr Glu Phe Val
    1805
```

<210> SEQ ID NO 5
<211> LENGTH: 5751
<212> TYPE: DNA
<213> ORGANISM: Homo sapiens

<400> SEQUENCE: 5
tttccgccag agggcggcac agaactacaa ctcccagcaa gctcccaagg cggccctccg 60
cgcaatgccg ctaccggaag tgcgggtcgc gcttccggcg gcgtcccggg gccagggggg 120
tgcgcctttc tccgcgtcgg ggcggcccgg agcgcggtgg cgcggcgcgg gaggggtttt 180
ctggtgcgtc ctggtccacc atggccaaac caacaagcaa agattcaggc ttgaaggaga 240
agtttaagat tctgttggga ctgggaacac cgaggccaaa tcccaggtct gcagagggta 300
aacagacgga gtttatcatc accgcggaaa tactgagaga actgagcatg gaatgtggcc 360
tcaacaatcg catccggatg atagggcaga tttgtgaagt cgcaaaaacc aagaaatttg 420
aagagcacgc agtggaagca ctctggaagg cggtcgcgga tctgttgcag ccggagcggc 480
cgctggaggc ccggcacgcg gtgctggctc tgctgaaggc catcgtgcag gggcagggcg 540
agcgtttggg ggtcctcaga gccctcttct ttaaggtcat caaggattac ccttccaacg 600
aagaccttca cgaaaggctg gaggttttca aggccctcac agacaatggg agacacatca 660
cctacttgga ggaagagctg gctgactttg tcctgcagtg gatggatgtt ggcttgtcct 720
cggaattcct tctggtgctg gtgaacttgg tcaaattcaa tagctgttac ctcgacgagt 780
acatcgcaag gatggttcag atgatctgtc tgctgtgcgt ccggaccgcg tcctctgtgg 840
acatagaggt ctccctgcag gtgctggacg ccgtggtctg ctacaactgc ctgccggctg 900
agagcctccc gctgttcatc gttaccctct gtcgcaccat caacgtcaag gagctctgcg 960
agccttgctg gaagctgatg cggaacctcc ttggcaccca cctgggccac agcgccatct 1020
acaacatgtg ccacctcatg gaggacagag cctacatgga ggacgcgccc ctgctgagag 1080
gagccgtgtt ttttgtgggc atggctctct ggggagccca ccggctctat tctctcagga 1140
actcgccgac atctgtgttg ccatcatttt accaggccat ggcatgtccg aacgaggtgg 1200
tgtcctatga gatcgtcctg tccatcacca ggctcatcaa gaagtatagg aaggagctcc 1260
aggtggtggc gtgggacatt ctgctgaaca tcatcgaacg gctccttcag cagctccaga 1320
ccttggacag cccggagctc aggaccatcg tccatgacct gttgaccacg gtggaggagc 1380
tgtgtgacca gaacgagttc cacgggtctc aggagagata ctttgaactg gtggagagat 1440
gtgcggacca gaggcctgag tcctccctcc tgaacctgat ctcctataga gcgcagtcca 1500
tccacccggc caaggacggc tggattcaga acctgcaggc gctgatggag agattcttca 1560
ggagcgagtc ccgaggcgcc gtgcgcatca aggtgctgga cgtgctgtcc tttgtgctgc 1620
tcatcaacag gcagttctat gaggaggagc tgattaactc agtggtcatc tcgcagctct 1680
cccacatccc cgaggataaa gaccaccagg tccgaaagct ggccacccag ttgctggtgg 1740
acctggcaga gggctgccac acacaccact tcaacagcct gctggacatc atcgagaagg 1800
tgatggcccg ctccctctcc ccacccccgg agctggaaga aagggatgtg gccgcatact 1860
cggcctcctt ggaggatgtg aagacagccg tcctggggct tctggtcatc cttcagacca 1920
agctgtacac cctgcctgca agccacgcca cgcgtgtgta tgagatgctg gtcagccaca 1980
ttcagctcca ctacaagcac agctacaccc tgccaatcgc gagcagcatc cggctgcagg 2040
cctttgactt cctgttgctg ctgcgggccg actcactgca ccgcctgggc ctgcccaaca 2100
aggatggagt cgtgcggttc agcccctact gcgtctgcga ctacatggag ccagagagag 2160
gctctgagaa gaagaccagc ggccccccttt ctcctcccac agggcctcct ggcccggcgc 2220
ctgcaggccc cgccgtgcgg ctggggtccg tgccctactc cctgctcttc cgcgtcctgc 2280
tgcagtgctt gaagcaggag tctgactgga aggtgctgaa gctggttctg ggcaggctgc 2340
ctgagtccct gcgctataaa gtgctcatct ttacttcccc ttgcagtgtg gaccagctgt 2400
gctctgctct ctgctccatg ctttcaggcc caaagacact ggagcggctc cgaggcgccc 2460
cagaaggctt ctccagaact gacttgcacc tggccgtggt tccagtgctg acagcattaa 2520
tctcttacca taactacctg gacaaaacca aacagcgcga gatggtctac tgcctggagc 2580
agggcctcat ccaccgctgt gccagccagt gcgtcgtggc cttgtccatc tgcagcgtgg 2640
agatgcctga catcatcatc aaggcgctgc ctgttctggt ggtgaagctc acgcacatct 2700
cagccacagc cagcatggcc gtcccactgc tggagttcct gtccactctg gccaggctgc 2760
cgcacctcta caggaacttt gccgcggagc agtatgccag tgtgttcgcc atctccctgc 2820
cgtacaccaa cccctccaag tttaatcagt acatcgtgtg tctggcccat cacgtcatag 2880
ccatgtggtt catcaggtgc cgcctgccct tccggaagga ttttgtccct ttcatcacta 2940
agggcctgcg gtccaatgtc ctcttgtctt ttgatgacac ccccgagaag gacagcttca 3000
gggcccggag tactagtctc aacgagagac ccaagagtct gaggatagcc agaccccccca 3060 aacaaggctt gaataactct ccacccgtga aagaattcaa ggagagctct gcagccgagg 3120
ccttccggtg ccgcagcatc agtgtgtctg aacatgtggt ccgcagcagg atacagacgt 3180
ccctcaccag tgccagcttg ggtctgcag atgagaactc cgtggcccag gctgacgata 3240
gcctgaaaaa cctccacctg gagctcacgg aaacctgtct ggacatgatg gctcgatacg 3300
tcttctccaa cttcacggct gtcccgaaga ggtctcctgt gggcgagttc ctcctagcgg 3360
gtggcaggac caaaacctgg ctggttggga acaagcttgt cactgtgacg acaagcgtgg 3420
gaaccgggac ccggtcgtta ctaggcctgg actcggggga gctgcagtcc ggcccggagt 3480
cgagctccag ccccggggtg catgtgagac agaccaagga ggcgccggcc aagctggagt 3540
cccaggctgg gcagcaggtg tcccgtgggg cccgggatcg ggtccgttcc atgtcggggg 3600
gccatggtct tcgagttggc gccctggacg tgccggcctc ccagttcctg ggcagtgcca 3660
cttctccagg accacggact gcaccagccg cgaaacctga gaaggcctca gctggcaccc 3720
gggttcctgt gcaggagaag acgaacctgg cggcctatgt gcccctgctg acccagggct 3780
gggcggagat cctggtccgg aggcccacag ggaacaccag ctggctgatg agcctggaga 3840
acccgctcag ccctttctcc tcggacatca acaacatgcc cctgcaggag ctgtctaacg 3900
ccctcatggc ggctgagcgc ttcaaggagc accgggacac agccctgtac aagtcactgt 3960
cggtgccggc agccagcacg gccaaacccc ctcctctgcc tcgctccaac acagtggcct 4020
ctttctcctc cctgtaccag tccagctgcc aaggacagct gcacaggagc gtttcctggg 4080
cagactccgc cgtggtcatg gaggagggaa gtccgggcga ggttcctgtg ctggtggagc 4140
ccccagggtt ggaggacgtt gaggcagcgc taggcatgga caggcgcacg gatgcctaca 4200
gcaggtcgtc ctcagtctcc agccaggagg agaagtcgct ccacgcggag gagctggttg 4260
gcaggggcat ccccatcgag cgagtcgtct cctcggaggg tggccggccc tctgtggacc 4320
tctccttcca gccctcgcag cccctgagca agtccagctc ctctcccgag ctgcagactc 4380
tgcaggacat cctcggggac cctggggaca aggccgacgt gggccggctg agccctgagg 4440
ttaaggcccg gtcacagtca gggaccctgg acggggaaag tgctgcctgg tcggcctcgg 4500

```
gcgaagacag tcggggccag cccgagggtc ccttgccttc cagctccccc cgctcgccca   4560

gtggcctccg gccccgaggt tacaccatct ccgactcggc cccatcacgc aggggcaaga   4620

gagtagagag ggacgcctta aagagcagag ccacagcctc caatgcagag aaagtgccag   4680

gcatcaaccc cagtttcgtg ttcctgcagc tctaccattc cccttcttt ggcgacgagt    4740

caaacaagcc aatcctgctg cccaatgagt cacagtcctt tgagcggtcg gtgcagctcc   4800

tcgaccagat cccatcatac gacacccaca agatcgccgt cctgtatgtt ggagaaggcc   4860

agagcaacag cgagctcgcc atcctgtcca atgagcatgg ctcctacagg tacacggagt   4920

tcctgacggg cctgggccgg ctcatcgagc tgaaggactg ccagccggac aaggtgtacc   4980

tgggaggcct ggacgtgtgt ggtgaggacg gccagttcac ctactgctgg cacgatgaca   5040

tcatgcaagc cgtcttccac atcgccaccc tgatgcccac caaggacgtg gacaagcacc   5100

gctgcgacaa gaagcgccac ctgggcaacg actttgtgtc cattgtctac aatgactccg   5160

gtgaggactt caagcttggc accatcaagg gccagttcaa ctttgtccac gtgatcgtca   5220

ccccgctgga ctacgagtgc aacctggtgt ccctgcagtg caggaaagac atggagggcc   5280

ttgtggacac cagcgtggcc aagatcgtgt ctgaccgcaa cctgcccttc gtggcccgcc   5340

agatggccct gcacgcaaat atggcctcac aggtgcatca tagccgctcc aaccccaccg   5400

atatctaccc ctccaagtgg attgcccggc tccgccacat caagcggctc cgccagcgga   5460

tctgcgagga agccgcctac tccaacccca gcctacctct ggtgcaccct ccgtcccata   5520

gcaaagcccc tgcacagact ccagccgagc ccacacctgg ctatgaggtg ggccagcgga   5580

agcgcctcat ctcctcggtg gaggacttca ccgagtttgt gtgaggccgg ggccctccct   5640

cctgcactgg ccttggacgg tattgcctgt cagtgaaata aataaagtcc tgaccccagt   5700

gcacagacat agaggcacag attgcagtca gacaaaaaaa aaaaaaaaaa a            5751
```

<210> SEQ ID NO 6
<211> LENGTH: 467
<212> TYPE: PRT
<213> ORGANISM: Homo sapiens

<400> SEQUENCE: 6

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160
```

```
Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465
```

<210> SEQ ID NO 7
<211> LENGTH: 6107
<212> TYPE: DNA
<213> ORGANISM: Homo sapiens

<400> SEQUENCE: 7

```
aaatgacgac aacggtgagg gttctcgggc ggggcctggg acaggcagct ccggggtccg      60

cggtttcaca tcggaaacaa aacagcggct ggtctggaag gaacctgagc tacgagccgc     120

ggcggcagcg gggcggcggg gaagcgtata cctaatctgg gagcctgcaa gtgacaacag     180

cctttgcggt ccttagacag cttggcctgg aggagaacac atgaaagaaa gaacctcaag     240

aggctttgtt ttctgtgaaa cagtatttct atacagttgc tccaatgaca gagttacctg     300
```

```
caccgttgtc ctacttccag aatgcacaga tgtctgagga caaccacctg agcaatactg    360
tacgtagcca gaatgacaat agagaacggc aggagcacaa cgacagacgg agccttggcc    420
accctgagcc attatctaat ggacgacccc agggtaactc ccggcaggtg gtggagcaag    480
atgaggaaga agatgaggag ctgacattga aatatggcgc caagcatgtg atcatgctct    540
ttgtccctgt gactctctgc atggtggtgg tcgtggctac cattaagtca gtcagctttt    600
atacccggaa ggatgggcag ctaatctata ccccattcac agaagatacc gagactgtgg    660
gccagagagc cctgcactca attctgaatg ctgccatcat gatcagtgtc attgttgtca    720
tgactatcct cctggtggtt ctgtataaat acaggtgcta taaggtcatc catgcctggc    780
ttattatatc atctctattg ttgctgttct ttttttcatt catttacttg gggaagtgt     840
ttaaaaccta taacgttgct gtggactaca ttactgttgc actcctgatc tggaattttg    900
gtgtggtggg aatgatttcc attcactgga aaggtccact tcgactccag caggcatatc    960
tcattatgat tagtgccctc atggccctgg tgtttatcaa gtacctccct gaatggactg   1020
cgtggctcat cttggctgtg atttcagtat atgatttagt ggctgttttg tgtccgaaag   1080
gtccacttcg tatgctggtt gaaacagctc aggagagaaa tgaaacgctt tttccagctc   1140
tcatttactc ctcaacaatg gtgtggttgg tgaatatggc agaaggagac ccggaagctc   1200
aaaggagagt atccaaaaat tccaagtata atgcagaaag cacagaaagg gagtcacaag   1260
acactgttgc agagaatgat gatggcgggt tcagtgagga atgggaagcc cagagggaca   1320
gtcatctagg gcctcatcgc tctacacctg agtcacgagc tgctgtccag gaactttcca   1380
gcagtatcct cgctggtgaa gacccagagg aaaggggagt aaaacttgga ttgggagatt   1440
tcattttcta cagtgttctg gttggtaaag cctcagcaac agccagtgga gactggaaca   1500
caaccatagc ctgtttcgta gccatattaa ttggtttgtg ccttacatta ttactccttg   1560
ccattttcaa gaaagcattg ccagctcttc caatctccat cacctttggg cttgttttct   1620
actttgccac agattatctt gtacagcctt ttatggacca attagcattc catcaatttt   1680
atatctagca tatttgcggt tagaatccca tggatgtttc ttctttgact ataacaaaat   1740
ctggggagga caaaggtgat ttcctgtgt  ccacatctaa caaagtcaag attcccggct   1800
ggacttttgc agcttccttc caagtcttcc tgaccacctt gcactattgg actttggaag   1860
gaggtgccta tagaaaacga ttttgaacat acttcatcgc agtggactgt gtccctcggt   1920
gcagaaacta ccagatttga gggacgaggt caaggagata tgataggccc ggaagttgct   1980
gtgccccatc agcagcttga cgcgtggtca caggacgatt tcactgacac tgcgaactct   2040
caggactacc gttaccaaga ggttaggtga agtggtttaa accaaacgga actcttcatc   2100
ttaaactaca cgttgaaaat caacccaata attctgtatt aactgaattc tgaacttttc   2160
aggaggtact gtgaggaaga gcaggcacca gcagcagaat ggggaatgga gaggtgggca   2220
ggggttccag cttccctttg attttttgct gcagactcat cctttttaaa tgagacttgt   2280
tttcccctct ctttgagtca agtcaaatat gtagattgcc tttggcaatt cttcttctca   2340
agcactgaca ctcattaccg tctgtgattg ccatttcttc ccaaggccag tctgaacctg   2400
aggttgcttt atcctaaaag ttttaacctc aggttccaaa ttcagtaaat tttggaaaca   2460
gtacagctat ttctcatcaa ttctctatca tgttgaagtc aaatttggat tttccaccaa   2520
attctgaatt tgtagacata cttgtacgct cacttgcccc agatgcctcc tctgtcctca   2580
ttcttctctc ccacacaagc agtctttttc tacagccagt aaggcagctc tgtcgtggta   2640
gcagatggtc ccattattct agggtcttac tctttgtatg atgaaaagaa tgtgttatga   2700
```

```
atcggtgctg tcagccctgc tgtcagacct tcttccacag caaatgagat gtatgcccaa   2760
agacggtaga attaaagaag agtaaaatgg ctgttgaagc actttctgtc ctggtatttt   2820
gtttttgctt ttgccacaca gtagctcaga atttgaacaa atagccaaaa gctggtggtt   2880
gatgaattat gaactagttg tatcaacaca aagcaagagt tggggaaagc catatttaac   2940
ttggtgagct gtgggagaac ctggtggcag aaggagaacc aactgccaag ggaaagaga    3000
aggggcctcc agcagcgaag gggatacagt gagctaatga tgtcaaggag gagtttcagg   3060
ttattctcgt cagctccaca aatgggtgct ttgtggtctc tgcccgcgtt acctttcctc   3120
tcaatgtacc tttgtgtgaa ctgggcagtg gaggtgcctg ctgcagttac catggagttc   3180
aggctctggg cagctcagtc aggcaaaaca cacaaacagc catcagcctg tgtgggctca   3240
gggcacctct ggacaaaggc ttgtggggca taaccttctt taccacagag agcccttagc   3300
tatgctgatc agaccgtaag cgtttatgag aaacttagtt tcctcctgtg gctgaggagg   3360
ggccagcttt ttcttctttt gcctgctgtt ttctctccca atctatgata tgatatgacc   3420
tggtttgggg ctgtctttgg tgtttagaat atttgttttc tgtcccagga tatttcttat   3480
aagaacctaa cttcaagagt agtgtgcgag tactgatctg aatttaaatt aaaattggct   3540
tatattaggc agtcacagac aggaaaaata agagctatgc aaagaaaggg ggatttaaag   3600
tagtaggttc tatcatctca attcattttt ttccatgaaa tcccttcttc caagattcat   3660
tccctctctc agacatgtgc tagcatgggt attatcattg agaaagcaca gctacagcaa   3720
agccacctga atagcaattt gtgattggaa gcattcttga gggatcccta atctagagta   3780
atttatttgt gtaaggatcc caaatgtgtt gcacctttca tgatacattt cttctctgaa   3840
gagggtacgt ggggtgtgtg tatttaaatc catcctatgt attactgatt gtcctgtgta   3900
gaaagatggc aattattctg tctctttctc caagtttgag ccacatctca gccacattgt   3960
tagacagtgt acagagaacc tatctttcct tttttttttt ttaaaggaca ggattttgct   4020
gtgttgccca ggctagactt gaactcctgg gctcaagtaa tccacctcag cctgagtagc   4080
tgagactaca gcccatctta tttctttaaa tcattcatct caggcagaga acttttccct   4140
caaacattct ttttagaatt agttcagtca ttcctaaaac atccaaatgc tagtcttcca   4200
ccatgaaaaa tagattgtca ctggaaagaa cagtagcaat ttccataagg atgtgccttc   4260
actcacacgg gacaggcggt ggttatagag tcgggcaaaa ccagcagtag agtatgacca   4320
gccaagccaa tctgcttaat aaaaagatgg aagacagtaa ggaaggaaag tagccactaa   4380
gagtctgagt ctgactgggc tacagaataa agggtattta tggacagaat gtcattacat   4440
gcctatggga ataccaatca tatttggaag atttgcagat tttttttcag agaggaaaga   4500
ctcaccttcc tgtttttggt tctcagtagg ttcgtgtgtg ttcctagaat cacagctctg   4560
actccaaatg actcaatttc tcaattagaa aaagtagaag ctttctaagc aacttggaag   4620
aaaacagtca taagtaagca atttgttgat tttactacag aagcaacaac tgaagaggca   4680
gtgtttttac tttcagactc cgggattccc attctgtagt ctctctgctt ttaaaaaccc   4740
tccttttgca atagatgccc aaacagatga tgtttattac ttgttattta cgtggcctca   4800
gacagtgtat gtattctcga tataacttgt agagtgtgaa atataagttt aactaccaaa   4860
taaggtctcc cagggttaga tgactgcggg aagcctttga tcccaacccc caaggctttg   4920
tatatttgat catttgtgat ctaaccctgg aagaaaaaga gctcagaaac cactatgaaa   4980
aaatttgttc agtgttttct gtgttcccgt aggttctgga gtctgaggat gcaaagatga   5040
```

-continued

| | |
|---|---|
| ataagataaa ttctcagaat gtagttataa tctcttgttt tctggtatat gccatctttc | 5100 |
| tttaacttct ctaaaatatt gggtatttgt caaataacca cttttaacag ttaccattac | 5160 |
| tgagggctta tacattggtg ttataaaagt gacttgattc agaaatcaat ccattcagta | 5220 |
| aagtactcct tctctaaatt tgctgttatg tctataagga acagtttgac ctgcccttct | 5280 |
| cctcacctcc tcacctgcct tccaacattg aatttggaag gagacgtgaa aattggacat | 5340 |
| ttggttttgc ccttgggctg gaaactatca tataatcata agtttgagcc tagaagtgat | 5400 |
| ccttgtgatc ttctcacctc tttaaattcc cacaacacaa gagattaaaa acagaggttt | 5460 |
| cagctcttca tagtgcgttg tgaaatggct ggccagagtg taccaacaaa gctgtcatcg | 5520 |
| ggctcacagc tcagagacat ctgcatgtga tcatctgcat agtcctctcc tctaacggga | 5580 |
| aacacctcag atttgcatat aaaaaagcac cctggtgctg aaatgaaccc ctttcttgaa | 5640 |
| catcaaagct gtctcccaca gccttgggca gcagggtgcc tcttagtgga tgtgctgggt | 5700 |
| ccaccctgag ccctgacatg tggtggcagc attgccagtt ggtctgtgtg tctgtgtagc | 5760 |
| agggacgatt tcccagaaag caattttcct tttgaaatac gtaattgttg agactaggca | 5820 |
| gtttcaaagt cagctgcata tagtagcaag tacaggactg tcttgttttt ggtgtccttg | 5880 |
| gaggtgctgg ggtgagggtt tcagtgggat catttactct cacatgttgt ctgccttctg | 5940 |
| cttctgtgga cactgctttg tacttaattc agacagactg tgaatacacc tttttataa | 6000 |
| ataccttca aattcttggt aagatataat tttgatagct gattgcagat tttctgtatt | 6060 |
| tgtcagatta ataaagactg catgaatcca aaaaaaaaaa aaaaaaa | 6107 |